(12) United States Patent
Cuero Rengifo et al.

(10) Patent No.: US 10,011,841 B2
(45) Date of Patent: Jul. 3, 2018

(54) METHODS AND DEVICES FOR ELECTROMAGNETIC LIGATION OF NUCLEIC ACIDS AND ELECTROMAGNETIC TRANSFORMATION OF CELLS

(71) Applicants: INTERNATIONAL PARK OF CREATIVITY, Bogota (CO); Raul Cuero Rengifo, Cypress, TX (US); Natalia Gutierrez Calle, Manizales (CO); Mariana Sanchez Londono, Manizales (CO)

(72) Inventors: Raul Cuero Rengifo, Cypress, TX (US); Natalia Gutierrez Calle, Manizales (CO); Mariana Sanchez Londono, Manizales (CO)

(73) Assignee: International Park of Creativity, Bogota (CO)

( * ) Notice: Subject to any disclaimer, the term of this patent is extended or adjusted under 35 U.S.C. 154(b) by 282 days.

(21) Appl. No.: 14/909,173

(22) PCT Filed: Jul. 31, 2014

(86) PCT No.: PCT/US2014/049015
§ 371 (c)(1),
(2) Date: Feb. 1, 2016

(87) PCT Pub. No.: WO2015/017604
PCT Pub. Date: Feb. 5, 2015

(65) Prior Publication Data
US 2016/0168578 A1  Jun. 16, 2016

Related U.S. Application Data

(60) Provisional application No. 61/861,464, filed on Aug. 2, 2013.

(51) Int. Cl.
*C12P 19/34* (2006.01)
*C12N 15/64* (2006.01)
*C12Q 1/6844* (2018.01)

(52) U.S. Cl.
CPC ............ *C12N 15/64* (2013.01); *C12P 19/34* (2013.01); *C12Q 1/6844* (2013.01)

(58) Field of Classification Search
CPC ............ C12Q 1/6844; C12Q 2521/501; C12Q 2523/303; C12N 15/64; C12P 19/34

USPC ......................................................... 435/91.2
See application file for complete search history.

(56) References Cited

U.S. PATENT DOCUMENTS

| RE38,442 E * | 2/2004 | Zhang ................. C12Q 1/6813 435/5 |
| 6,878,905 B2 | 4/2005 | Brown et al. |
| 7,820,454 B2 * | 10/2010 | Su ....................... B01F 11/0266 436/526 |
| 2002/0086842 A1 | 7/2002 | Plank et al. |
| 2009/0246834 A1 | 10/2009 | Goel |
| 2010/0184020 A1 * | 7/2010 | Beer ................. B01L 3/502761 435/6.16 |

FOREIGN PATENT DOCUMENTS

| WO | 1996017959 | 6/1996 |
| WO | 2007087690 | 8/2007 |
| WO | 2012145449 | 10/2012 |

OTHER PUBLICATIONS

Potenza et al., Bioelectromagnetics 25: 352-355, (Year: 2004).*
Ding et al. "Single-Molecule Mechanical Identification and Sequencing," Nature Methods, 2012, 9:367-374.
Potter et al., "Transfection by Electroporation," Curr. Protocols in Mol. Biol., 2003, 9.3:1-13.
International Search Report and Written Opinion for PCT/US14/49015 dated Nov. 12, 2014.

* cited by examiner

*Primary Examiner* — Cynthia B Wilder
(74) *Attorney, Agent, or Firm* — Gardner Groff Greenwald & Villanueva, PC

(57) ABSTRACT

Described herein are methods and devices for ligating nucleic acids or nucleic acid fragments as well as methods for transforming or transfecting cells with exogenous DNA. The methods and devices generally involve exposing the nucleic acids, nucleic acid fragments, and/or cells to an electromagnetic field, for example, a mini-current electromagnetic field, while performing the steps of ligation or transformation. The methods and devices provide numerous advantages over conventional ligation and transformation techniques and systems such as reduced reaction times, no heating requirements, and reduced amounts of reagents. Finally, as shown in the examples below, the methods and devices described herein are more effective compared to conventional ligation and transformation techniques and systems.

23 Claims, 36 Drawing Sheets

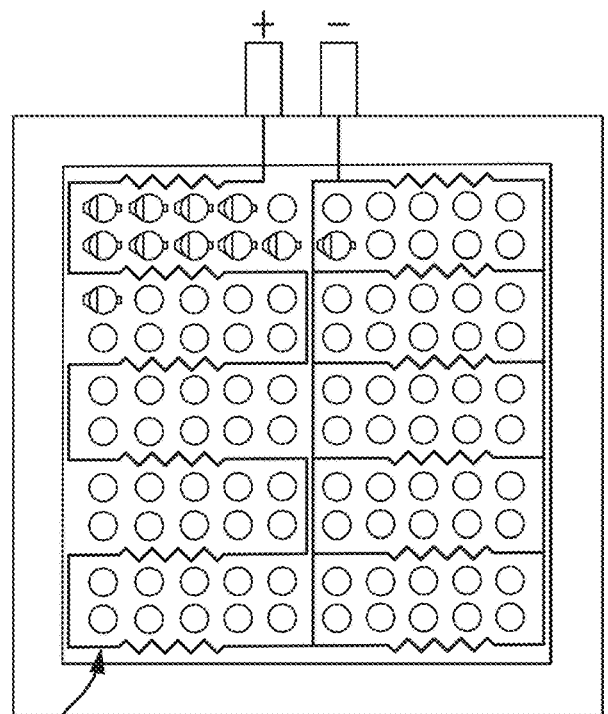
54c(iii) FIG. 12C
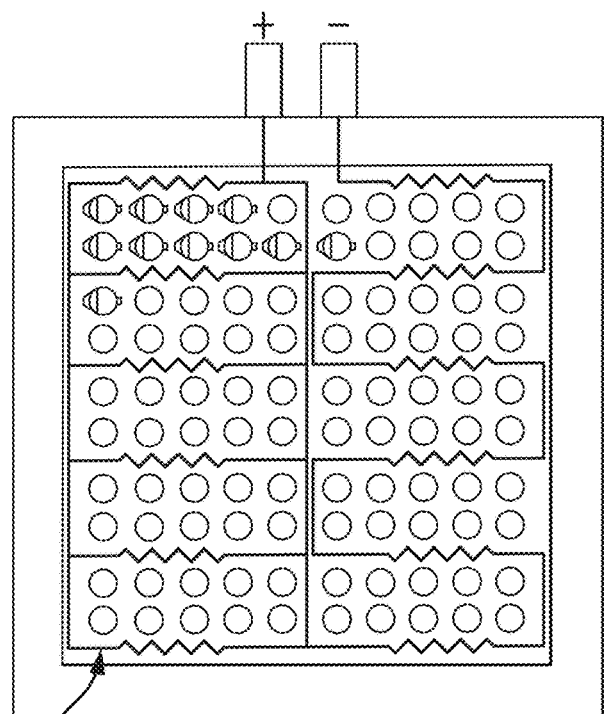
54c(iv) FIG. 12D

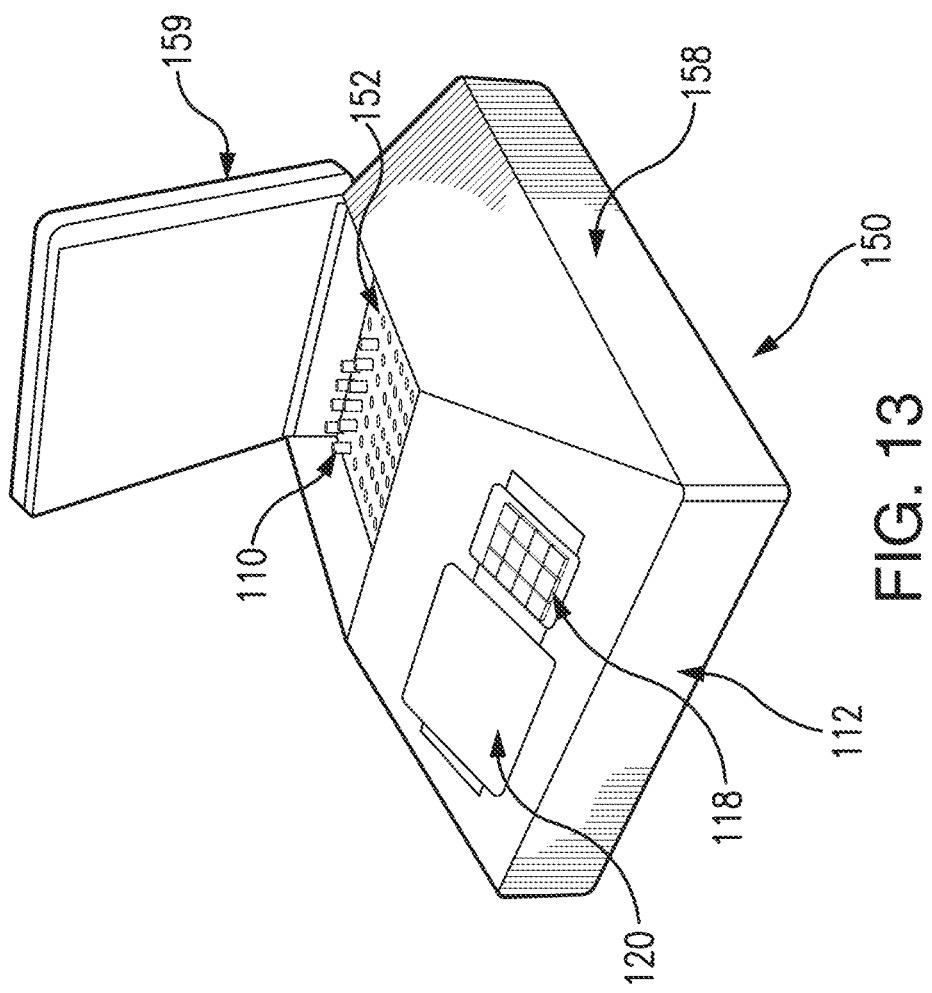

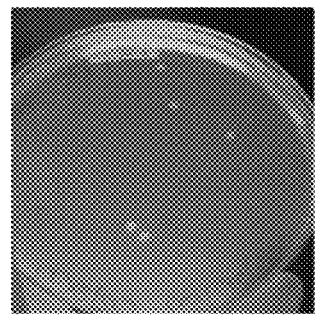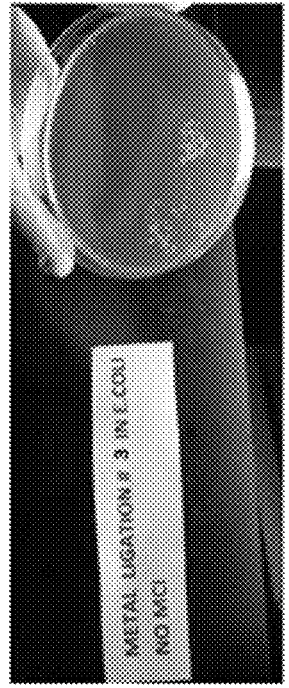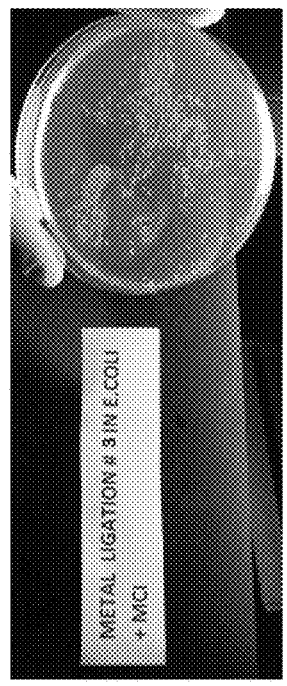
FIG. 37

SEQUENCE LISTING

<160> NUMBER OF SEQ ID NOS: 10

<210> SEQ ID NO 1
<211> LENGTH: 2372
<212> TYPE: DNA
<213> ORGANISM: Artificial sequence
<220> FEATURE:
<223> OTHER INFORMATION: Synthetic construct

<400> SEQUENCE: 1

| | | | | | | |
|---|---|---|---|---|---|---|
| tagaactagt | ggattacccc | cgggctgcag | gaattcgata | tcaaaatgct | gcccggtttg | 60 |
| gcactgctcc | tgctggccgc | ctggacggct | cgggcgctgg | aggtacccac | tgatggtaat | 120 |
| gctggcctgc | tggctgaacc | ccagattgcc | atgttctgtg | gcagactgaa | catgcacatg | 180 |
| aatgtccaga | atgggaagtg | ggattcagat | ccatcaggga | ccaaaacctg | cattgatacc | 240 |
| aaggaaggca | tcctgcagta | ttgccaagaa | gtctaccctg | aactgcagat | caccaatgtg | 300 |
| gtagaagcca | accaaccagt | gaccatccag | aactggtgca | agcggggccg | caagcagtgc | 360 |
| aagacccatc | cccactttgt | gattccctac | cgctgcttag | ttggtgagtt | tgtaagtgat | 420 |
| gcccttctcg | ttcctgacaa | gtgcaaattc | ttacaccagg | agaggatgga | tgtttgcgaa | 480 |
| actcatcttc | actggcacac | cgtcgccaaa | gagacatgca | gtgagaagag | taccaacttg | 540 |
| catgactacg | gcatgttgct | gccctgcgga | attgacaagt | tccgaggggt | agagtttgtg | 600 |
| tgttgcccac | tggctgaaga | aagtgacaat | gtggattctg | ctgatgcgga | ggaggatgac | 660 |
| tcggatgtct | ggtggggcgg | agcagacaca | gactatgcag | atgggagtga | agacaaagta | 720 |
| gtagaagtag | cagaggagga | agaagtggct | gaggtggaag | aagaagaagc | cgatgatgac | 780 |
| gaggacgatg | aggatggtga | tgaggtagag | aagaggctg | aggaaccta | cgaagaagcc | 840 |
| acagagagaa | ccaccagcat | tgccaccacc | accaccacca | ccacagagtc | tgtggaagag | 900 |
| gtggttcgag | aggtgtgctc | tgaacaagcc | gagacgggc | cgtgccgagc | aatgatctcc | 960 |
| cgctggtact | ttgatgtgac | tgaagggaag | tgtgccccat | tctttacgg | cggatgtggc | 1020 |
| ggcaaccgga | acaactttga | cacagaagag | tactgcatgg | ccgtgtgtgg | cagcgccatg | 1080 |
| tcccaaagtt | tactcaagac | tacccaggaa | cctcttgccc | gagatcctgt | taaacttcct | 1140 |
| acaacagcag | ccagtacccc | tgatgccgtt | gacaagtatc | tcgagacacc | tggggatgag | 1200 |
| aatgaacatg | cccatttcca | gaaagccaaa | gagaggcttg | aggccaagca | ccgagagaga | 1260 |
| atgtcccagg | tcatgagaga | atgggaagag | gcagaacgtc | aagcaaagaa | cttgcctaaa | 1320 |
| gctgataaga | aggcagttat | ccagcatttc | caggagaaag | tggaatcttt | ggaacaggaa | 1380 |
| gcagccaacg | agagacagca | gctggtggag | acacacatgg | ccagagtgga | agccatgctc | 1440 |
| aatgaccgcc | gccgcctggc | cctggagaac | tacatcaccg | ctctgcaggc | tgttcctcct | 1500 |
| cggcctcgtc | acgtgttcaa | tatgctaaag | aagtatgtcc | gcgcagaaca | gaaggacaga | 1560 |
| cagcacaccc | taaagcattt | cgagcatgtg | cgcatggtgg | atcccaagaa | agccgctcag | 1620 |
| atccggtccc | aggttatgac | acacctccgt | gtgatttatg | agcgcatgaa | tcagtctctc | 1680 |
| tccctgctct | acaacgtgcc | tgcagtggcc | gaggagattc | aggatgaagt | tgatgagctg | 1740 |
| cttcagaaag | agcaaaacta | ttcagatgac | gtcttggcca | acatgattag | tgaaccaagg | 1800 |
| atcagttacg | gaaacgatgc | tctcatgcca | tctttgaccg | aaacgaaaac | caccgtggag | 1860 |
| ctccttcccg | tgaatggaga | gttcagcctg | gacgatctcc | agccgtggca | ttcttttggg | 1920 |
| gctgactctg | tgccagccaa | cacagaaaac | gaagttgagc | tgttgatgc | ccgccctgct | 1980 |
| gccgaccgag | gactgaccac | tcgaccaggt | tctggggtga | caaatatcaa | gacggaggag | 2040 |

```
atctctgaag tgaagatgga tgcagaattc cgacatgact caggatatga agttcatcat    2100
caaaaattgg tgttctttgc agaagatgtg ggttcaaaca aaggtgcaat cattggactc    2160
atggtgggcg tgttgtcat agcgacagtg atcgtcatca ccttggtgat gctgaagaag     2220
aaacagtaca catccattca tcatggtgtg gtggaggttg acgccgctgt caccccagag    2280
gagcgccacc tgtccaagat gcagcagaac ggctacgaaa tccaaccta caagttcttt    2340 gagcagatgc agaactgaaa gcttatcgat ac                                  2372

<210> SEQ ID NO 2
<211> LENGTH: 1391
<212> TYPE: DNA
<213> ORGANISM: Artificial Sequence
<220> FEATURE:
<223> OTHER INFORMATION: Synthetic construct

<400> SEQUENCE: 2
gggatctcga ggaattctca ctggaacagc gcgtcactcg acaggccatt cttctccaga      60
atctcccgca ggcgcttcag cgcctcgacc tggatctgac gaacccgctc gcgggtcagg     120
ccgatttcct ggccgacctc ttccagcgtg ctgctttcgt gaccgcgcaa gccgaagcgg     180
cgaatcacca cctcacgctg cttgtcggtg agttccgtca gctgctttcg ctgagatcgt     240
catcctgcag cagctcgcac ggatcggtgg ggcgatcgtc ggtgagcgta tccagcaggg     300
tcttgtccga gtccggacca agagagacgt ctaccgaagt cacccgttcg ttcaggccga     360
gcatgcgctt gacctcggcg accggcttct ccagcaggtt ggcgatttct tcgggtgaag     420
gttcgtggtc gagcttgtgg gtcagttccc gcgccgcacg caggtagacg ttgagctcct     480
tgaccacatg gatcggcaag cgaatggtcc gggtctggtt catgatggcc cgctcgatgg     540
tctggcggat ccaccaggtg gcgtaggtcg agaaccggaa tccgcgctcc ggatcgaact     600
tctccacggc gcggatcagg cctaggttgc cttcctcgat caggtcgagc agggacagtc     660
cgcgattgac atagcgccgg gcgatcttca ccaccaaccg caggttgctc tcgatcatcc     720
gcttccgacc agcgggatcg cccttctgcg ccagacgagc gaagtggact tcctcttcgg     780
gcgtcaacag gggcgagaaa ccgatttcgt tgagatacag ctgcgttgcg tccaacgcgc     840
gcgtgtagtc gatgtgcttg tgttgtttgg aagagaagga agtggtggct tttggagttg     900
cccggggaga aggctgctcg tcggcagacg actcgtccag catgatgccg gctccagga     960 ggagcacttc atcatcgtgg tcaaactccg gcccttcttt tttgagtgcc atgtcgttat    1020
cccttgcatg agttcgactc aagcccgggc gattcctttc ccgctggaca cgcccggacc    1080
cgctcaccta catgatgtgg gcgggcgaac tcccggtcag cgacgtggca aatattgcag    1140
tggatcgaca ggcttaccct ggcggcgaat ctcgaagtgc agcttcaccc gatcggttcc    1200
tgtggagccc atctcggcaa tcgattgccc taccttgacc tgttgccctt cccgcaccag    1260
cagcctgcgg ttgtgaccgt aggcactcac gtaggtctcg ttgtgtttga tgatgaccaa    1320
ctcgccgtag ccccgcaaac cactaccggc gtatacaacg gtcccaccag acgcagccag    1380
gtaccaagct t                                                         1391

<210> SEQ ID NO 3
<211> LENGTH: 747
<212> TYPE: DNA
<213> ORGANISM: Artificial Sequence
<220> FEATURE:
<223> OTHER INFORMATION: Synthetic construct
```

<400> SEQUENCE: 3

```
gaattcatga cgaaaacgcg ctcgaacatg gcgcgctacg gcaccagcct ggccatcgtg      60
ctgggcgtgc acgtggtcgc cgtggtgctg acgctcaact ggtcggtgcc ccaggccatc     120
gagctgccgc cggcagcgat gatggtcgag ttggcgccgt tgccgagcc cgcgccaccg      180
ccaccgccca aggccgcgcc caagccaccg gcagaggtcg aggagccgcc gctgcccaag     240
ctggtggagg cccccaagcc gaagatcgcc atcgccaagc cgcccaagcc caaggccaag     300
ccgcagccgc ccaagcctga aaaagcct gagccgccga aggacgaacc accggccaag       360
gacgatgtgg cggataccc gccaagcaac gcgcagccgc agaaatcggc cgcaccggca      420
ccgagcatcg cctccaacag caatgccctg cccagctggc agagcgacct gctgcgccac     480
ctggccaagt acaagaagta cccggaagac gctcgccgtc gcggcctgca gggcatcaac     540
cgcctgcgct tcgtggtcga cgccgagggc aaggtagtct cgtactcgct ggccggaggc     600
tcgggcagcg cggcgctgga ccgggcgacc ctggaaatga tccgtcgcgc aggctccgta     660
ccgaagccgc cagcggagct gttgaacaat ggcacgatcg aagtcgtggc gccgttcgtc     720
tattccctgg accgacgctg aggatcc                                         747
```

<210> SEQ ID NO 4
<211> LENGTH: 890
<212> TYPE: DNA
<213> ORGANISM: Artificial Sequence
<220> FEATURE:
<223> OTHER INFORMATION: Synthetic construct

<400> SEQUENCE: 4

```
ggattcaaag aggagaaata ctagatggtg agcaagggcg aggagctgtt caccggggtg      60
gtgcccatcc tggtcgagct ggacggcgac gtaaacggcc acaagttcag cgtgtccggc     120
gagggcgagg gcgatgccac ctacggcaag ctgaccctga agttcatctg caccaccggc     180
aagctgcccg tgccctggcc caccctcgtg accaccttcg gctacggcct gcaatgcttc     240
gcccgctacc ccgaccacat gaagctgcac gacttcttca gtccgccat gcccgaaggc      300
tacgtccagg agcgcaccat cttcttcaag gacgacggca actacaagac ccgcgccgag     360
gtgaagttcg agggcgacac cctggtgaac cgcatcgagc tgaagggcat cgacttcaag     420
gaggacggca acatcctggg gcacaagctg gagtacaact acaacagcca caacgtctat     480
atcatggccg acaagcagaa gaacggcatc aaggtgaact tcaagatccg ccacaacatc     540
gaggacggca gcgtgcagct cgccgaccac taccagcaga caccccccat cggcgacggc     600
cccgtgctgc tgcccgacaa ccactacctg agctaccagt ccgccctgag caaagacccc     660
aacgagaagc gcgatcacat ggtcctgctg gagttcgtga ccgccgccgg gatcactctc     720
ggcatggacg agctgtacaa gtaataatac tagagccagg catcaaataa aacgaaaggc     780
tcagtcgaaa gactgggcct ttcgttttat ctgttgtttg tcggtgaacg ctctctacta     840
gagtcacact ggctcacctt cgggtgggcc tttctgcgtt tataaagctt                 890
```

<210> SEQ ID NO 5
<211> LENGTH: 1098
<212> TYPE: DNA
<213> ORGANISM: Artificial sequence
<220> FEATURE:
<223> OTHER INFORMATION: Synthetic construct

<400> SEQUENCE: 5

```
ggatccgaat tcgcggccgc ttctagatga cgcttgtcga cagattgcgc ggcgccgtgg      60
```

```
cggggatgcc gcgccggctc gtggtggggg ccgctggtgc ggcgctgctc tcgggcctga      120
ttggcgccgt cggggctcg gcgaccgccg gggccttctc gcgccccggt ctgccggtgg       180
agtacctgca ggttccctcc gccgccatgg gacgggacat caaggtccag ttccaaagcg      240
gtggggccaa ctcgcccgcg ttgtacctgc tcgacgggat gcgcgcgcaa gacgacttca     300
acggctggga catcaacacc ccggcgttcg agtggtacaa ccagtcgggc atctcggtcg      360
ccatgccggt cggcggccag tccagcttct actccgactg gtacaagccc gcctgcggca     420
aggccggctg caccacctac aagtgggaga ccttcctgac cagcgagctg ccgcagtacc     480
tgtcggcgca gaagcaggtc aagccgaccg gcagcggtgt cgtcggcctg tcgatggccg    540
gctcctcggc gctgatcctg gccgcctacc accccgacca gttcgtctac gccggctcgc    600
tgtcggcgct gctggactcg tcgcagggca tgggcccgtc gctgatcggg ctggccatgg   660
gtgacgccgg tggctacaag gccgccgaca tgtggggtcc gaaggaggac ccggcctggg   720
cccgcaacga cccgtcgctg caggtcggca agctggtcgc gaacaacacc cggatctggg    780
tgtactgcgg caacggcaag ccgtccgacc tcggtggcga caacctgccc gccaagttcc    840
tcgagggctt cgtgcggacg tccaacctga agttccagga cgcctacaac ggcgccggcg    900
gccacaacgc ggtgtggaac ttcgacgcca acggcaccca cgactggccc tactggggcg     960
cgcagctgca ggcgatgaag cctgacctgc agtcggtgct gggcgccacc ccgggcgccg    1020
gtccggccac ggccgcggcc accaatgctg ggaacggcca gggcacctaa ctactagtag    1080
cggccgctgc agaagctt                                                 1098

<210> SEQ ID NO 6
<211> LENGTH: 753
<212> TYPE: DNA
<213> ORGANISM: Artificial sequence
<220> FEATURE:
<223> OTHER INFORMATION: Synthetic construct

<400> SEQUENCE: 6
agatctaaag aggagaaaat gacccttgat ttacctcgcc gcttccctg gccgacgtta       60 cttttcggtct gcattcatgg tgctgttgtg gcgggtctgc tctataccct ggtacatcag    120
gttattgaac tacctgcgcc tgcgcagccg atttctgtca cgatggttgc gcctgctgat    180
ctcgaaccgc cacaagccgt tcagccgcca ccggagccgg tggtagagcc agaaccggaa   240
cctgagccga tccccgaacc gccaaaagaa gcaccggtgg tcattgaaaa gccgaagccg    300
aaacctaagc caaaaccgaa gccggtgaaa aaggtacagg agcagcaaaa acgcgatgtc    360
aaacccgtag agtcgcgtcc ggcatcaccg tttgaaaata cggcaccggc acgcccgaca    420
tcaagtacag caacggctgc aaccagcaag ccggttacca gtgtggcttc aggaccacgc   480
gcattaagcc gtaatcagcc gcagtatccg gcacgagcac aggcattgcg cattgaaggg   540
caggttaaag ttaaatttga cgtcacgccg gatggtcgcg tggataacgt acaaatcctc    600
tcagccaagc ctgcgaacat gtttgagcgt gaggtgaaaa atgcgatgcg cagatggcgt    660
tatgagccgg gtaagccagg cagtgggatt gtggtgaata tcctgtttaa aattaacggc    720
accaccgaaa ttcagtaagg atcctcagaa ttc                                 753

<210> SEQ ID NO 7
<211> LENGTH: 1005
<212> TYPE: DNA
<213> ORGANISM: Artificial sequence
<220> FEATURE:
```

<223> OTHER INFORMATION: Synthetic construct

<400> SEQUENCE: 7

```
aagcttatgc agccccagtc cgttctgcac agcggctact ccacccact acttcgggcc      60
tggcagacag ccaccaccac cctcaatgcc tccaacctca tctacccat ctttgtcacg     120
gatgttcctg atgacataca gcctatcacc agcctcccag gagtggccag gtatggtgtg    180
aagcggctgg aagagatgct gaggcccttg gtggaagagg gcctacgctg tgtcttgatc    240
tttggcgtcc ccagcagagt tcccaaggac gagcggggtt ccgcagctga ctccgaggag    300
tccccagcta ttgaggcaat ccatctgttg aggaagacct tccccaacct cctggtggcc    360
tgtgatgtct gcctgtgtcc ctacacctcc catggtcact gcgggctcct gagtgaaaac    420
ggagcattcc gggctgagga gagccgccag cggctggctg aggtggcatt ggcgtatgcc    480
aaggcaggat gtcaggtggt agccccgtcg gacatgatgg atggacgcgt ggaagccatc    540
aaagaggccc tgatggcaca tggacttggc aacagggtat cggtgatgag ctacagtgcc    600
aaatttgctt cctgtttcta tggcccttc cgggatgcag ctaagtcaag cccagctttt    660
ggggaccgcc gctgctacca gctgcccccct ggagcacgag gcctggctct ccgagctgtg    720
gacgggatg tacgggaagg agctgacatg ctcatggtga gcccgggaat gccctacctg    780
gacatcgtgc gggaggtaaa ggacaagcac cctgacctcc ctctcgccgt gtaccacgtc    840
tctggagagt ttgccatgct gtggcatgga gcccaggccg gggcattga tctcaaggct    900
gccgtactgg aggccatgac tgccttccgc agagcaggtg ctgacatcat catcacctac    960
tacacaccgc agctgctgca gtggctgaag gaggaatgag gatcc                   1005
```

<210> SEQ ID NO 8
<211> LENGTH: 1935
<212> TYPE: DNA
<213> ORGANISM: Artificial sequence
<220> FEATURE:
<223> OTHER INFORMATION: Synthetic construct

<400> SEQUENCE: 8

```
agatctatga tgagctatag cgaacgtctg ggtggtcctg cagtaagccc gctgccagtc     60
cgtggtcgtc acatggttca tggcgcagcc ttcgcgtatg tcccaagccc tcaggtactg    120
catcgcattc cgggtactac gacgtacgct attagcagcc tgagtccggt cgcgctgacg    180
gagcactctt gcccgtatgg cgaggttctg gagtgccacg atccgctgcc tgcaaaactg    240
gcgcaggaag aagagcaaaa gcctgaacca cgtctgagtc agaaactggc acaagttggg    300
actaagctgc tgaaagtgcc gctgatgctg ggctttctgt acctgttcgt gtgctctctg    360
gacgttctga gctctgcgtt tcaactggct ggcggtaaag tggccggtga tattttcaag    420
gataatgcaa ttctgtctaa tccggtggcg ggcctggttg tgggcattct ggtgactgtg    480
ctggtccaga gttctagcac ctctacaagc attattgtaa gcatggtaag ctctggtctg    540
ctggaagtaa gcagcgcgat tcctatcatt atgggcagca cattggcac tagtgtaacc    600
aatacgatcg ttgctctgat gcaggcaggc gatcgtaccg attttcgccg tgcctttgct    660
ggtgcgaccg ttcatgactg tttcaactgg ctgagcgttc tggtcctgct gccgctggag    720
gcagcaaccg gctacctgca tcatgttacc ggtctggtgg ttgccagttt taacattcgt    780
ggcggccgtg acgcaccaga cctgctgaaa gtaatcacgg aaccgttcac caaactgatt    840
atccaactgg acaaaagcgt gattaccagc atcgccgtcg gtgatgaaag cctgcgtaac    900
cacagcctga ttcgtatttg gtgccaaccg gaaaccaagg aagccagcac aagtatgtct    960
```

```
cgcgtggagg ctattggtag cctggctaac acaaccatgg agaaatgcaa ccatattttc    1020
gtggatactg gcctgccgga tctggcagtt ggtctgatcc tgctggcggg tagtctggtg    1080
gttctgtgca cctgtctgat tctgctggtg aaaatgctga atagcctgct gaaagggcag    1140
gtggcgaacg tcattcagaa agtgattaat accgacttcc cagcgccttt cacctgggtg    1200
acaggctatt ttgcgatggt cgtgggtgcg agcatgactt ttgtcgtaca gagttcttct    1260
gtctttactt ctgctatcac tcctctgatt ggcctgggcg ttatctctat cgaacgcgcg    1320
tacccgctga cactgggctc taacatcggt acgaccacga cagctatcct ggctgcgctg    1380
gcgtctcctc gtgaaaagct gagtagttct ttccagattg ctctgtgtca cttcttcttt    1440
aatatctctg gtatcctgct gtggtatccg ctgccatgta cacgtctgcc gatccgtatg    1500
gccaaagcgc tgggcaaacg caccgcgaaa tatcgttggt ttgcggtcct gtacctgctg    1560
gtctgttttc tgctgctgcc gtctctggtt ttcggtatca gtatggcagg ctggcaggcc    1620
atggtgggtg taggcacgcc ttttggcgcc ctgctggcgt ttgtggtgct ggttaatgtt    1680
ctgcaaagtc gcagtccggg tcacctgccg aaatggctgc aaacgtggga ttttctgccg    1740
cgctggatgc atagtctgca gccgctggat ggtctgatca cccgcgccac actgtgttat    1800
gcacgcccgg agccgcgcag tccgcagctg ccgccacgcg tgtttctgga agaactgcca    1860
ccggcaacgc cgagtccacg cctggccctg ccagcccatc ataatgccac gcgcctgtaa    1920
ggatccatag aattc                                                    1935

<210> SEQ ID NO 9
<211> LENGTH: 1335
<212> TYPE: DNA
<213> ORGANISM: Artificial sequence
<220> FEATURE:
<223> OTHER INFORMATION: Synthetic construct

<400> SEQUENCE: 9
agatctactg gatccatgaa tgatgaaaac tacagcacga caatttacaa ccgtgttcag      60
accgagcgcg tatacgaaga ttctgacccg gccgaaaacg gcggcccgct gtacgacgaa     120
gtgcacgaag acgtacgccg cgaagataac ctgtatgtaa atgaactgga aaaccaagaa     180
tacgacagcg tggcagtcta tcctgtgggt cgtcagggcc gtactagtgc gagtctgcag     240
ccagaaactg gtgaatacgt cctgccggac gaaccgtaca gcaaagctca ggacccgcac     300
ccaggcgaac ctacggcaga tgaagacatt tctctggagg aactgctgag cccgaccaag     360
gaccatcaga gcgacagtga agagcctcag gcgagcgacc cggaagaacc acaagccagc     420
gacccggaag agccgcaagg tccagatccg gaagaaccgc aagaaaacgg gaacgaaatg     480
gaggcggatc tgccgagtcc gtctagtttc accattcaaa atagccgtgc atttagcacg     540
cgtgaaattt ctccaaccag ctatagtgca gatgacgtaa gtgagggcaa tgaatctgcc     600
tctgcaagcc cggagatcaa cctgtttgtt aaagcgggca tcgatggtga atctatcggc     660
aattgtccgt ttagtcagcg tctgttcatg atcctgtggc tgaaaggcgt tgttttcaat     720
gtgacgacgg tggacctgaa acgtaagcca gccgatctgc acaatctggc gcctggtacc     780
catcctccgt ttctgacttt taacggtgat gtgaagaccg atgtgaacaa atcgaagaa      840 tttctggaag aaacgctgac accggaaaag tatccacgtc tggccgcgaa gcatcgtgag     900
tctaacacag cgggcatcga catctttgtt aaattcagcg cgtatattaa gaatacaaaa     960
cagcagtcta atgcagcact ggaacgcggg ctgaccaaag cactgaagaa actggatgat    1020
```

```
tatctgaaca ctccactgcc agaggagatt gatgctgata ctcgtggtga tgacgagaaa      1080
gggagccgtc gcaaatttct ggacggtgat gagctgacac tggcggattg caatctgctg      1140
cctaaactgc atgtggtcaa aattgttgcg aagaaatatc gcaattatga tttccctgct      1200
gagatgaccg tctgtggcg ctatctgaag aatgcttatg ctcgcgatga gttcaccaac       1260
acctgcgctg ccgatagcga gattgagctg gcctatgccg atgtcgccaa acgcctgtct      1320
cgcagttaag aattc                                                       1335

<210> SEQ ID NO 10
<211> LENGTH: 2325
<212> TYPE: DNA
<213> ORGANISM: Artificial sequence
<220> FEATURE:
<223> OTHER INFORMATION: Synthetic construct

<400> SEQUENCE: 10
agatctaaag aggagaaaat gccattcatt aagagtcgca acacctcat cacagcaacg        60 gccagcagcc gccacctcac cgcagctgcc ctactgtcct ctttctcatt ctcattctca      120
tttgtcgctc aggcacaagc gatcccaatc accacgctcg acaaaattga cgtacaagct      180
gaacaactaa aacgctattc cgcagacaaa cctacctatg gcaagtacac ccaaccactg      240
atcgacacca cccagaccat taacatcatt ggcaaaactc tgttcaacga caaggcgcc       300 acctcactca ccgaagcatt acgcaacagc ccgggcgtag caccttcta cgtcggcgaa       360 aacgggacca cctcaagagg tgacagcgtc tatatgcgcg gcttcgacag ttccagcagc      420
atctatgtcg atggcatccg tgaccttggc tcaatcaccc gggacgtctt caacctggaa      480
caaatagaag tcaccaaagg cccgtctgga cccgactacg gacgtacttc gccgactggc      540
gcgattaacc tgatcaccaa acagcccttt ctacacaatg ccaacactgc aagcatctcc      600
tatggcacag cttcgcaacg ccgcatcacc agcgaccta atctcattgt cagccctgat      660
tcggcattcc gcttaaacat catgggacaa gacatcgggg ttccaggacg caacaatgtc      720
aaaaacaaac gctggggtct ggccccatca gcagcatttg gcctgggaac cagcacccgc      780
gtattcgtca atttgcaata tatcaaccag aacaacattc cagacggcgg cgtgctcacc      840
attggcttac ccggctacag cacccccagac agcacacgga cacaaatcag cgccgcaccg      900
cgcgtggaca gcaaaaactt ctatggaacc ggatcagatt tcgaacatgt gaaatcgtcc      960
atgacaaccg tacgtattga gcacgatatc aatgacaaaa cgaaactgca aaataccttg     1020
cgctggggtc gcaacgaaca gagttaccta ctgacctcct accgcggcaa cgtagagaac     1080
ttaataacac cggacctagc cgatccttcg acctggacaa tcaaccgtga ataccaata      1140 ttcaagaatc aaaccaacac gattttgacc aaccaaacca accttaatct gactctgaaa     1200
accggcccga tcgaacacaa catcgccact ggtatggaac tgacccgtga acggatgcaa     1260
ggctacggta tcagcagcag cggtcgctgg ccggcagcca acctgtacca cccggacccg     1320
gacgtcagcg ggctgcactg ggcagccaat ggcgcctatg ccaacggacg tactgatacc     1380
accgcgtttt acctgttcga tacacttaag ctcaatcagc attggcagct caacagcggc     1440
ctgcgctggg accgctataa caccgactat gcggcactgc tctgcgaccc agtacgtagc     1500
cgcatctact gcaacacaac acctatcaca ctcaatcggt tcaatggcaa cacgtccggg     1560
acgctgttcg gctggaaaac ggggatatta tttaaaccca ccaaacacag cagcctctac     1620
atcaactacg ccgtgtccca acaaccaccc ggaggttcct cactgatct cagtgccaaa      1680 ccccaggatg ccaataaccc gaagtaccaa ccacaaacgg cacgcaccgc agaagcaggt     1740
```

```
gtgaagtgga actcgtctca agaaggcttg caactgaccg ccgccatata caacacccag    1800
gtcaaaaacg acatcgtgca agacccatc  gacctacagt attaccaaaa tggtaagaaa    1860
cgcgtgcgcg gtgttgaact cagcgcagtc ggcaaaatca ccaatgcctg gtcaatatcg    1920
gcagggttca ctacgatgga cgccaaagtc aaacagggac cctcggtctc ggccgacggt    1980
tcacccacac ttgcttacac gcccaatcaa gcattcaccg cctggagcac atacaccctc    2040
ccatttggcc tgaccatcgg cggtggcgca cgctacgtcg gagaaatgaa acgcgacagt    2100
aaaaccgcga tcgggacgcc aacctatatc aagagctact gggccctaga catggtactt    2160
agctaccgcc tgaacgaaca cctggatcta cggctgaaca gctacaactt gttaaataaa    2220
gactacgtcg cagcgatcaa caagagtggc tatcggtatg caccagggat cccacgtgcg    2280
tttctactga cagcaaactt ccacttctaa ggatcctcag aattc                    2325
```

METHODS AND DEVICES FOR ELECTROMAGNETIC LIGATION OF NUCLEIC ACIDS AND ELECTROMAGNETIC TRANSFORMATION OF CELLS

CROSS REFERENCE TO RELATED APPLICATION

This application claims priority upon U.S. Provisional Application Ser. No. 61/861,484, filed Aug. 2, 2013. The application is hereby incorporated by reference in its entirety for all of its teachings.

CROSS REFERENCE TO SEQUENCE LISTING

The genetic components described herein are referred to by a sequence identifier number (SEQ ID NO). The SEQ ID NO corresponds numerically to the sequence identifiers <400>1, <400>2, etc. The Sequence Listing, in written computer readable format (CFR), is incorporated by reference in its entirety.

BACKGROUND

Molecular biology techniques allow for the insertion of a gene or genes of interest into an expression vector, transformation of a cell with the expression vector, and the expression of a protein of interest in the transformed cell. The inserted genes can be from the same cell type or the same organism as the transformed cells, or can be from different organisms or different cell types, or can even be synthetic constructs. Commonly, the expression vector is an independently replicating piece of DNA such as a plasmid and contains an origin of replication, a multiple cloning site, and one or more regulatory elements. Different selective markers, such as genes for antibiotic resistance, may also be included as part of plasmids. Linear nucleic acids are subject to degradation by nucleases, and individual genes do not contain all the regulatory elements required for their own expression in cells. Thus, ligase enzymes are employed as part of the process of inserting a gene or genes of interest into a plasmid or other vector.

Traditional nucleic acid ligases catalyze the formation of a covalent bond between a 3' hydroxyl group and a 5' phosphate group. A variety of ligases are commercially available; some are optimized for ligation of sticky ends, while others can perform blunt end ligations. Many DNA ligases repair single strand breaks in duplex DNA, although some ligases are also able to repair double strand breaks.

However, conventional methods for ligation in molecular biology possess some significant disadvantages. Ligation with commercially-available ligases requires long periods of incubation at reduced temperatures (usually 16° C. overnight), the use of enzymes and the optimization of conditions for best enzyme performance, and high ratios of insert DNA to vector for multiple gene insertions (sometimes up to 6:1). Even with well-established protocols, many ligation reactions do not proceed to completion with high yields. Further, some ligation protocols involve the use of polyethylene glycol (PEG), which can inhibit later attempts at transformation.

Once the gene or genes of interest have been ligated into the expression vector, the vector must be inserted into the cell in which the gene(s) will be expressed; this process is known as transformation. Cells to be transformed may be naturally competent (i.e., able to take up exogenous nucleic acids) or may be made competent through various procedures. Several methods of transformation are commonly practiced. In one method of chemical transformation, competent cells and the vector to be taken up, along with excess carrier DNA, are placed in a solution containing lithium acetate and PEG. This solution is then incubated at 30° C.; dimethylsulfoxide (DMSO) is added, and the sample is heat-shocked, which creates pores in the cell membrane through which the expression vector can enter.

Electroporation, meanwhile, is more effective than chemical transformation. Electroporation can be practiced on nearly any kind of cell, including bacteria, yeast, and plant protoplasts. However, electroporation requires direct contact of an electrode with a solution containing the cells to be transformed. This is commonly accomplished in a special cuvette with aluminum sides. Electroporation creates an electromagnetic field inside a container or cuvette holding the cells to be transformed, and typically, several hundred volts are required (e.g. at room temperature, depending on cell size, from 100-500V are applied to the sample). After electroporation, cells must be handled carefully for an hour or more, or at least the time required for one cycle of cell division.

Conventional methods for transformation are inefficient, resulting in 10% or fewer cells taking up the desired exogenous DNA. Transformation efficiency can be increased through the use of time-consuming purification methods (ethanol precipitation, phenol/chloroform extraction, desalting, spin columns, gel purifications, etc.). In the case of electroporation, costly equipment and specialized sample holders are needed, making it difficult to process many samples in parallel. Further, heat shock steps may damage some cells.

Thus, a need exists for faster, more efficient methods to ligate nucleic acid fragments and to transform cells with exogenous DNA. Ideally, such a method would be substantially heat-free, would require fewer reagents and steps than conventional molecular biology techniques, and would result in improved ligation yields and transformation efficiencies. The present application addresses these needs.

SUMMARY

Described herein are methods and devices for ligating nucleic acids or nucleic acid fragments as well as methods for transforming or transfecting cells with exogenous DNA. The methods and devices generally involve exposing the nucleic acids, nucleic acid fragments, and/or cells to an electromagnetic field, for example, a mini-current electromagnetic field, while performing the steps of ligation or transformation. The methods and devices provide numerous advantages over conventional ligation and transformation techniques and systems such as reduced reaction times, no heating requirements, and reduced amounts of reagents. Finally, as shown in the examples below, the methods and devices described herein are more effective compared to conventional ligation and transformation techniques and systems.

The advantages described above and below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE DRAWINGS

The accompanying drawings, which are incorporated in and constitute a part of this specification, illustrate several aspects described below.

FIGS. 12A-12F are bottom-side plan views of vial-support plates with magnetic-field-inducing circuits of the device according to additional alternative embodiments.

FIG. 13 is a top perspective view of a device for ligating nucleic acids according to a third example embodiment of the present invention, or for transforming cells with nucleic acids according to a fourth example embodiment of the present invention, showing the device holding vials containing the nucleic acids and/or cells and including an integral control unit.

FIG. 36A shows cells transformed with tocopherol PT DNA that had first been amplified using an electromagnetic PCR process. FIG. 36B shows cells transformed with tocopherol PT DNA that had first been amplified using a traditional thermocycler PCR process. FIG. 36C shows cells transformed with tocopherol PT DNA that had not been amplified. Exogenous plasmids transformed into the *E. coli* cells contained an ampicillin resistance gene; cells were plated on media containing ampicillin. Visible colonies represent successful transformations.

FIG. 37 shows plated transformed *E. coli* cells. FIG. 37A shows a control wherein the exogenous DNA was a commercially-available plasmid with no inserted parts. FIG. 37B shows cells containing the ligation device depicted in FIG. 33 wherein ligation was performed without ligase, in the electromagnetic chamber described herein. FIG. 37C shows cells containing the ligation device depicted in FIG. 33 wherein ligation was performed with ligase at room temperature without exposure to a magnetic field.

DETAILED DESCRIPTION

Figure 1:
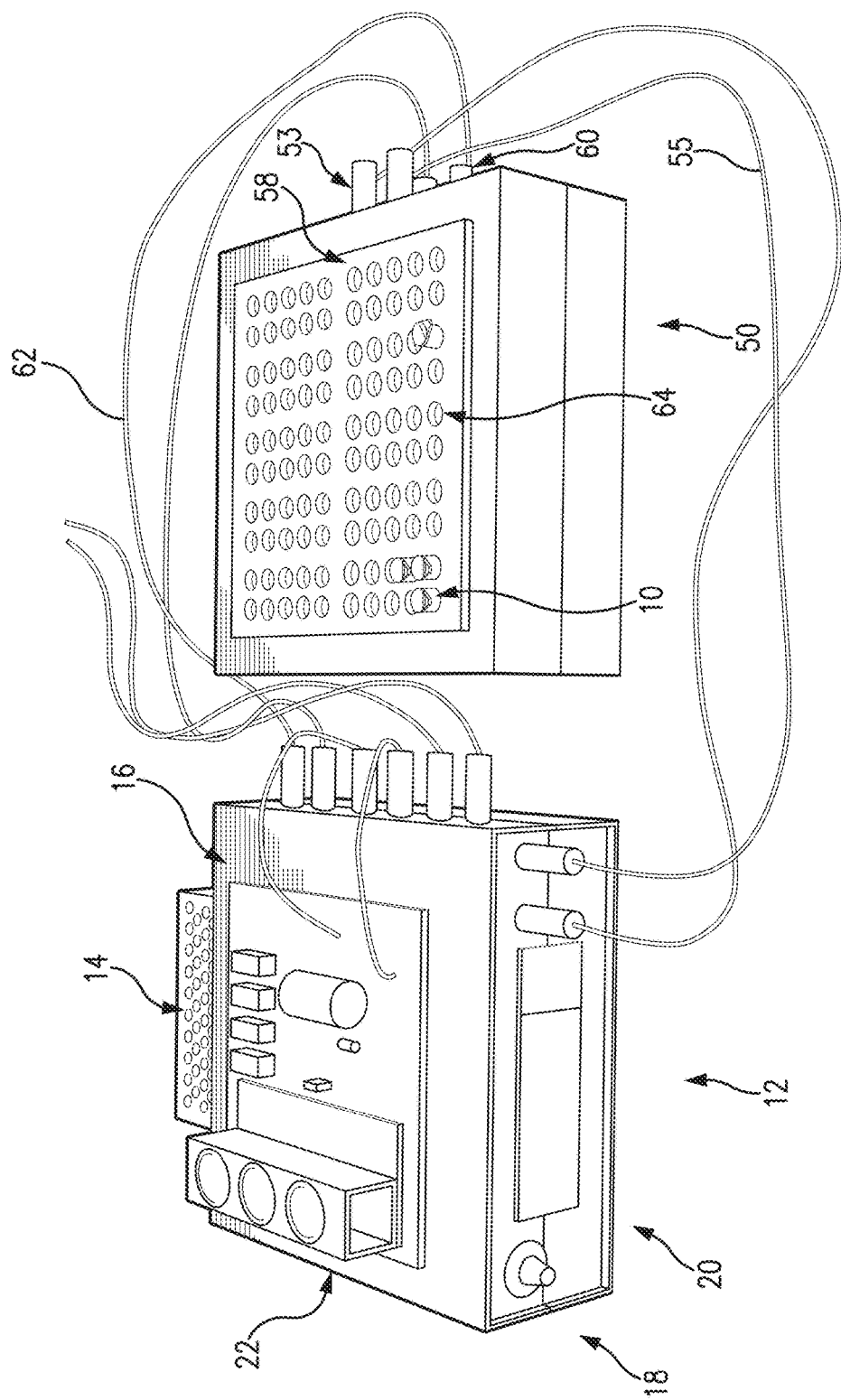
FIG. 1 is a top perspective view of a device for ligating nucleic acids according to a first example embodiment of the present invention, or for transforming cells with nucleic acids according to a second example embodiment of the present invention, showing the device holding vials containing the nucleic acids and/or cells and operably connected to a control unit.

Before the present compounds, compositions, articles, devices, and/or methods are disclosed and described, it is to be understood that the aspects described below are not limited to specific compounds, synthetic methods, or uses as such may, of course, vary. It is also to be understood that the terminology used herein is for the purpose of describing particular aspects only and is not intended to be limiting.

In this specification and in the claims that follow, reference will be made to a number of terms that shall be defined to have the following meanings:

The singular forms "a," "an" and "the" include plural referents unless the context clearly dictates otherwise. Thus, for example, reference to "a ligase" includes mixtures of two or more such enzymes, and the like.

"Optional" or "optionally" means that the subsequently described event or circumstance can or cannot occur, and that the description includes instances where the event or circumstance occurs and instances where it does not. For example, the phrase "optionally includes a gene for a selective marker" means that the gene may or may not be present.

Ranges may be expressed herein as from "about" one particular value and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint and independently of the other endpoint.

Disclosed are materials and components that can be used for, can be used in conjunction with, can be used in preparation for, or are products of the disclosed compositions and methods. These and other materials are disclosed herein, and it is understood that when combinations, subsets, interactions, groups, etc. of these materials are disclosed that while specific reference of each various individual and collective combination and permutation of these compounds may not be explicitly disclosed, each is specifically contemplated and described herein. For example, if an electromagnetic technique for DNA ligation is disclosed and discussed and a number of different compatible magnetic field strengths are discussed, each and every combination and permutation of ligation technique and magnetic field strength that is possible is specifically contemplated unless specifically indicated to the contrary. For example, if a class of molecules A, B, and C are disclosed as well as a class of molecules D, E, and F, and an example of a combination molecule, A-D is disclosed, then even if each is not individually recited, each is individually and collectively contemplated. Thus, in this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E is specifically contemplated and should be considered disclosed from disclosure of A, B, and C; D, E, and F; and the example combination A-D. This concept applies to all aspects of this disclosure including, but not limited to, steps in methods of making and using the disclosed compositions. Thus, If a variety of additional steps can be performed, it is understood that each of these additional steps can be performed with any specific embodiment or combination of embodiments of the disclosed methods, and that each such combination is specifically contemplated and should be considered disclosed.

References in the specification and concluding claims to parts by weight, of a particular element or component in a composition or article, denote the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent of a component, unless specifically stated to the contrary, is based on the total weight of the formulation or composition in which the component is included.

The term "mini-current" when used in reference to magnetic fields means that the current through the magnetic-field-inducing circuit is sufficiently small in magnitude that the ligation or transformation process is substantially thermal-free but sufficiently large in magnitude that a magnetic field is induced that drives the ligation or transformation process as intended.

The term "thermal-free" when used in reference to the devices and methods disclosed herein means that any heat generated by the magnetic-field-inducing circuit is so small in magnitude and/or is generated so far a distance away from the nucleic acids and/or cells being processed that it has substantially no material impact on the ligation or transformation process. For example, a temperature difference (e.g., between the sample being processed and a mini-current conductor uniformly positioned relative to each other and uniformly spaced apart by about 0.35 cm at their nearest points) during the ligation or transformation process of as much as about 3.7° C., which during testing has been shown to not materially impact the ligation or transformation processes, is considered to be thermal-free. And in one embodiment, the nucleic acids are ligated in the device from 25° C. to 30° C., which during testing has been shown to not materially impact the ligation process, and is considered to be thermal-free. In another embodiment, the cells are transformed with exogenous nucleic acids from 25° C. to 30° C., which during testing has been shown to not materially impact the transformation process, and is considered to be thermal-free. Thus, "thermal-free" does not mean that absolutely no heat is generated or that the sample being processed is subjected to absolutely no heat; rather, it means that any such heat has no more than a negligible effect on the quantity and quality of the resultant ligated nucleic acid or transformed cells.

"Heterologous" and "exogenous" genes and proteins are genes and proteins that have been experimentally put into a cell that are not normally expressed by that cell. An exogenous gene can optionally be cloned or derived from a different cell type or species than the recipient cell or organism. Exogenous genes may be introduced into cells by transduction or transformation.

An "isolated" nucleic acid is one that has been separated from other nucleic acid molecules and/or cellular material (peptides, proteins, lipids, saccharides, and the like) normally present in the natural source of the nucleic acid. An "isolated" nucleic acid may optionally be free of the flanking sequences found on either side of the nucleic acid as it naturally occurs. An isolated nucleic acid can be naturally occurring, can be chemically synthesized, or can be a cDNA molecule (i.e., is synthesized from an mRNA template using reverse transcriptase and DNA polymerase enzymes). A "nucleic acid fragment" is a linear segment of nucleic acid that must be inserted into an expression vector prior to being taken up by a cell. Several nucleic acid fragments may be ligated together to form an insert that is then ligated into a vector.

"Transformation" or "transfection" as used herein refers to a process for introducing heterologous DNA into a host cell. Transformation can occur under natural conditions or may be induced using various methods known in the art. Many methods for transformation are known in the art and include, for example, viral infection, electroporation, lipofection, chemical transformation, and particle bombardment. Cells may be stably transformed (i.e., the heterologous DNA is capable of replicating as an autonomous plasmid or as part of the host chromosome) or may be transiently transformed (i.e., the heterologous DNA is expressed only for a limited period of time).

"Competent cells" refers to microbial cells capable of taking up heterologous DNA. Competent cells can be purchased from a commercial source, or cells can be made competent using procedures known in the art. Exemplary procedures for producing competent cells are provided in the Examples.

I. Devices

Described herein are devices for ligating nucleic acids and/or transforming cells with exogenous nucleic acids. The devices are operable to induce a mini-current magnetic field and subject nucleic acids to the magnetic field to thereby ligate the nucleic acids by an electromagnetic process. The devices are also operable to induce a mini-current magnetic field and subject cells and exogenous nucleic acids to the magnetic field to thereby transform the cells with the exogenous nucleic acids by an electromagnetic process. The device of typical embodiments amplifies the nucleic acids or transforms the cells by the application of the magnetic field, not by applying heat, so the process is thermal-free. The device of other embodiments amplifies the nucleic acids or transforms the cells by the application of the magnetic field and also by applying heat (e.g., from heating elements), for a combination of a magnetic-field process and a thermal process. The result is that the desired ligation or transformation can be accomplished in significantly reduced time.

Turning now to the drawings, FIGS. 1-11 show a device 50 for ligating nucleic acids according to a first example embodiment of the present invention or for transforming cells according to a second example embodiment of the present invention. The amplification device 50 is a used with a control unit 12 and vials 10 of samples such as those depicted.

Figure 2:
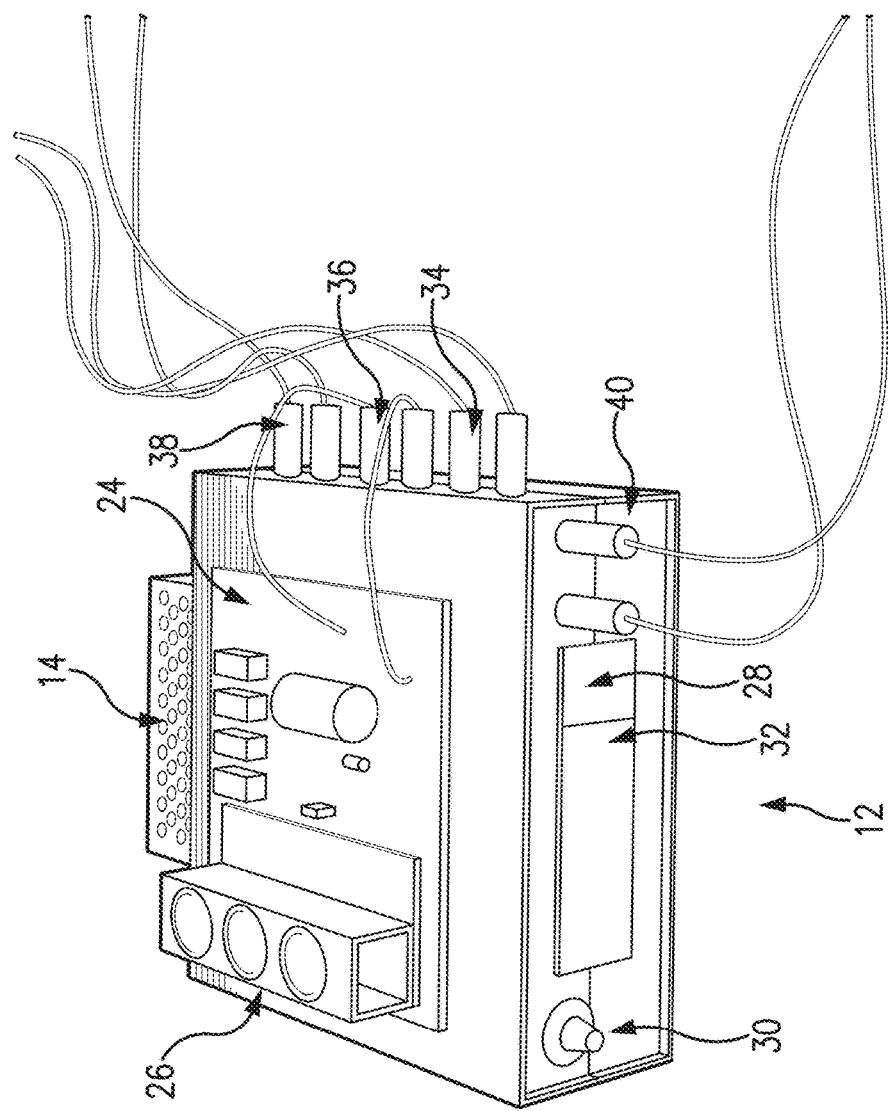
FIG. 2 is a top perspective view of the device of FIG. 1.
Figure 7:
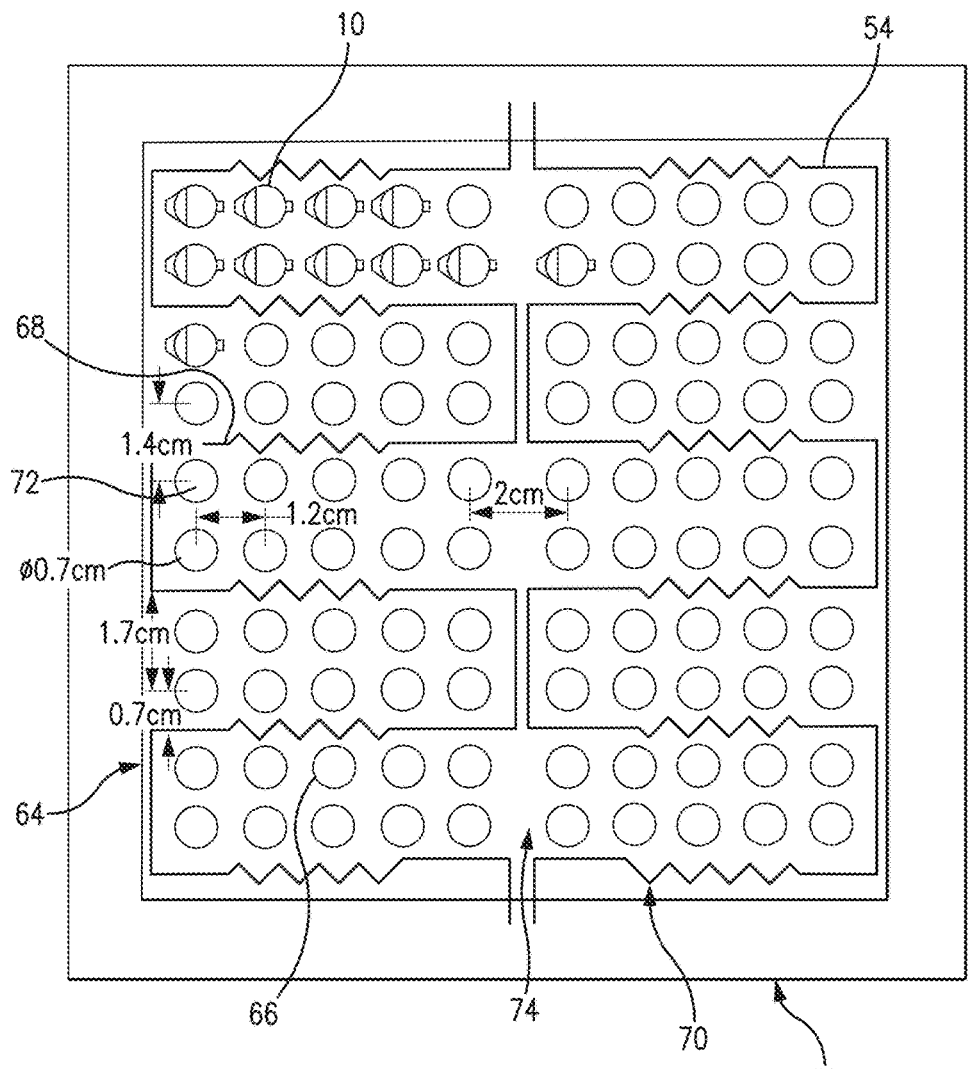
FIG. 7 is a top plan view the device of FIG. 1.
Figure 7A:
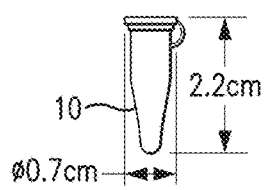
FIG. 7A is a side plan view of an example one of the vials used with the device of FIG. 1.

Referring with particularity to FIGS. 1-2 and FIG. 7A, the vials 10 can be of conventional types, made of conventional materials, and provided in standard sizes, and are sometimes synonymously referred to as tubes. For example, the vials 10 typically have volumes of 0.2 mL, 0.6 mL, 1.0 mL, 1.5 mL or 2.0 mL. The wall thickness of the sample vials 10 can be selected in order to maximize magnetic field distribution. For example, the vials 10 typically have sidewall thicknesses of 0.5 mm to 1.5 mm, preferably 1.15 mm to 1.20 mm, and more preferably 1.17 mm. It will be understood that the term "vial" is used herein broadly to include any container capable of holding samples for processing by any of the devices described herein and similar devices. In embodiments in which the vials are not tubular, corresponding modifications can be made to a support for the vials.

The control unit 12 can be of a conventional type known in the art, such as those commercially available from MCP (Shanghai MCP Corp. of Shanghai, China) including programmable power supply model M10-SPP1203. The control unit 12 includes a power supply 14, control circuitry and/or a programmed processor 16, one or more control inputs 18, and one or more control outputs 20, all assembled into a control housing 22. The power supply 12 can include transformers for stepping down delivered voltages (typically 110V) to the operating voltage of the device 50, which in typical commercial embodiments is 12V. Alternatively, the power supply 12 can provide other operating voltages and/or include conventional batteries. The control circuitry and/or programmed processor 16 can include a source power card management system 24 with power transistors 26, as depicted, designed to control the power delivered to the device. Alternatively, the control circuitry and/or programmed processor 16 can include other conventional control systems as are well known in the art. The control inputs 18 can include a keyboard 28 and knob 30, as depicted, and/or another conventional input such as a touchscreen or pushbuttons. The control outputs 20 can include a display screen 32, as depicted, and/or another conventional output such as an alarm sound or light generator. And the control housing 22 is sized to house (internally and/or externally) all these components and typically made of a metal or other appropriately strong and durable material. In addition, the control unit 12 can include input connectors 34 for the input power, output connectors 36 for connection to the power supply 14, output connectors 38 for connection to cooling system input connectors 60 of the device 50, and output connectors 40 for connection to power input connector 53 of the device. As such, the control system 12 of the depicted and other typical embodiments can be made of conventional components selected, configured, and interconnected by a person of ordinary skill in the art to produce the functionality described herein.

Figure 3:
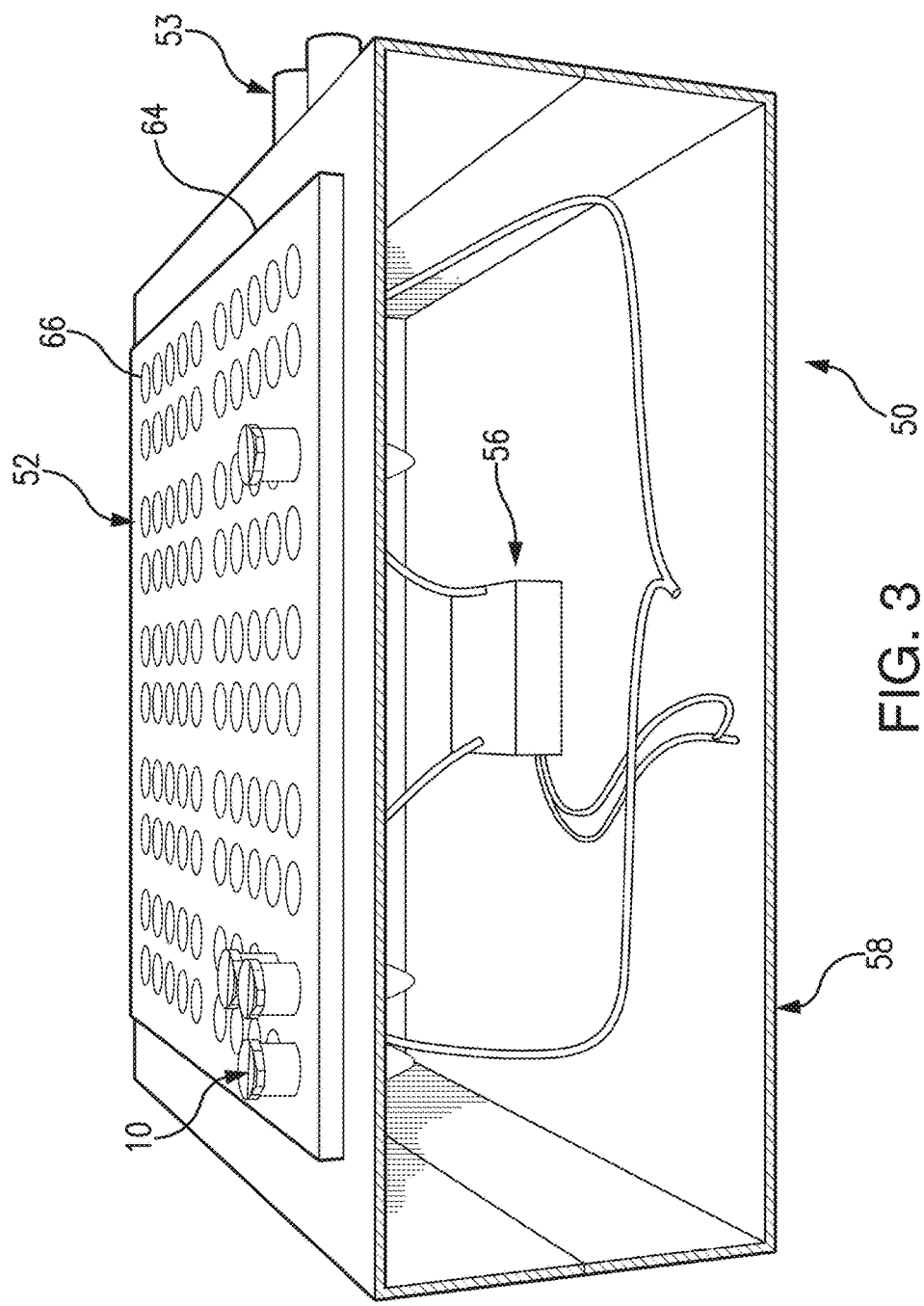
FIG. 3 is a top perspective view of the device of FIG. 2, with the front panel of its housing removed to show the internal components.
Figure 4:
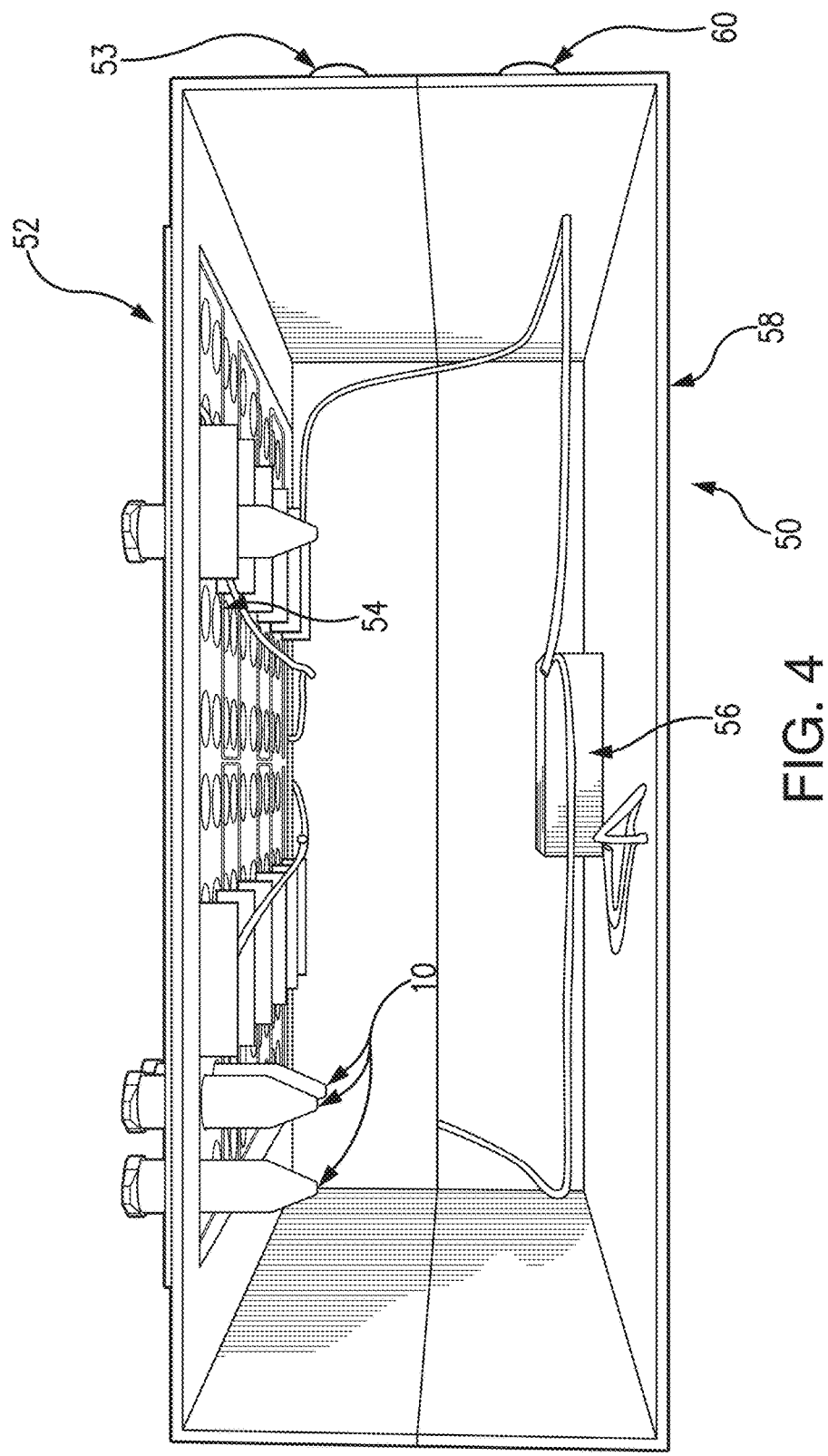
FIG. 4 is a front perspective view of the device of FIG. 3.
Figure 5:
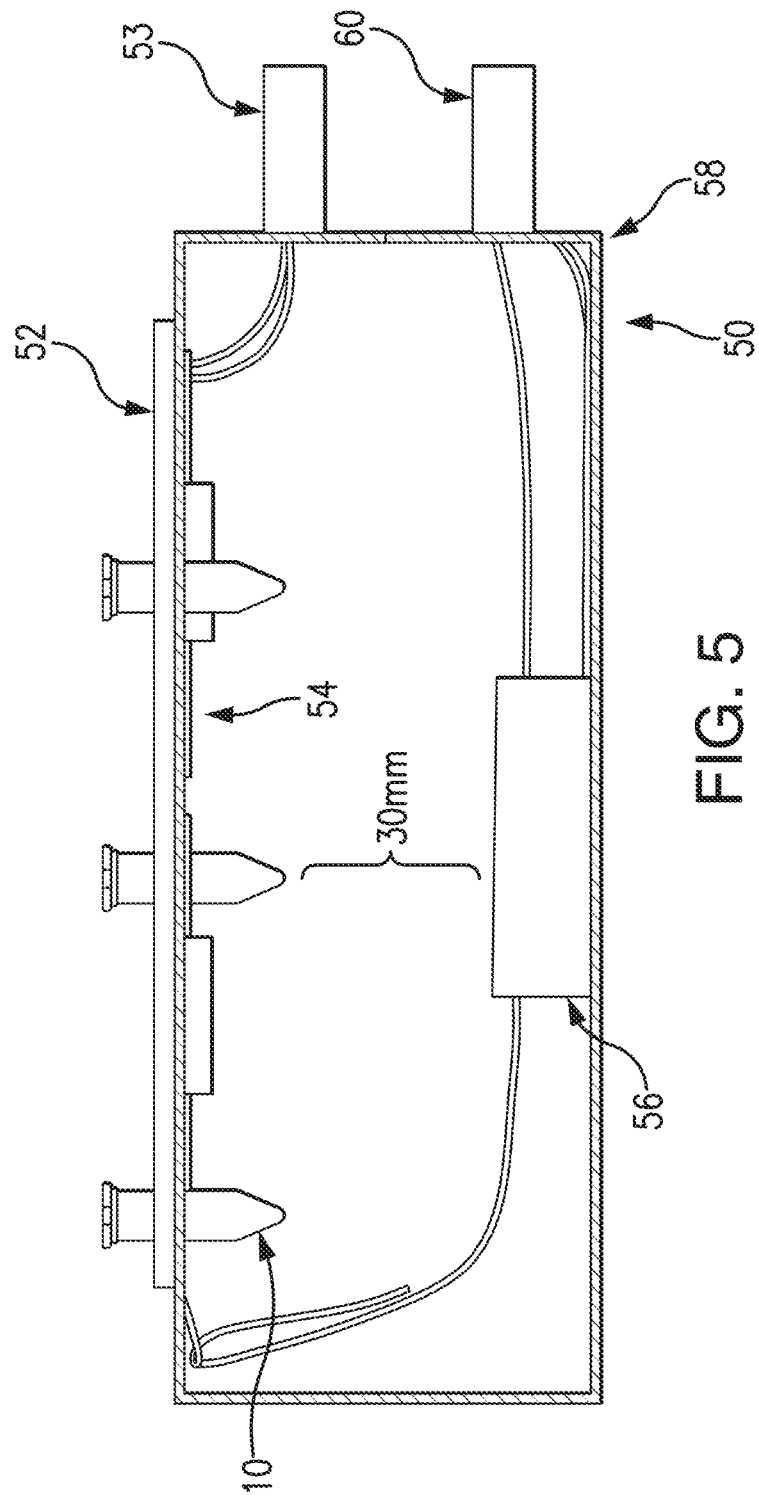
FIG. 5 is a front view of the device of FIG. 3.
Figure 6:
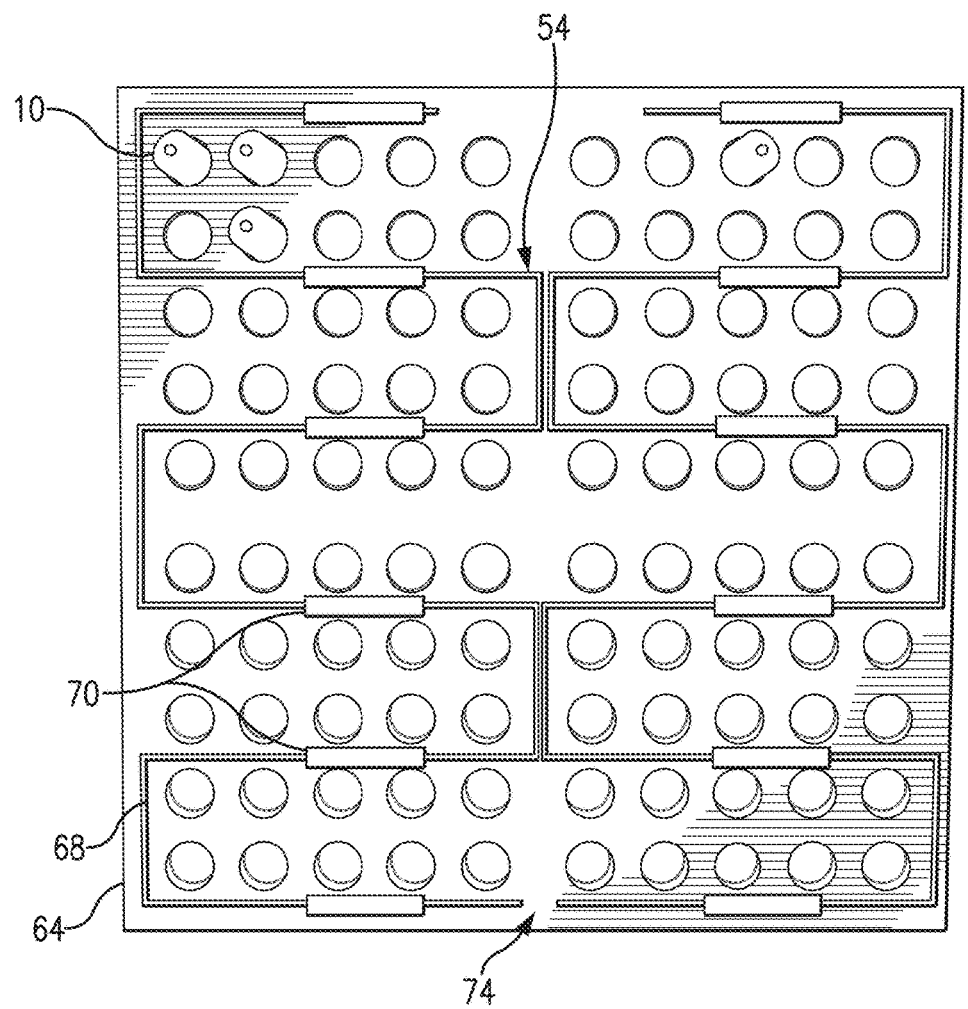
FIG. 6 is a bottom-side plan view of a vial-support plate with a magnetic-field-inducing circuit of the device of FIG. 1.

Referring now with particularity to FIGS. 3-5, the device 50 includes a vial support 52 and a circuit 54 that induces an electromagnetic field. In addition, the device 50 typically includes a cooling system 56 as well as a housing 58 for all of these components.

The housing 58 can be composed of any material selected for sufficient strength and durability including, but not limited to, low-density polyethylene, another plastic, rubber, glass, mixed glass (e.g., such as that sold under the PLEXIGLAS brand), acrylic, polycarbonate, and composite thereof. In some embodiments the housing 58 is not included and instead the vial support 52 includes legs or other base structures for elevating and providing clearance for the vials 10 held by it. And in other embodiments, the housing 58 is provided by a structure that elevates and provides clearance for the vials 10 but does not actually house or enclose any components, and instead is open to allow any heat generated by the process to escape more freely and not materially impact the thermal-free ligation or transformation processes. For example, the housing 58 can be in the form of an open or lattice frame, an X- or H-frame, or simply four support legs or two opposing support panels extending downward from the vial support 52. In some embodiments such as that depicted, the housing 58 includes a bottom wall and a peripheral sidewall (e.g., made of four sidewall panels), with a top wall formed at least in part by the vial support 52. In embodiments such as this, the housing 58 does not enclose or circumscribe the vials 10 in their entirety, only their portions below the vial support 52. In typical embodiments, power input connectors 53 are provided for connection to power output connectors 40 of the control unit 12 by power wires 55 (see FIG. 1).

The cooling system 56 typically includes a conventional cooling fan positioned for example generally centrally within the housing 58. The fan 56 can be of a conventional type known in the art, such as that commercially available from Cooler Master Co., Ltd. (Chung Ho City, Taiwan) under the SICKLEFLOW brand. The fan 56 is wired to cooling system input connectors 60 on the housing 58, which connectors provide for connection to output connectors 38 of the control unit 12 by fan wires 62 for power and control (see FIGS. 1-2). In use, the cooling system 56 can be set at a desired temperature (e.g., 25° C. to 26° C.) so that it will automatically turn on and off to maintain the pre-set constant temperature in the housing 58 for the duration of the ligation and/or transformation processes. As such, the cooling system 56 can include automatic controls including conventional temperature sensors such thermocouples.

In some embodiments, the cooling system 56 is not provided because the magnetic-field-inducing circuit 54 generates such little heat that the samples in the vials 10 are not heated by it at all (or at least they're heated so little that this has no material impact on the ligation and/or transformation processes). And the motor of the fan 56 generates such little heat that the samples in the vials 10 are not heated by it at all (or at least they're heated so little that this has no material impact on the ligation and/or transformation processes). To ensure this thermal-free operation, the fan 56 can be spaced apart from the vials 10 far enough that any heat from the fan motor does not reach the vials but close enough that the fan still moves air across the vials. In the depicted embodiment, for example, the fan is spaced about 30 mm from the circuit 54.

The vial support 52 typically includes a plate 64 with an array of holes 66 formed in it. In the depicted embodiment, the holes 66 are circular with an about 0.7 cm diameter for holding vials 10 with a 0.7 cm diameter. The holes 66 are typically spaced uniformly in each direction so that the magnetic field generated by the circuit 54 is uniformly applied to all of the vials. In the depicted embodiment, the vial-support plate 64 includes 100 of the holes 66 in a 10×10 array, though more or fewer holes can be provided for any application as may be desired. The vial-support plate 64 can be made of any material selected for sufficient strength and durability including, but not limited to, Bakelite, another plastic, carbon-fiber materials, and composites thereof. In other embodiments, instead of a plate, the vial support 52 is provided by a frame such as a lattice, an array of hooks, eyes/loops, or other suspension elements, or another structure that defines an array of openings for the vials and supports them in position. And in embodiments in which the vials 10 are not tubular, the vial support 52 can be modified accordingly so that the holes 66 have a shape for holding the vials in place. As such, the holes 66 can be other than circumferential openings and instead can be provided by notches, slots, or other openings.

Referring now with particularity to FIGS. 4-9, the magnetic-field-inducing circuit 54 includes at least one conductor 68 through which a mini-current I is passed to induce a magnetic field B. In typical embodiments, the conductor 68 is provided by a copper wire, though other conductive materials can be used. The conductor 68 has terminals that are electrically connected for example by wiring to the power input connectors 53 on the housing 58, which connectors provide for connection to power output connectors 40 of the control unit 12 by power wires 55 for power and control (see FIGS. 1-2).

For typical commercial embodiments, examples of the approximate voltage of and mini-current I through the circuit 54, and the magnetic field B induced by the circuit 54 and applied to the samples, are shown in Tables 1 and 2. Each of the ranges between each of the listed approximate values is considered to represent a separate embodiment and mode of use. Note that the magnetic field B is the strength of the magnetic field at and applied to the samples in the vials 10, which is necessarily less than the core magnetic field immediately adjacent the conductor 68 inducing it due to the distance spacing "d" between the conductor and the vial centers. And note that the distance d refers to the conductor-to-vial-centerline spacing, however, this spacing and the conductor-to-sample spacing (where an outer-most portion of the sample is first exposed to the effect of the magnetic field) in some embodiments can be considered to be substantially the same due to the relatively small diameter of the vials 10 and the fluid dynamics of the samples in the vials. In other embodiments, however, the diameter of the vials 10 (or tubes or other sample-holding containers) relative to the vial-centerline spacing from the magnetic-field-inducing conductor 68 is relatively large, and the samples in the vials have relative fluid dynamics, such that the induced magnetic field is adjusted to account for the fact that certain portions of the samples in the vials are much closer to the conductor.

In Table 1, the voltage and current I were varied to produce various magnetic fields B on the samples to assess the resulting ligation and transformation processes. And in Table 2, the voltage and resistance were varied to produce the same current I and magnetic field B on the samples to assess different design and construction options. In both Tables, the distance "d" is 7 mm.

TABLE 1

| Working Voltage (VDC) | Mini-Current I (Amps) | Magnetic Field B (Gauss) |
|---|---|---|
| 0.01 | 0.005 | 0.001 |
| 0.05 | 0.025 | 0.009 |
| 0.1 | 0.05 | 0.019 |
| 0.2 | 0.10 | 0.039 |
| 0.3 | 0.15 | 0.059 |
| 0.4 | 0.20 | 0.080 |
| 0.5 | 0.25 | 0.100 |
| 0.6 | 0.30 | 0.120 |
| 0.7 | 0.35 | 0.141 |
| 0.8 | 0.40 | 0.161 |
| 0.9 | 0.45 | 0.180 |
| 1.0 | 0.50 | 0.200 |
| 1.2 | 0.60 | 0.241 |
| 1.4 | 0.70 | 0.282 |
| 1.5 | 0.80 | 0.322 |
| 1.8 | 0.90 | 0.360 |
| 2.0 | 0.90 | 0.360 |
| 2.0 | 1.00 | 0.402 |

TABLE 2

| Working Voltage (VDC) | Mini-Current I (Amps) | Resistance (Ohms) | Magnetic Field B (Gauss) |
|---|---|---|---|
| 0.5 | 0.9 | 0.56 | 0.36 |
| 1.0 | 0.9 | 1.11 | 0.36 |
| 1.5 | 0.9 | 1.67 | 0.36 |
| 2.0 | 0.9 | 2.22 | 0.36 |
| 2.5 | 0.9 | 2.78 | 0.36 |
| 3.0 | 0.9 | 3.33 | 0.36 |
| 3.5 | 0.9 | 3.89 | 0.36 |
| 4.0 | 0.9 | 4.44 | 0.36 |
| 4.5 | 0.9 | 5.0 | 0.36 |
| 5.0 | 0.9 | 5.56 | 0.36 |
| 5.5 | 0.9 | 6.11 | 0.36 |
| 6.0 | 0.9 | 6.67 | 0.36 |
| 6.5 | 0.9 | 7.22 | 0.36 |
| 7.0 | 0.9 | 7.78 | 0.36 |
| 7.5 | 0.9 | 8.33 | 0.36 |
| 8.0 | 0.9 | 8.89 | 0.36 |
| 8.5 | 0.9 | 9.44 | 0.36 |
| 9.0 | 0.9 | 10.0 | 0.36 |
| 9.5 | 0.9 | 10.56 | 0.36 |
| 10.0 | 0.9 | 11.11 | 0.36 |
| 10.5 | 0.9 | 11.67 | 0.36 |
| 11.0 | 0.9 | 12.22 | 0.36 |
| 11.5 | 0.9 | 12.78 | 0.36 |
| 12.0 | 0.9 | 13.33 | 0.36 |

In a preferred embodiment, the device 50 is operated with good results at about 12V with a mini-current I of about 900 mA to induce a magnetic field B of about 0.35 to about 0.36 Gauss on the samples in the vials 10 holding them when the vials and the magnetic-field-inducing conductor 68 are uniformly positioned relative to each other and uniformly spaced apart by a distance d of, for example, about 0.7 cm (e.g., about 0.35 cm at their closest points for vials with a diameter of about 0.7 cm). In other preferred embodiments, the device 50 is operated with a mini-current I of about 800 mA to induce a magnetic field B of about 0.322 Gauss on the samples, with a mini-current I of about 1.0 A to induce a magnetic field B of about 0.402 Gauss on the samples, or with a mini-current I and a magnetic field B within the ranges defined by those approximate values.

It will be understood that the device 50 can be operated to induce a magnetic field B of higher or lower strengths on the samples to produce the intended results as described herein. In some embodiments, for example, the magnetic-field-inducing conductor 68 is spaced a different distance d (than the 0.7 cm spacing of the depicted embodiment) from the centerlines of the vials 10 holding the samples, and/or a current I of a different strength is passed through the conductor 68 (by using a different voltage and/or resistance), so that a magnetic field B of different strength is induced by the conductor and applied to the samples. Typically, for a decreased distance d and/or a stronger current I, a stronger magnetic field B is induced, and for an increased conductor-to-sample spacing and/or a weaker current, a weaker magnetic field is induced, to produce the desired ligation and/or transformation.

In other embodiments, a core magnetic field of a different strength is induced to apply the same-effect magnetic field B to the samples. For example, in some embodiments the magnetic-field-inducing conductor 68 is spaced a different distance d (than the 0.7 cm spacing of the depicted embodiment) from the vials 10 holding the samples, so a current I of a different strength is passed through the conductor 68 (by using a different voltage and/or resistance) in order to induce a core magnetic field of a different strength such that, given the different conductor-to-sample spacing, the magnetic field B at and applied to the samples is still in the same range of about 0.322 Gauss to about 0.402 Gauss. And in other embodiments, a current I of a different strength is passed through the conductor 68, so a core magnetic field of a different strength is induced, and in order for the magnetic field B at and applied to the samples to be still in the same preferred range of about 0.322 Gauss to about 0.402 Gauss, a different conductor-to-sample distance spacing d is used.

In order to determine the conductor-to-vial distance spacing d and the current I to provide a magnetic field B at and applied to the samples in for example the preferred range of about 0.322 Gauss to about 0.402 Gauss, the following formula (known as the "Biot and Savat" equation) is used:

$$B = \frac{Mo * I}{2\pi * d}$$

in which "Mo" is the magnetic permeability in empty space, a constant of $4\pi \times 10^{-7}$ and in which d and I are as defined herein. In embodiments such as this in which each sample in each vial 10 is affected by magnetic fields from two sides (see FIGS. 8-9), the magnetic fields can be calculated separately and then added together.

The magnetic-field-inducing circuit 54 typically includes a plurality of resistors 70 to set the voltage. The rating of the resistors 70 is selected to maintain the voltage at the desired pre-set level; a person of ordinary skill in the art can properly select the resistor ratings. The resistors 70 can be made of a carbon material with a low concentration of copper (for example, with a carbon-to-copper ratio of 80/20, 90/10, or 95/5), copper fiber, ferronickel, or other electric-resistive materials known in the art. In a typical commercial embodiment with a 10×10 array of holes 66 and the conductor 68 routed adjacent to and uniformly positioned relative to all of the holes and uniformly spaced apart about 0.35 cm at their closest points, the resistors 70 can have a resistance of about 1 ohm to about 5 ohms, with a resistance of about 1.5 ohms working well. This resistance is sufficiently small in magnitude that very little heat is generated by the mini-current I flowing through the resistors 70 such that the ligation and/or transformation process remains thermal-free. And to ensure that any heat from the resistors 70 does not materially impact the ligation and/or transformation process, the cooling system 56 can be operated to dissipate such heat.

In the depicted embodiment, the magnetic field B is induced simply by running the mini-current I through the conductor 68 of the circuit 54. In other embodiments, the circuit includes coiled wires to induce a concentrated magnetic field of a greater magnitude. And in still other embodiments, there are more or fewer resistors and/or additional circuit components are included, as persons of ordinary skill will understand and be capable of selecting to induce the desired magnetic field while maintaining the process as thermal-free.

Figure 8:
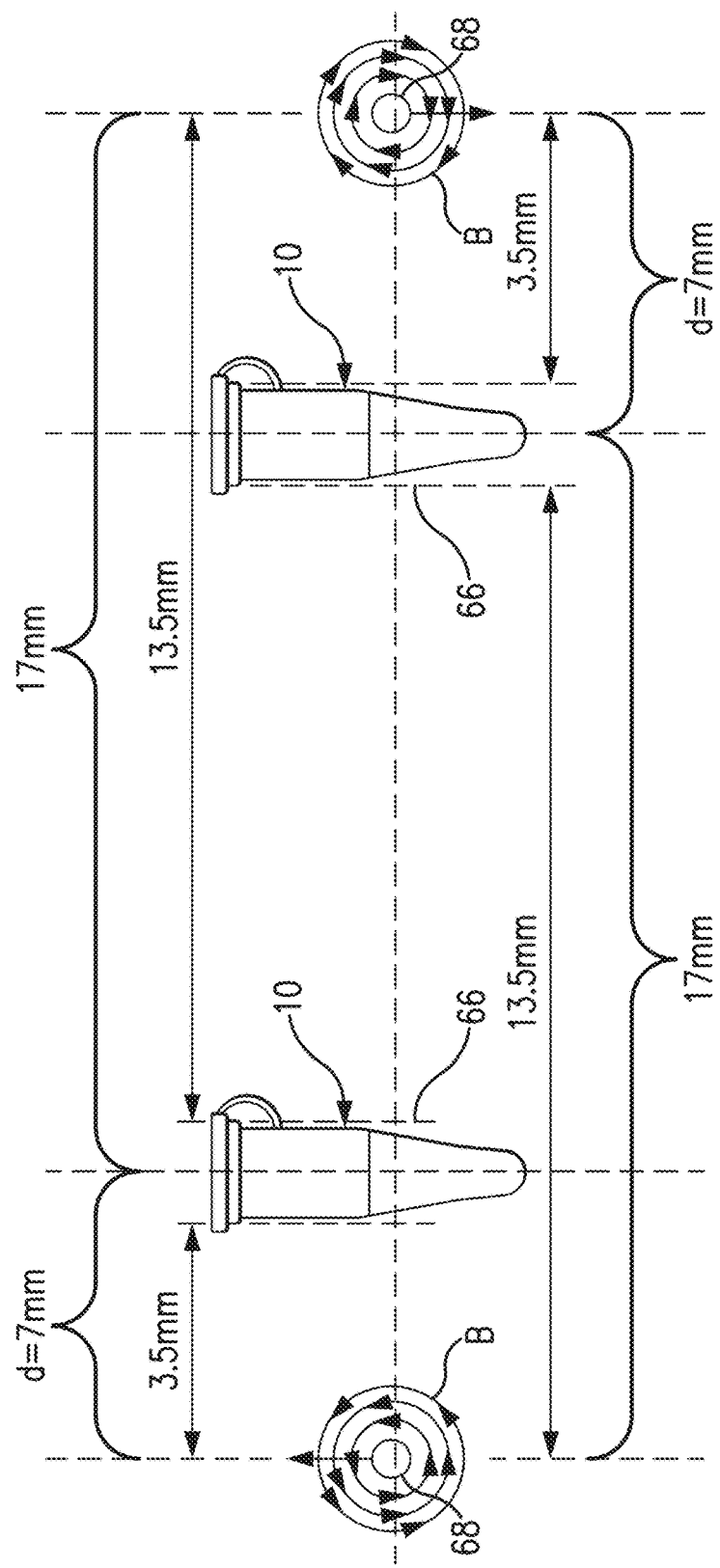
FIG. 8 is a side view depicting the relative positions of the vials held by the vial-support plate and the conductors of the magnetic-field-inducing circuit of the device of FIG. 1.
Figure 9:
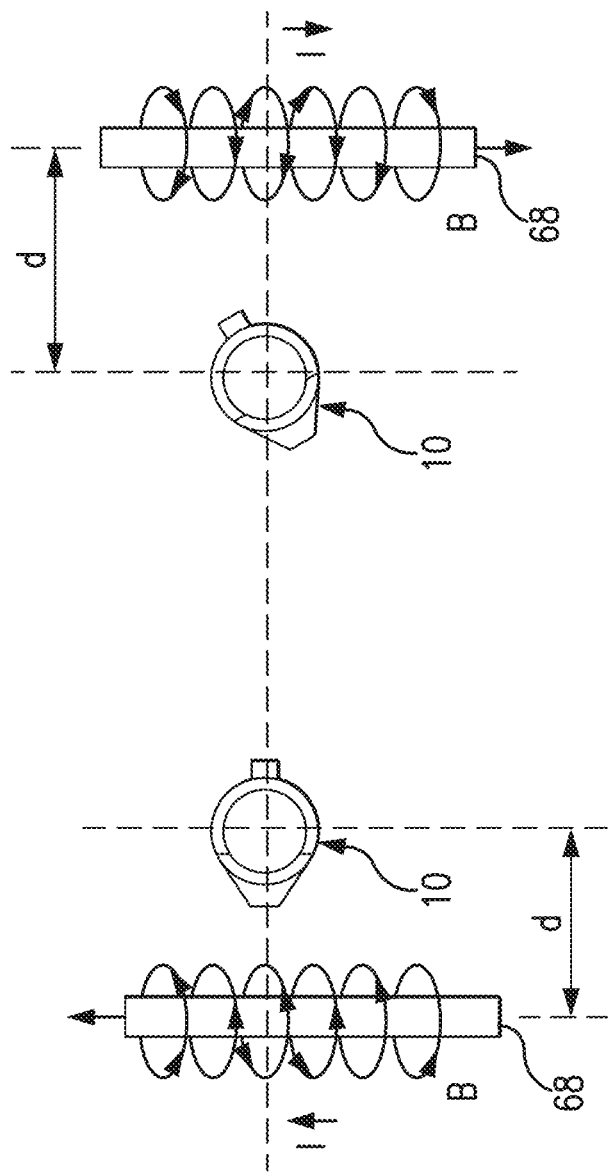
FIG. 9 is a plan view of the depiction of FIG. 8.

The conductor 68 is routed in a position equidistant from all of the holes 66 in the closest row so that each of the vials 10 is the same normal distance away the conductor. In this way, the magnetic field B generated by the circuit 54 is uniformly applied to the samples in all of the vials 10. In particular, the conductor 68 can be routed centrally between every other row of the holes 66 such that the centers 72 of all of the holes are the same normal distance from the conductor. For example, in the depicted embodiment the holes 66 of the vial-support 64 are uniformly spaced apart center-to-center in an array by 1.4 cm in one direction and by 1.2 cm in the perpendicular direction, with the conductor 68 routed midway between each row of the holes whose centers are spaced apart by 1.4 cm. So the conductor 68 is equidistantly positioned 0.7 cm away from the center of each of the holes 66 and equidistantly positioned 0.35 cm away from the holes 66 at the closest point. It should be noted that these and other dimensions shown in FIG. 8 are representative and included for illustration purposes only, and as such are not limiting of the invention.

The circuit 54 is typically mounted to the bottom side of the vial-supporting plate 64, as shown, for ease of manufacture. Alternatively, the circuit 54 can be positioned in another location so long as the magnetic field B is still uniformly applied to and equidistant from all the samples in the vials 10. For example, the conductor 68 can be attached to a mounting board with holes aligned with the holes 66, and the board can be vertically spaced from the vial-support 52 and positioned adjacent the bottoms of the vials to place the magnetic field B closer to the samples in the vials 10 while keeping the conductor 68 equidistant from all the samples in the vials. In other embodiments, the conductor 68 is embedded into or mounted atop the vial support 52. In the depicted embodiment, the conductor 68 is positioned in a plane that is parallel to the vial-supporting plate 64 and perpendicular to the vials 10. In other embodiments, the conductor 68 is positioned in a plane that is not parallel to the vial-supporting plate 64 and not perpendicular to the vials 10. And in other embodiments the circuit 54 includes multiple conductors 68 in multiple planes that are spaced apart from each other, for example, a first conductor in a first plane and a second conductor in a second plane that is spaced apart from the first plane. In the depicted embodiment, the circuit 54 actually includes two circuits. In such embodiments, the two conductors 68 can be routed between the same two holes 66 in some doubled places. To allow for the extra space needed for this while still maintaining the uniform hole-to-conductor spacing, the vial-supporting plate 64 can have a wider spacing area 74 between two rows of holes 66 to accommodate the doubled wire.

Figure 10:
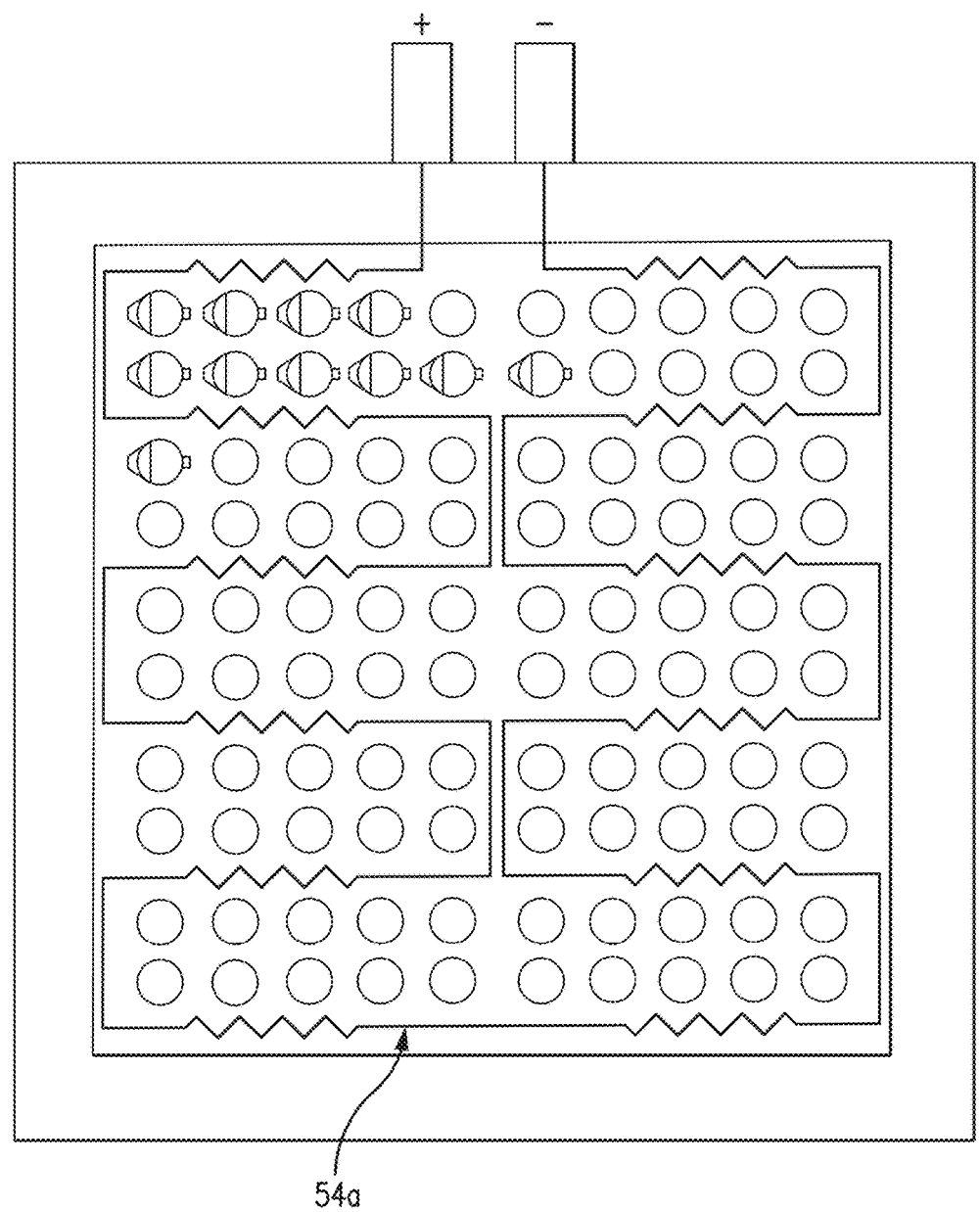
FIG. 10 is a bottom-side plan view of a vial-support plate with a magnetic-field-inducing circuit of the device according to a first alternative embodiment.
Figure 11:
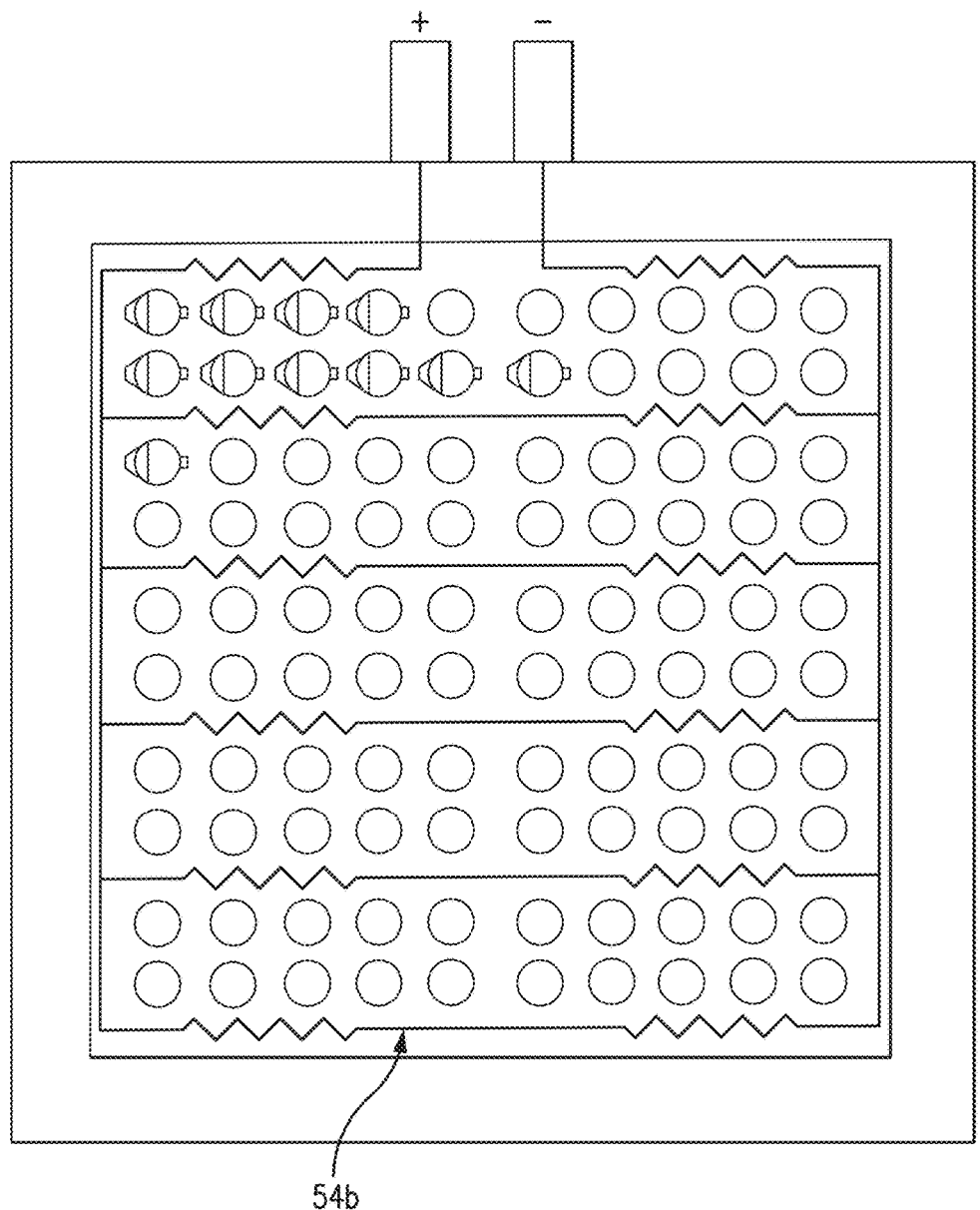
FIG. 11 is a bottom-side plan view of a vial-support plate with a magnetic-field-inducing circuit of the device according to a second alternative embodiment.
Figure 12A:
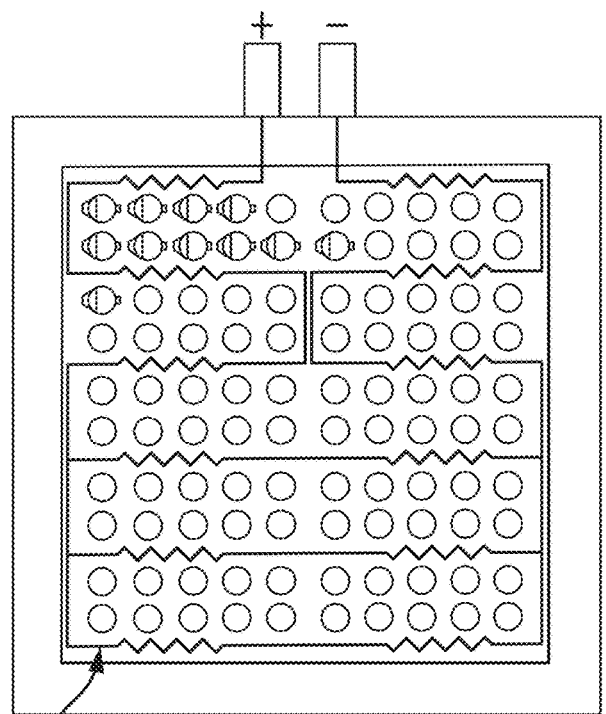
Figure 12B:
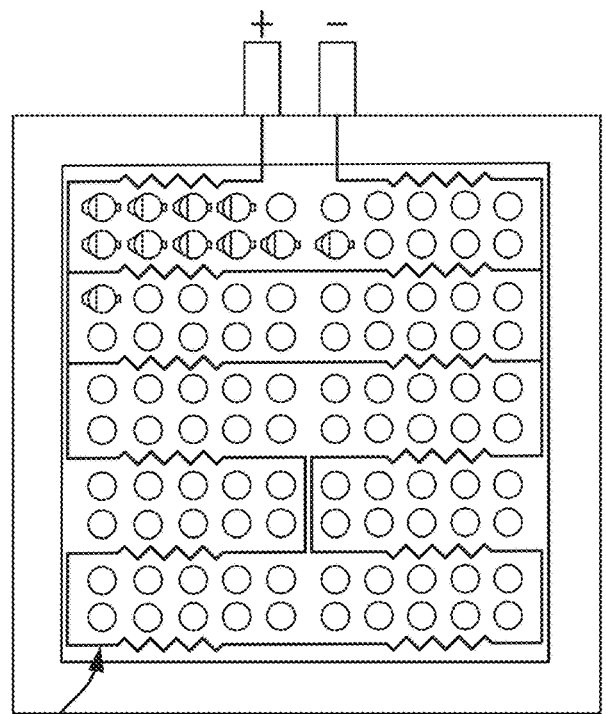
Figure 12E:
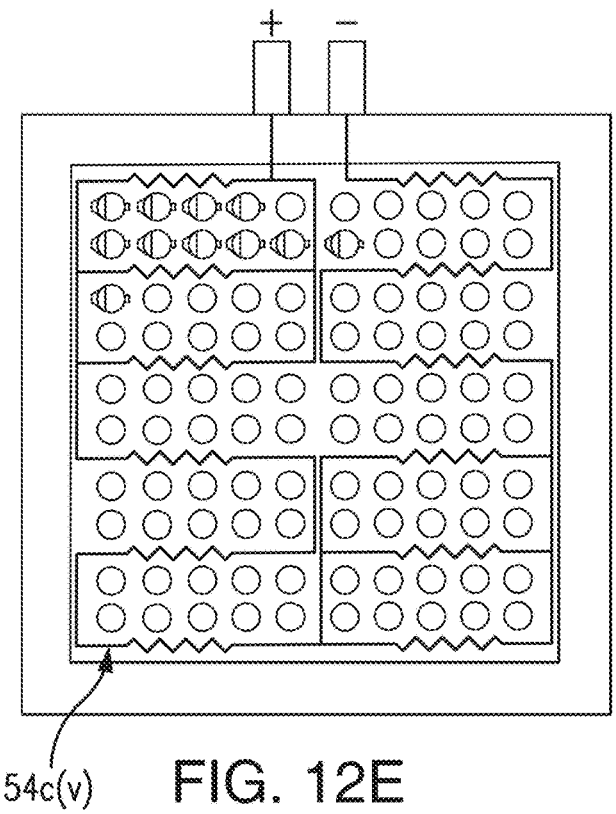
Figure 12F:
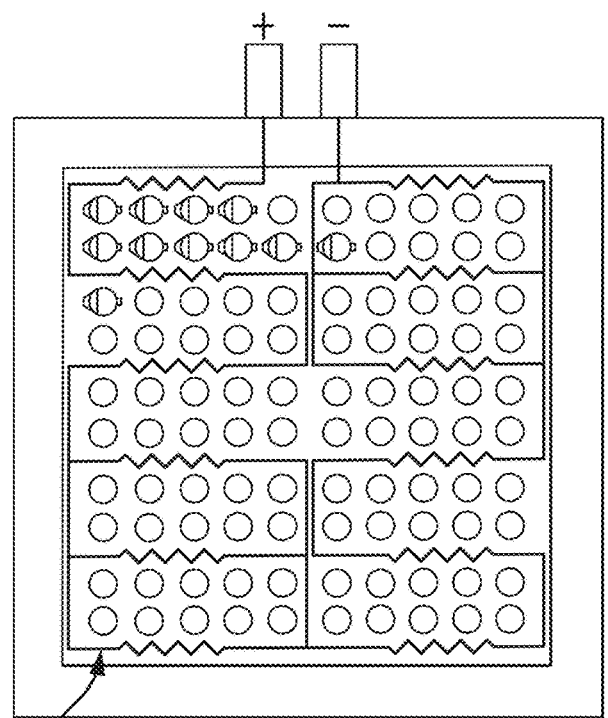
Figure 14:
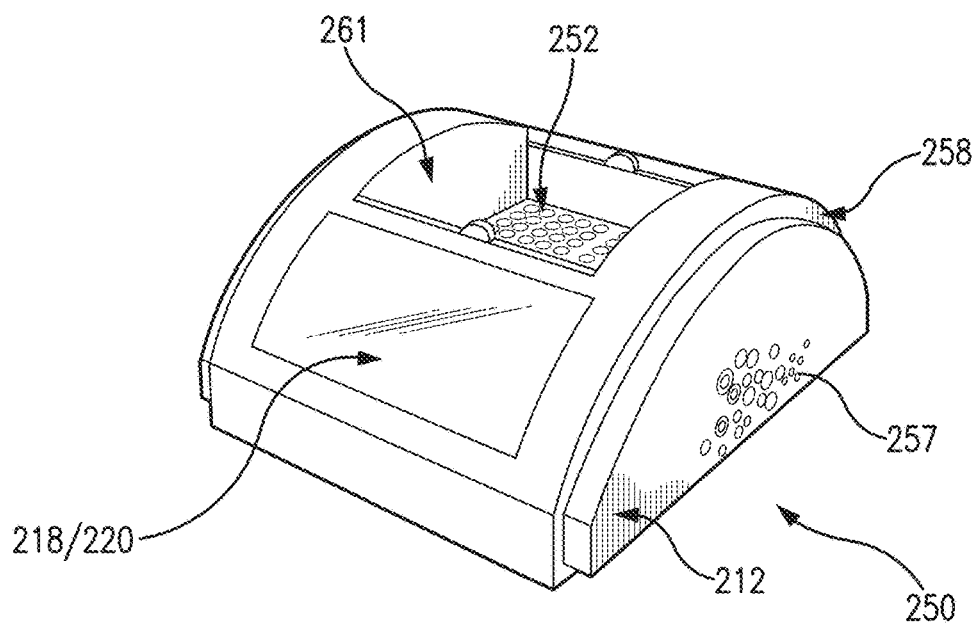
FIG. 14 is a perspective view of a device for ligating nucleic acids according to a fifth example embodiment of the present invention, or for transforming cells with nucleic acids according to a sixth example embodiment of the present invention, showing the access panels in an open position and an integral control unit.
Figure 15:
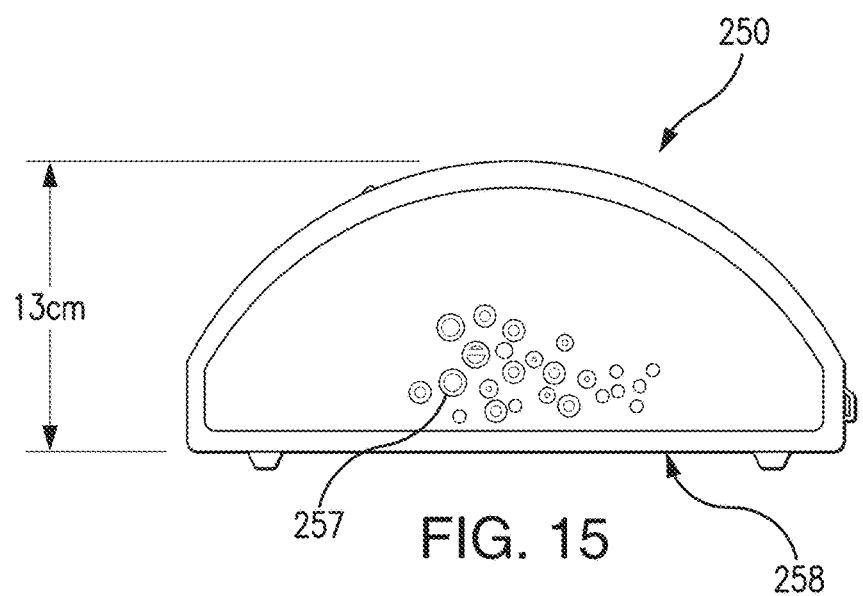
FIG. 15 is a right side view of the device of FIG. 14.
Figure 16:
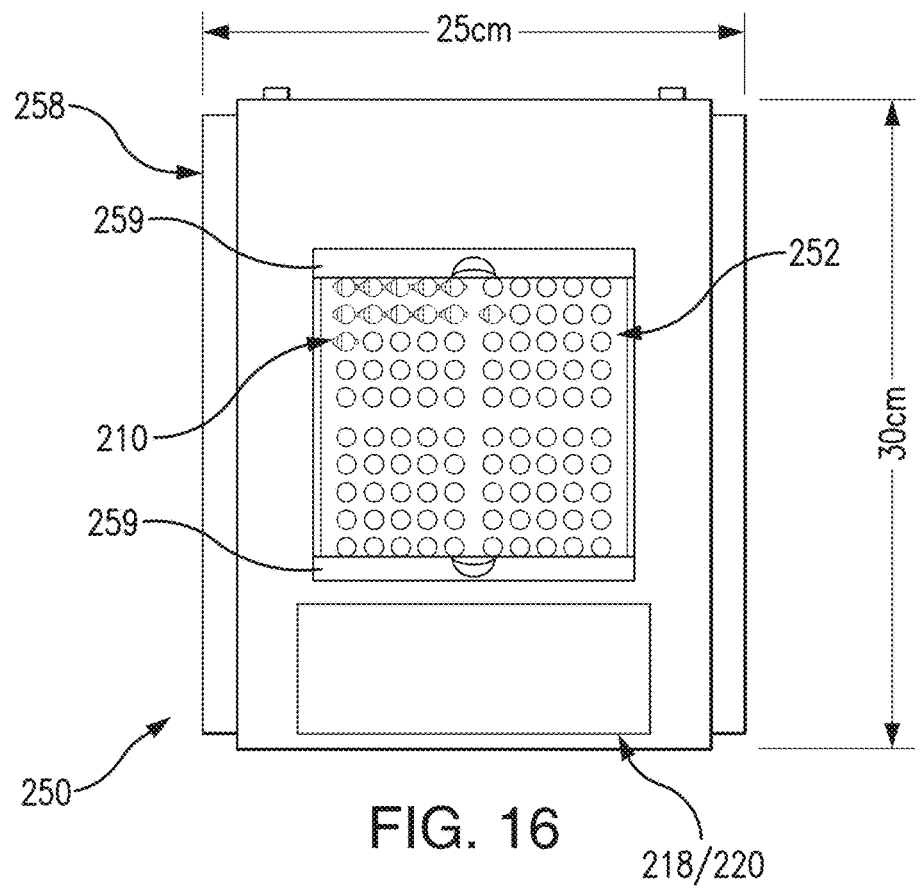
FIG. 16 is a top view of the device of FIG. 14.
Figure 17:
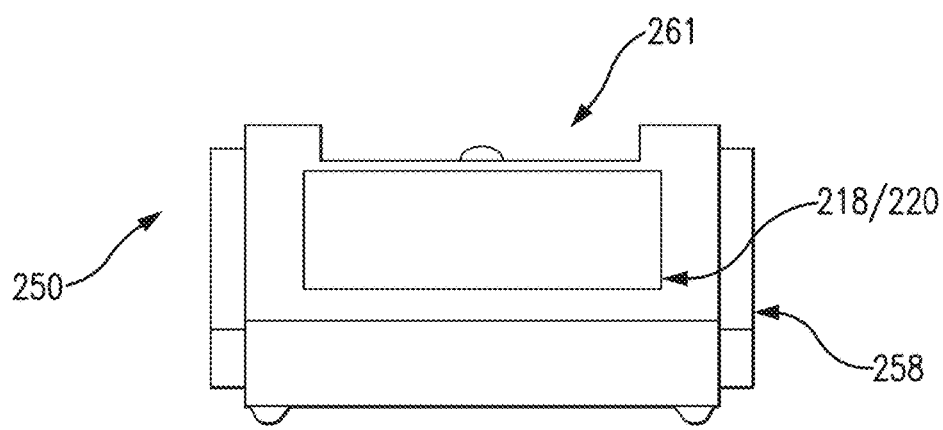
FIG. 17 is a front side view of the device of FIG. 14.
Figure 18:
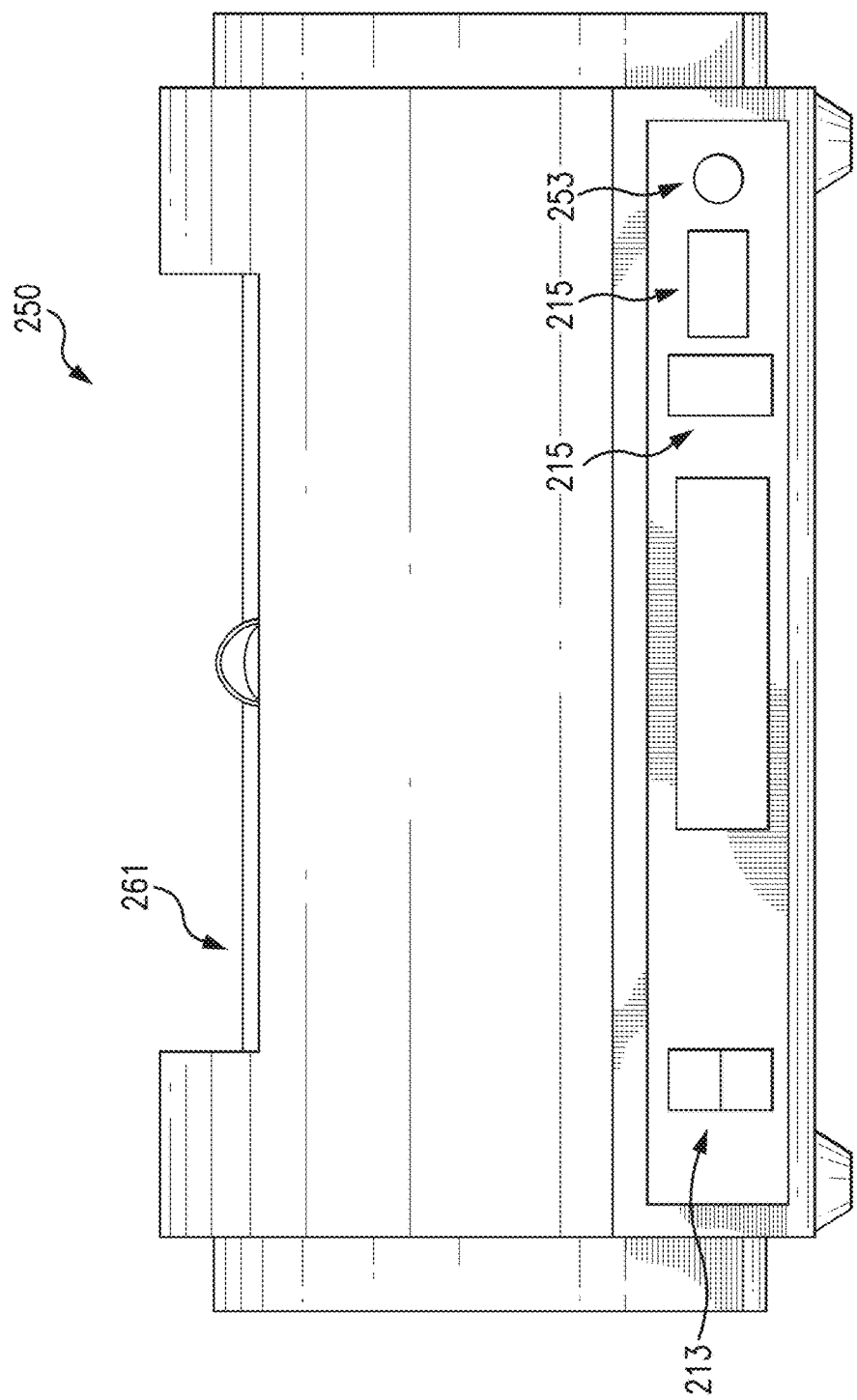
FIG. 18 is a rear side view of the device of FIG. 14.
Figure 19:
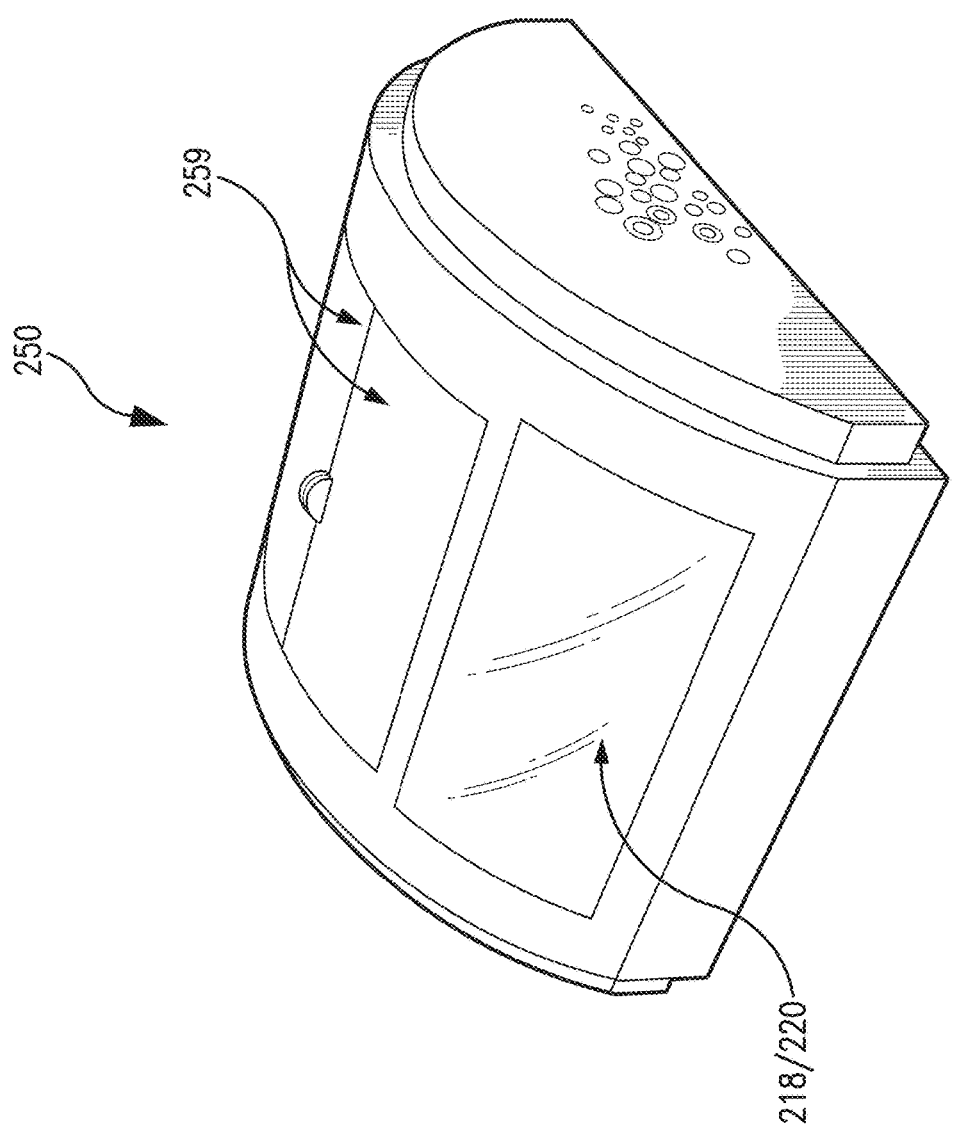
FIG. 19 shows the device of FIG. 14 with the access panels in a closed position.
Figure 20:
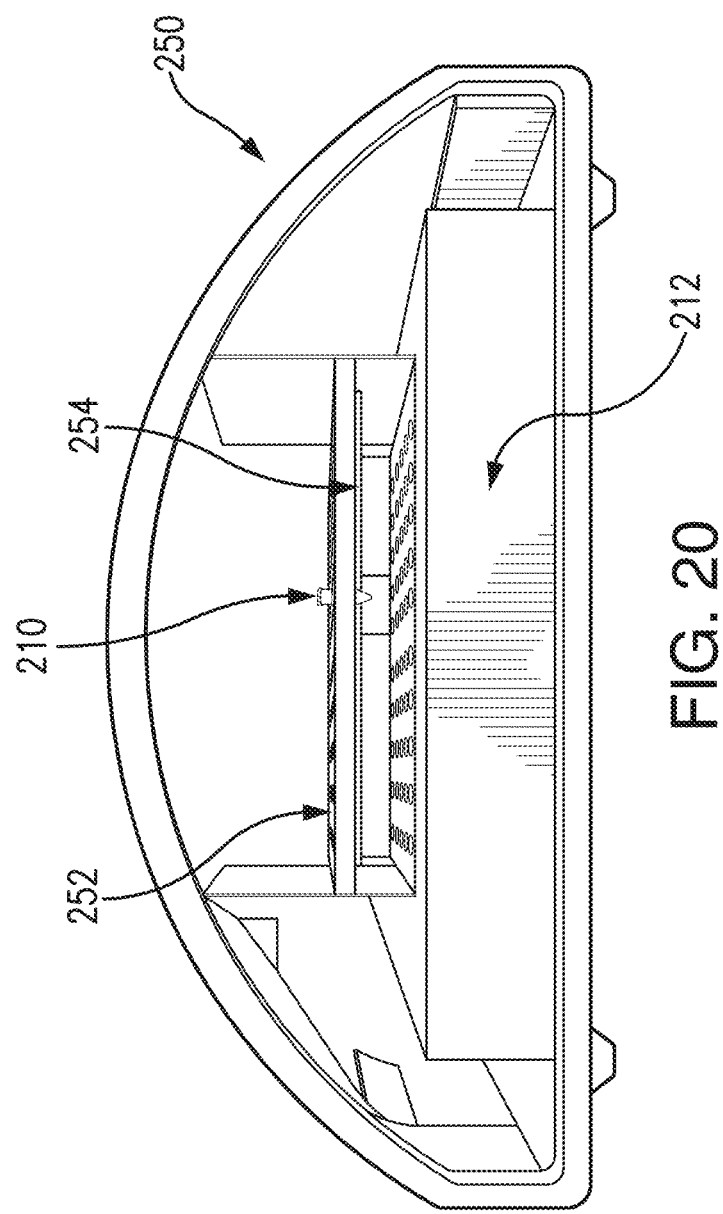
FIG. 20 shows the device of FIG. 15 with a portion of the housing removed to reveal the device's inner components.
Figure 21:
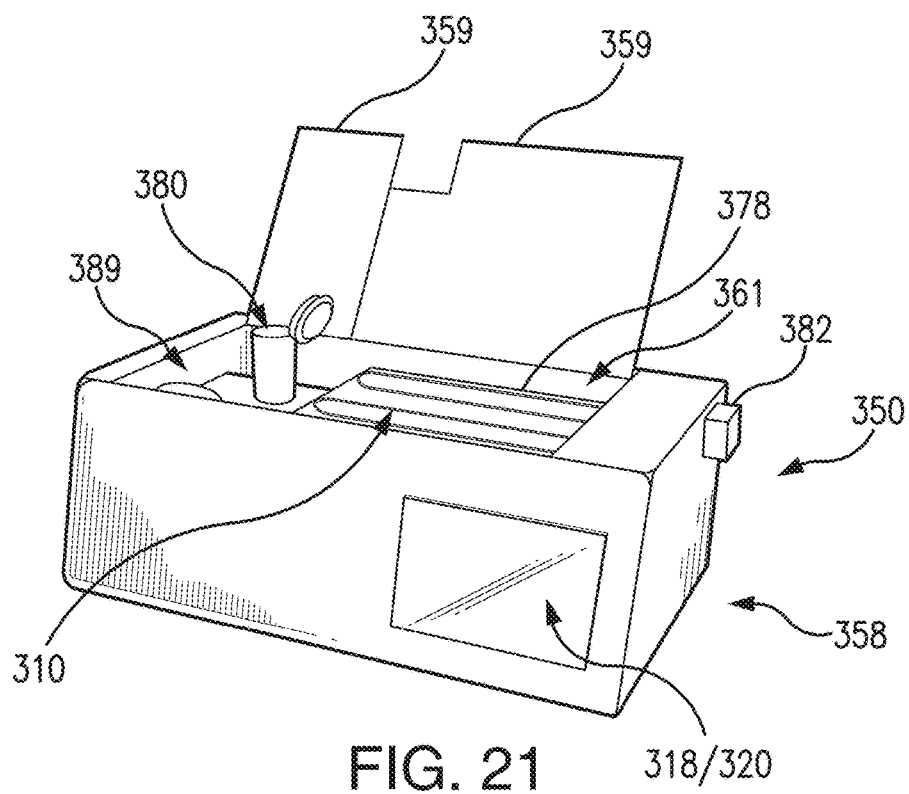
FIG. 21 is a perspective view of a device for ligating nucleic acids according to a seventh example embodiment of the present invention, or for transforming cells with nucleic acids according to an eighth example embodiment of the present invention, showing the access panels in an open position.
Figure 22:
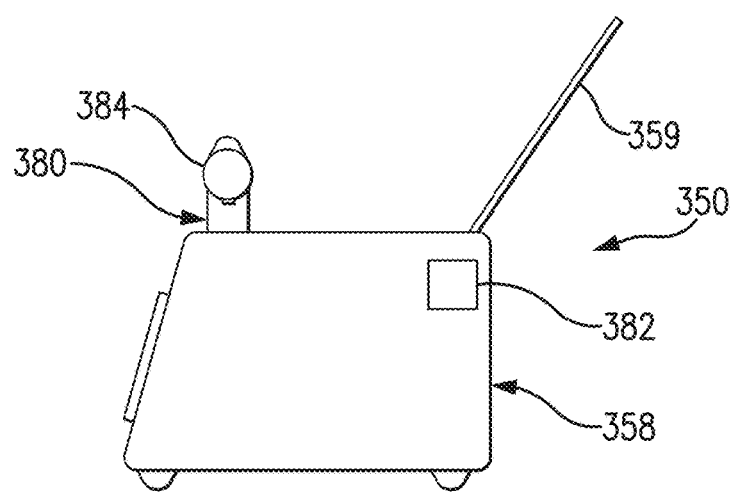
FIG. 22 is a right side view of the device of FIG. 21.
Figure 23:
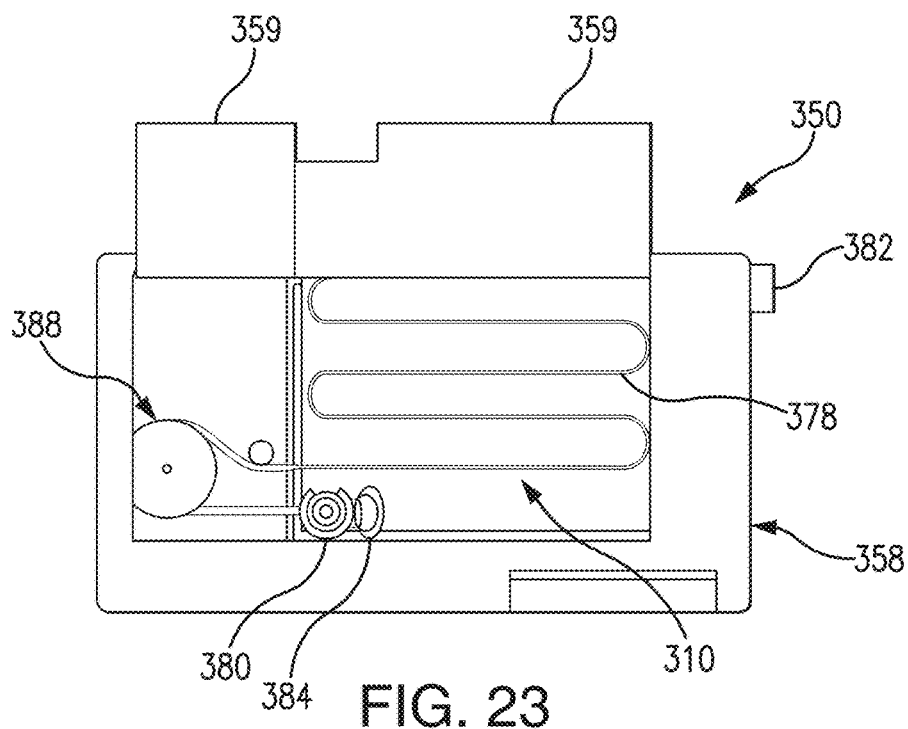
FIG. 23 is a top view of the device of FIG. 21.
Figure 24:
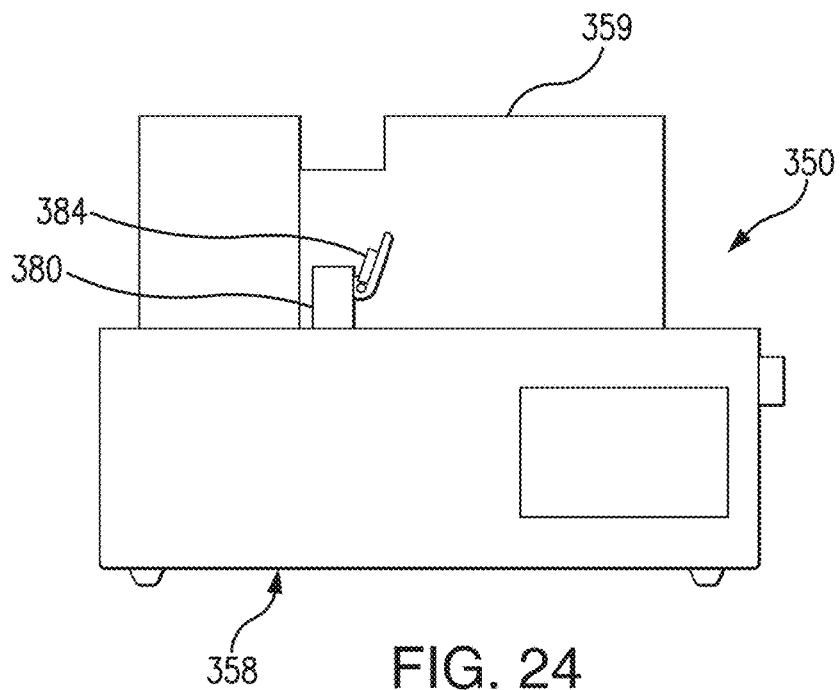
FIG. 24 is a front side view of the device of FIG. 21.
Figure 25:
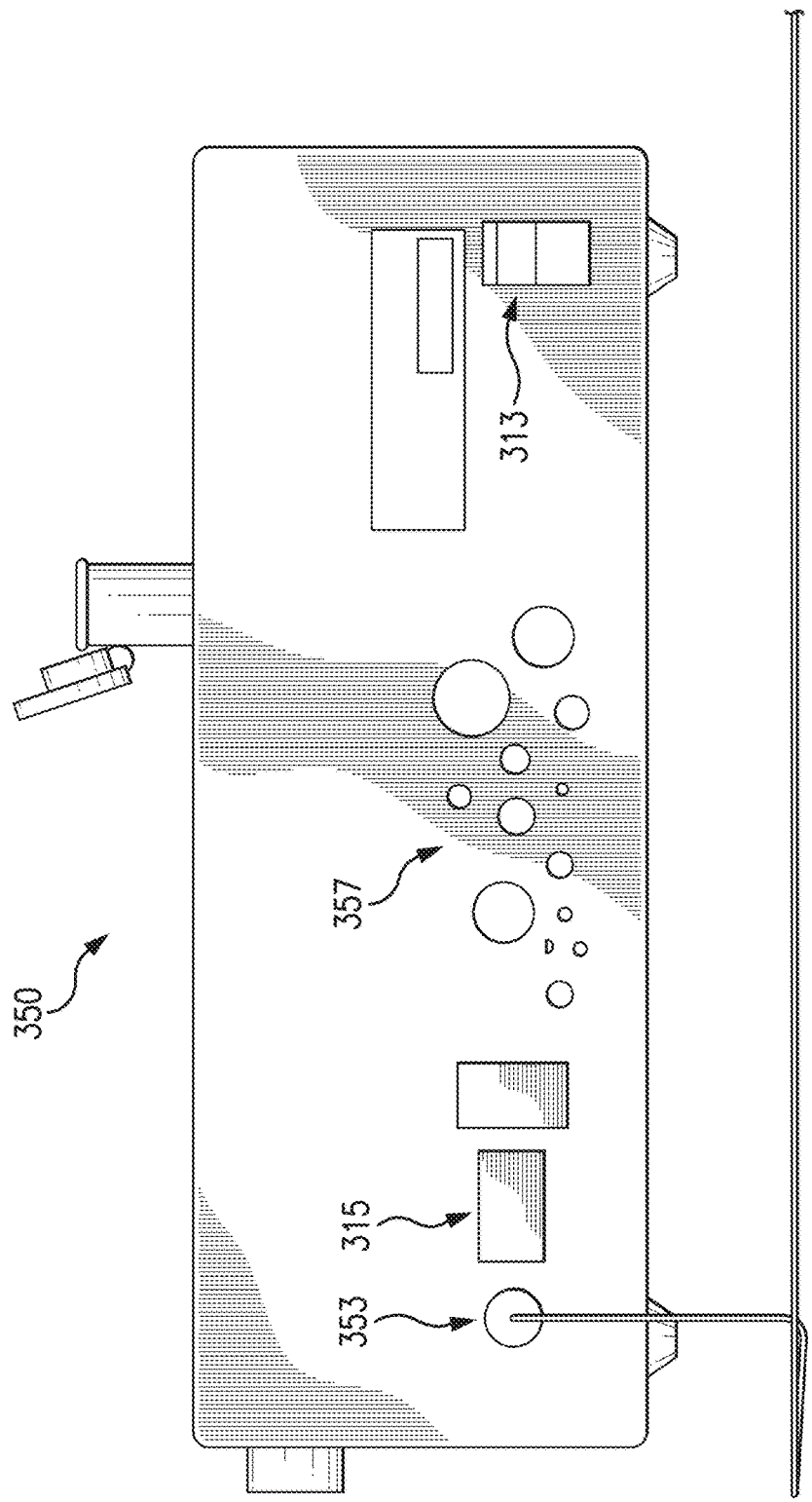
FIG. 25 is a rear side view of the device of FIG. 21.
Figure 26:
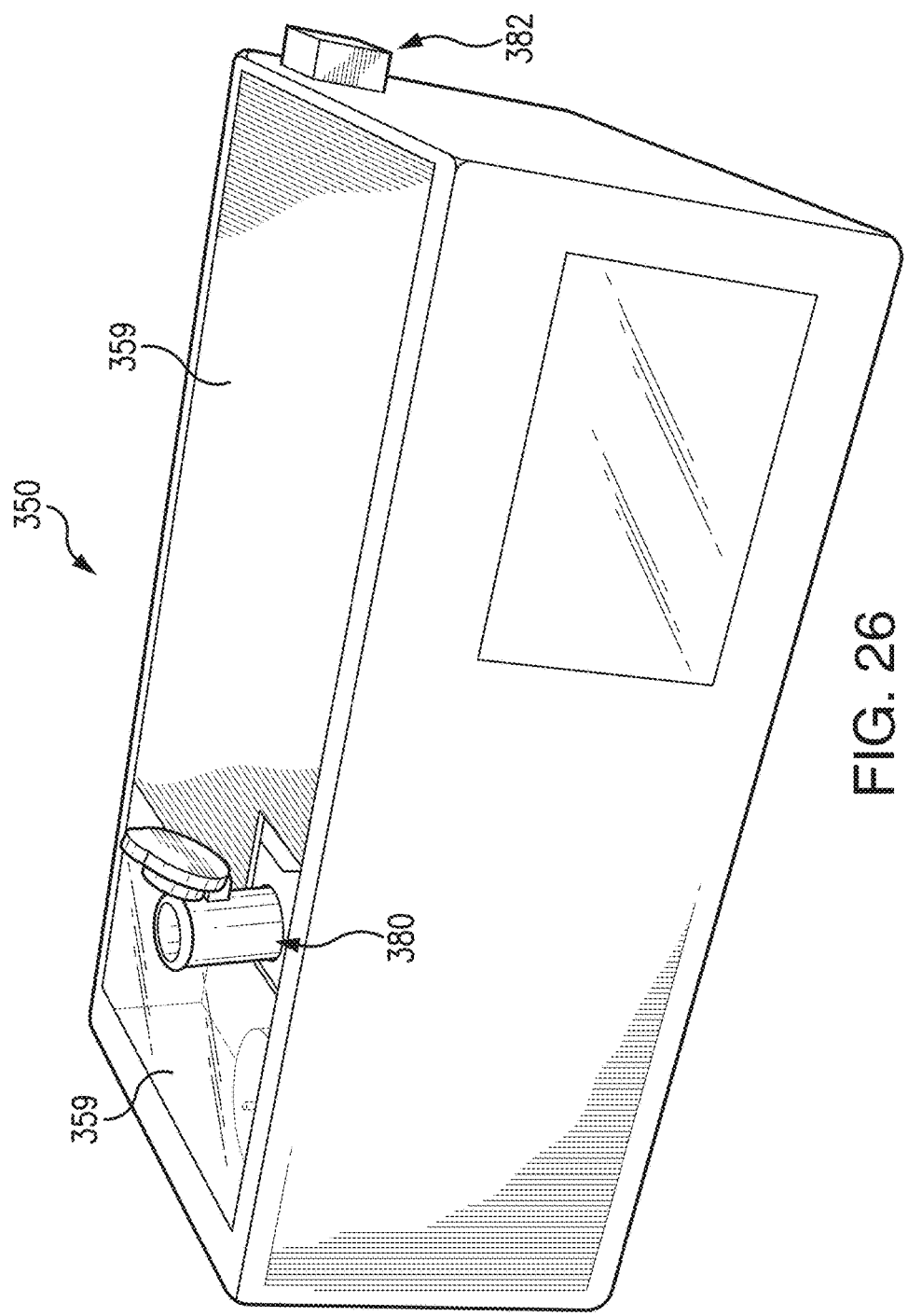
FIG. 26 shows the device of FIG. 21 with the access panels in a closed position.
Figure 27:
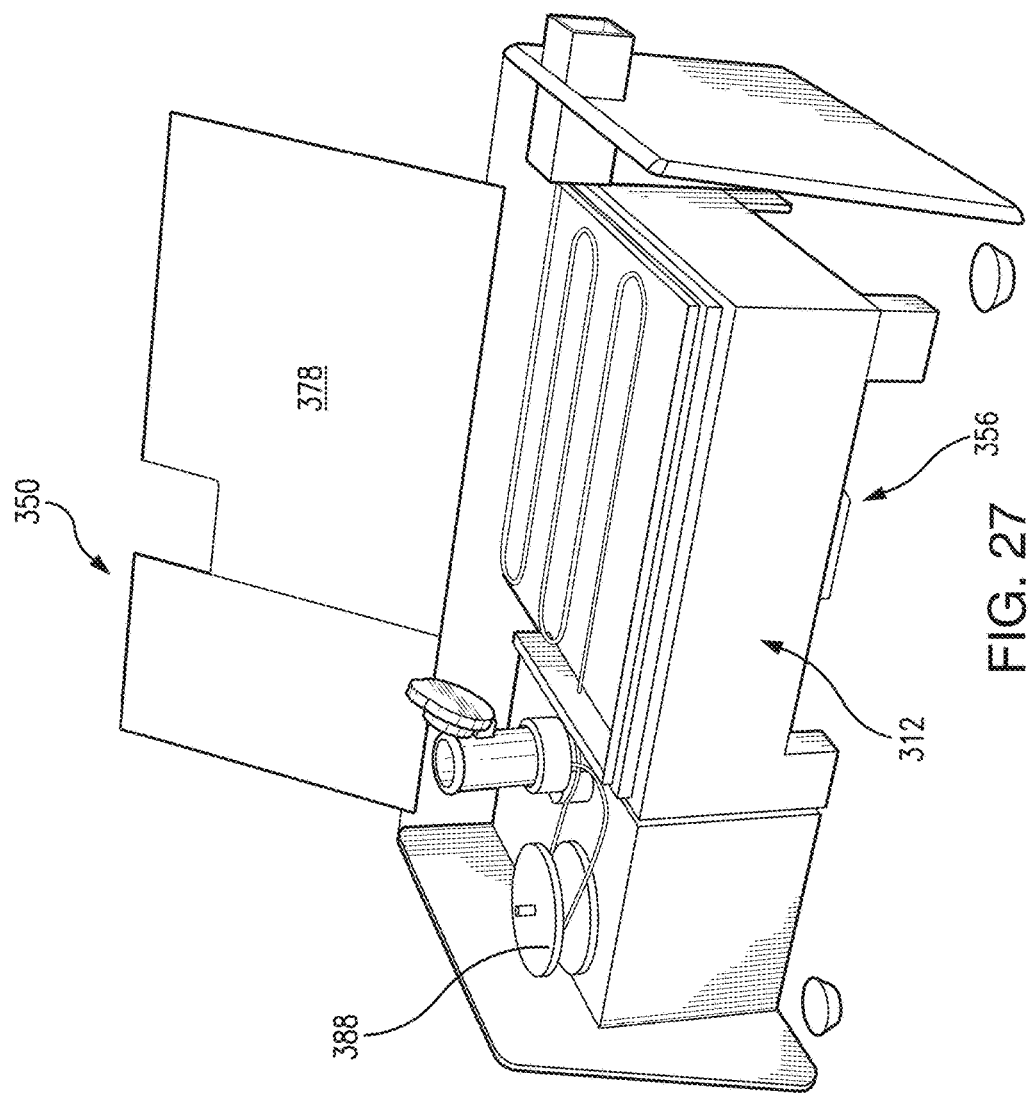
FIG. 27 shows the device of FIG. 2 with a portion of the housing removed to reveal the device's inner components.
Figure 28:
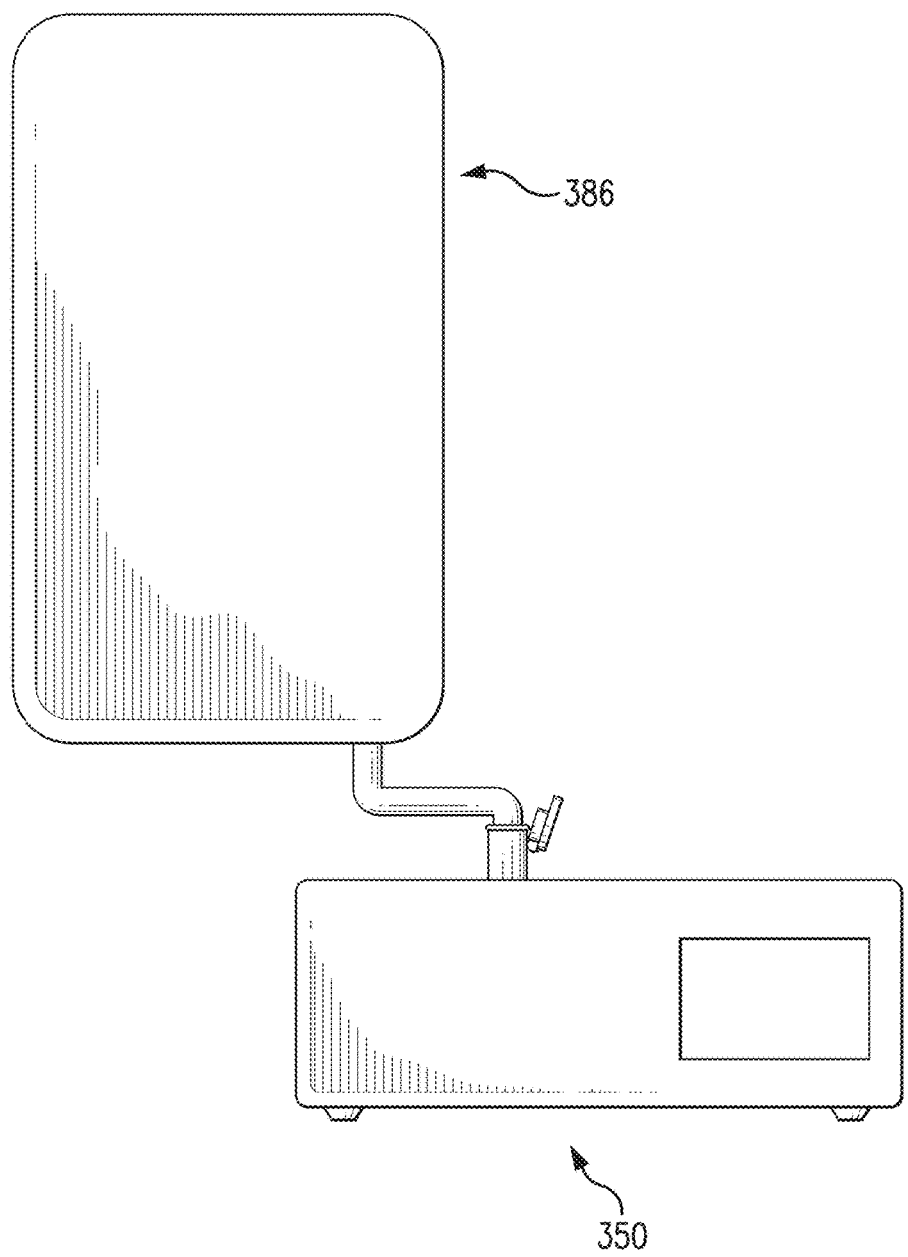
FIG. 28 is a front view of the device of FIG. 26 showing a sample tank continuously feeding the nucleic acids and/or cells into the device.
Figure 30:
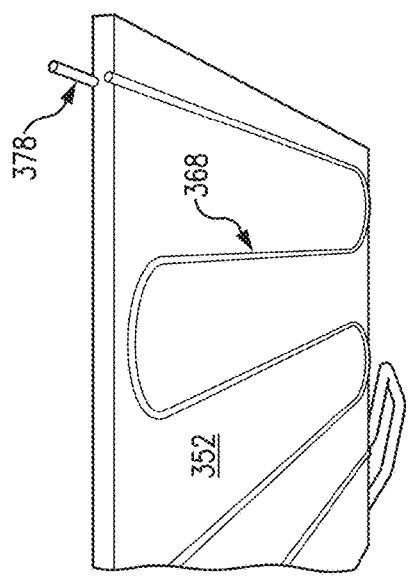
FIG. 30 is a bottom perspective view of a portion of the magnetic-field-inducing circuit of FIG. 29.
Figure 32:
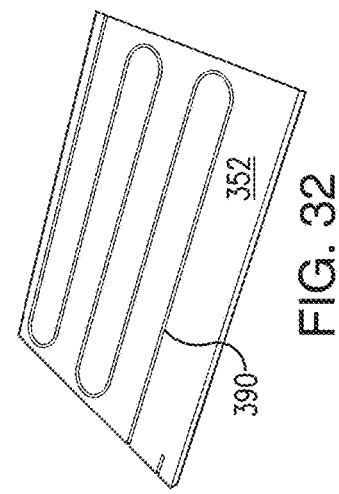
FIG. 32 is a top perspective view of the magnetic-field-inducing circuit of FIG. 29.
Figure 29:
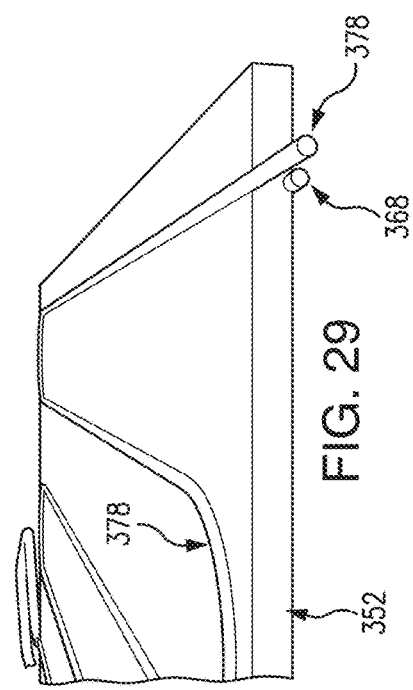
FIG. 29 is a top perspective view of the magnetic-field-inducing circuit of the device of FIG. 21.
Figure 31:
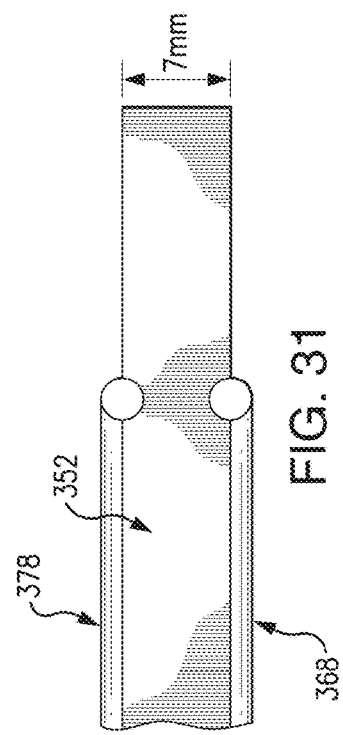
FIG. 31 is a side view of a portion of the magnetic-field-inducing circuit of FIG. 29.

The magnetic-field-inducing circuit 54 of this embodiment is a serial circuit (actually, two serial circuits on one vial support 52). The magnetic field can be induced by circuits having other configurations, so long as they induce the desired magnetic field and retain the ligation and/or transformation process as thermal-free. For example, FIG. 10 shows a first alternative circuit 54*a* that can be used in the device 50 and that is the same as that of FIGS. 6-7 except that the two serial circuits are combined into a single serial circuit. And FIG. 11 shows a second alternative circuit 54*b* that can be used in the device 50 and that is similar to that of FIG. 10 except that it's a parallel circuit. In other embodiments, the conductor is routed centrally between every row of the holes such that the centers of all of the holes are the same normal distance from the conductor routed on two opposite sides thereof. In yet other embodiments, the circuit includes series and parallel portions, for example, the alternative circuits 54*c*(i)-54*c*(vi) depicted in FIGS. 12A-12F respectively. It will be understood that circuits having many other designs can be included in the device 50.

FIG. 13 shows a device 150 for ligating nucleic acids according to a third example embodiment of the present invention, or for transforming cells with exogenous nucleic acids according to a fourth example embodiment of the present invention. The device is substantially similar to that of the first and second embodiments. Thus, the device 150 includes a circuit (not shown) that induces an electromagnetic field, a vial support 152 that supports vials 110 holding the samples, a control unit 112 for operating the circuit, and a housing 158 for all of these components. In addition, the device 150 can, but does not necessarily have to, include a cooling system (not shown). In these embodiments, however, the control unit 112 is provided as an integral component of the device 150 and is incorporated into the device housing 158.

The control unit 112 in these embodiments includes a power supply (not shown), control circuitry and/or programmed processor (not shown), one or more control inputs 118 such as the depicted keypad, and one or more control inputs 120 such as the display screen. These control unit 112 components are operable to control the voltage, current, time, and/or other operating parameters of the amplification device 150. Typically, these control unit 112 components, as well as the magnetic-field inducing circuit, the vial support 152, and the vials 110 held by the vial support, are all substantially similar to those of the above-described embodiments.

In these embodiments, the housing 158 additionally houses the control unit 112, so the housing is sized larger relative to that of the above-described embodiments. In addition, the housing 158 of these embodiments typically includes at least one access panel 159 that covers and partially defines a processing compartment in the housing 158 in which the vials 110 are held during operation of the amplification device 150. The access panel 159 can be in the form of a hinged lid, as depicted, that moves between a closed position (covering the processing compartment during operation of the amplification device 150) and an open position (for inserting and removing the vials 110).

FIGS. 14-20 show a device 250 for ligating nucleic acids according to a fifth example embodiment of the present invention, or for transforming cells with exogenous nucleic acids according to a sixth example embodiment of the present invention. The device 250 is substantially similar to that of the third and fourth embodiments, in that the control unit 212 is provided as an integral component of the device and is incorporated into the device housing 258. Thus, the device 250 includes a circuit 254 that induces an electromagnetic field, a vial support 252 that supports vials 210 holding the samples, the control unit 212 for operating the circuit, and the housing 258 for all of these components. Typically, these components are all substantially similar to those of the above-described third and fourth embodiments.

In these embodiments, however, the control unit 212 includes a combined input-output device 218/220 such as the depicted touch screen. Typically, the control unit 212 includes the power input connector 253, fuses for over-current protection 215, and an on-off switch 213. The components of the control unit 212 in typical commercial embodiments are selected for input voltages to the power supply of about 90 to 240 VAC, working voltages of about 12 VDC, and working power of about 30 W. In such embodiments, and with the vial support 252 configured for holding 100 vials 210, the device 250 can typically be operated at a temperature of about 25 C to process the samples in the vials in a working time of between about 2 min and about 30 min.

In addition, the housing 258 of this embodiment has a generally barrel-vault shape with two sliding access panels 259 that slide between the open and closed positions to cover and partially define the processing compartment 261 in the housing 258 in which the vials 210 are held during operation of the amplification device 250. Further, the housing 258 can include an array of ventilation openings 257 that form a part of a cooling system, which can additionally include at least one fan and controls for the fan. It should be noted that the dimensional and operating information in these drawings is representative of a typical commercial embodiment and is thus included for illustration purposes only and is not limiting of the invention.

FIGS. 21-32 show a device 350 for ligating nucleic acids according to a seventh example embodiment of the present invention, or for transforming cells with exogenous nucleic acids according to an eighth example embodiment of the present invention. The device 350 is similar to those of the previously described embodiments in that it includes a circuit 354 that induces an electromagnetic field and a control unit 312 for operating the circuit, and typically includes a cooling system 356 as well as a housing 358 for all of these components. Typically, these components are all substantially similar to those of the above-described embodiments.

In these embodiments, however, the device 350 is designed for continuous processing of the samples, instead of the batch-processing designs of the above-described embodiments. Thus, instead of a vial support for holding an array of individual vials containing respective discrete samples to be processed in batches, the device 350 includes at least one tube 310 that carries the nucleic acids and/or the cells. The tube 310 includes a working portion 378 of the tube in the processing compartment 361 of the housing 358, an inlet portion 380, and an outlet portion 382. The inlet 380 typically includes a closure 384, for example a friction-fit lid (as depicted) or a screw-on lid, that can be removed to connect to a tank 386 holding the nucleic acid sample. In addition, the inlet 380 can include interchangeable end fittings for adapting to different sizes of discharge hoses of sample tanks 386. And the outlet 382 typically includes a closure, for example a friction-fit lid or a screw-on lid, that can be removed to connect to a spectrophotometer for analysis of the sample, a storage tank, or another post-electromagnetic treatment device. The inlet 380 and the outlet 382 are typically closed when the device 350 is not in use to avoid contamination of the inside of the tube 376. The working portion 378, inlet portion 380, and outlet portion 382 of the tube 310 can be provided by conventional tubing or hosing that is well known in the art. In typical commercial embodiments, for example, the tube 310 is made of silicon or TEFLON material.

When using this continuous-processing device 350, a supply tank 386 holding the nucleic acids and/or cells is connected to the inlet 380 and the nucleic acids and/or cells are flowed through the tube working portion 378 to provide the desired residence time for the exposure of the nucleic acids and/or cells to the magnetic field in the processes disclosed herein. The tube working portion 378 has a diameter and length selected, in conjunction with the flow rate of the nucleic acids and/or cells, to provide the desired residence time of the sample for exposure to the magnetic field. In the depicted embodiments, for example, the tube working portion 378 has a diameter of 1 mm and a length of 75 cm. For these embodiments, the residence time is typically about 2 min to about 30 min. When the device 350 is operated at a temperature of about 25° C. To accomplish this, the flow rate of the sample through the tube working portion 378 is typically about 37.5 µL/min to about 1.25 µL/min, respectively. In other embodiments, the tube working portion 378 has a diameter and length that are larger or small, the operating temperature is higher or lower, and/or the flow rate of the sample through the tube working portion is increased or decreased, to provide the desired residence time. In typical embodiments such as that depicted, one tube working portion 378 is arranged in a serpentine or sinusoidal configuration to provide the desired length in a compact manner. In other embodiments, the tube working portion is arranged in a helical, spiral, or other configuration, and/or multiple tube working portions are included. The device 350 includes a pump 388 to cause the sample to flow through the tube 311. The pump 388 can be of a convention type such as a peristaltic pump for providing the flow rates disclosed above. In typical embodiments such as those depicted, the pump 388 is operably connected to the tube 311 between its inlet 380 and its working portion 378. The pump 388 can be operated continuously so that the sample is constantly flowed through the tube working portion 378, or it can be operated intermittently to increase the residence time of the sample's exposure to the magnetic field. In other embodiments, the amplification device is provided without a pump and the inlet and outlet are positioned for gravity flow of the sample through the tube working portion.

The electromagnetic field-inducing circuit 354 includes the conductor 368 and typically also includes resistors as noted above. In typical embodiments, the amplification device includes a tube support 352 to which the conductor 368 and the tube working portion 378 are mounted at a fixed separation distance. For example, the tube support 352 can be provided by a plate with the conductor 368 mounted on its bottom side and with the tube working portion 378 mounted on its top side at a separation of about 7 mm, as depicted. The tube-support plate 352 can be made of a material such as polystyrene or BAKELITE material. The tube-support plate 352 can include channels 390 that receive the conductor 368 and the tube working portion 378 in their fixed positions and hold them in place. The conductor 368 and the tube working portion 378 are positioned equidistantly along their entire lengths, for example vertically aligned in conforming arrangements, to provide a uniform exposure of the nucleic acid to the magnetic field. For example, when the tube working portion 378 is arranged in serpentine configuration, the conductor 368 can be arranged in a conforming serpentine configuration so that the two are aligned and equidistantly separated along their entire lengths, as depicted. In other embodiments, the conductor is coiled around the tube working portion and/or multiple conductors are provided for each tube.

In addition, in these embodiments, the control unit 312 includes a combined input-output device 318/320 such as the depicted touch screen. Typically, the control unit 312 includes the power input connector 353, fuses for overcurrent protection 315, and an on-off switch 313. The components of the control unit 312 in typical commercial embodiments are selected for input voltages to the power supply of about 90 to 240 VAC, working voltages of about 12 VAC, and working power of about 30 W. In such embodiments, examples of the approximate mini-current I and the magnetic field B are the same as those listed above in Tables 1 and 2 for the first embodiment, and additionally can include those approximate values listed below in Tables 3-6. Each of the ranges between each of the listed approximate values (referring to Tables 3-6 collectively) is considered to represent a separate embodiment and mode of use. And as with Tables 1 and 2, the magnetic field B is the strength of the magnetic field at and applied to the samples in the tube 310, which is necessarily less than the core magnetic field immediately adjacent the conductor 368 inducing it due to the distance spacing "d" between the conductor and the tube axial centerline. Note that the distance d is the conductor-to-tube-centerline spacing, subject to the conditions described with respect to the first and second embodiments above.

In Table 3, the voltage and current I were varied to produce various magnetic fields B on the samples to assess the resulting ligation and/or transformation. And in Tables 4-6, the voltage and resistance were varied to produce the same current I and magnetic field B on the samples to assess different design and construction options. In all four Tables, the distance "d" is 7 mm.

TABLE 3

| Working Voltage (V) | Mini-Current I (Amps) | Magnetic Field B (Gauss) |
|---|---|---|
| 0.01 | 0.005 | 0.001 |
| 0.05 | 0.025 | 0.009 |
| 0.1 | 0.05 | 0.019 |
| 0.2 | 0.10 | 0.039 |
| 0.3 | 0.15 | 0.059 |
| 0.4 | 0.20 | 0.080 |
| 0.5 | 0.25 | 0.100 |
| 0.6 | 0.30 | 0.120 |
| 0.7 | 0.35 | 0.141 |
| 0.8 | 0.40 | 0.161 |
| 0.9 | 0.45 | 0.180 |
| 1.0 | 0.50 | 0.200 |
| 1.2 | 0.60 | 0.241 |
| 1.4 | 0.70 | 0.282 |
| 1.5 | 0.80 | 0.322 |
| 1.8 | 0.90 | 0.360 |
| 2.0 | 0.90 | 0.360 |
| 2.0 | 1.00 | 0.402 |
| 2.4 | 1.20 | 0.480 |
| 3.0 | 1.50 | 0.610 |

TABLE 4

| Working Voltage (VDC) | Mini-Current I (Amps) | Resistance (Ohms) | Magnetic Field B (Gauss) |
|---|---|---|---|
| 0.5 | 1.0 | 0.5 | 0.402 |
| 1.0 | 1.0 | 1.0 | 0.402 |
| 1.5 | 1.0 | 1.5 | 0.402 |
| 2.0 | 1.0 | 2.0 | 0.402 |
| 2.5 | 1.0 | 2.5 | 0.402 |
| 3.0 | 1.0 | 3.0 | 0.402 |
| 3.5 | 1.0 | 3.5 | 0.402 |
| 4.0 | 1.0 | 4.0 | 0.402 |
| 4.5 | 1.0 | 4.5 | 0.402 |
| 5.0 | 1.0 | 5.0 | 0.402 |
| 5.5 | 1.0 | 5.5 | 0.402 |
| 6.0 | 1.0 | 6.0 | 0.402 |
| 6.5 | 1.0 | 6.5 | 0.402 |
| 7.0 | 1.0 | 7.0 | 0.402 |
| 7.5 | 1.0 | 7.5 | 0.402 |
| 8.0 | 1.0 | 8.0 | 0.402 |
| 8.5 | 1.0 | 8.5 | 0.402 |
| 9.0 | 1.0 | 9.0 | 0.402 |
| 9.5 | 1.0 | 9.5 | 0.402 |
| 10.0 | 1.0 | 10.0 | 0.402 |
| 10.5 | 1.0 | 10.5 | 0.402 |
| 11.0 | 1.0 | 11.0 | 0.402 |
| 11.5 | 1.0 | 11.5 | 0.402 |
| 12.0 | 1.0 | 12.0 | 0.402 |

TABLE 5

| Working Voltage (VDC) | Mini-Current I (Amps) | Resistance (Ohms) | Magnetic Field B (Gauss) |
|---|---|---|---|
| 0.5 | 1.2 | 0.42 | 0.48 |
| 1.0 | 1.2 | 0.83 | 0.48 |
| 1.5 | 1.2 | 1.25 | 0.48 |
| 2.0 | 1.2 | 1.67 | 0.48 |
| 2.5 | 1.2 | 2.083 | 0.48 |
| 3.0 | 1.2 | 2.50 | 0.48 |
| 3.5 | 1.2 | 2.92 | 0.48 |
| 4.0 | 1.2 | 3.33 | 0.48 |
| 4.5 | 1.2 | 3.75 | 0.48 |
| 5.0 | 1.2 | 4.17 | 0.48 |
| 5.5 | 1.2 | 4.58 | 0.48 |
| 6.0 | 1.2 | 5.00 | 0.48 |
| 6.5 | 1.2 | 5.42 | 0.48 |
| 7.0 | 1.2 | 5.83 | 0.48 |
| 7.5 | 1.2 | 6.25 | 0.48 |
| 8.0 | 1.2 | 6.67 | 0.48 |
| 8.5 | 1.2 | 7.08 | 0.48 |
| 9.0 | 1.2 | 7.50 | 0.48 |
| 9.5 | 1.2 | 7.92 | 0.48 |
| 10.0 | 1.2 | 8.33 | 0.48 |
| 10.5 | 1.2 | 8.75 | 0.48 |
| 11.0 | 1.2 | 9.17 | 0.48 |
| 11.5 | 1.2 | 9.58 | 0.48 |
| 12.0 | 1.2 | 10.0 | 0.48 |

TABLE 6

| Working Voltage (VDC) | Mini-Current I (Amps) | Resistance (Ohms) | Magnetic Field B (Gauss) |
|---|---|---|---|
| 0.5 | 1.5 | 0.33 | 0.61 |
| 1.0 | 1.5 | 0.67 | 0.61 |
| 1.5 | 1.5 | 1.00 | 0.61 |
| 2.0 | 1.5 | 1.33 | 0.61 |
| 2.5 | 1.5 | 1.67 | 0.61 |
| 3.0 | 1.5 | 2.00 | 0.61 |
| 3.5 | 1.5 | 2.33 | 0.61 |
| 4.0 | 1.5 | 2.67 | 0.61 |
| 4.5 | 1.5 | 3.00 | 0.61 |
| 5.0 | 1.5 | 3.33 | 0.61 |
| 5.5 | 1.5 | 3.67 | 0.61 |
| 6.0 | 1.5 | 4.00 | 0.61 |
| 6.5 | 1.5 | 4.33 | 0.61 |
| 7.0 | 1.5 | 4.67 | 0.61 |
| 7.5 | 1.5 | 5.00 | 0.61 |
| 8.0 | 1.5 | 5.33 | 0.61 |
| 8.5 | 1.5 | 5.67 | 0.61 |
| 9.0 | 1.5 | 6.00 | 0.61 |
| 9.5 | 1.5 | 6.33 | 0.61 |
| 10.0 | 1.5 | 6.67 | 0.61 |
| 10.5 | 1.5 | 7.00 | 0.61 |
| 11.0 | 1.5 | 7.33 | 0.61 |
| 11.5 | 1.5 | 7.67 | 0.61 |
| 12.0 | 1.5 | 8.00 | 0.61 |

In a preferred embodiment, the device 350 is operated with good results with a mini-current I of about 900 mA to induce a magnetic field B of about 0.35 to about 0.36 Gauss on the samples in the tubes 310 carrying it when the tube and the magnetic-field-inducing conductor 368 are uniformly positioned relative to each other and uniformly spaced apart by a distance d of, for example, about 7.0 mm. In other preferred embodiments, the device 350 is operated with a mini-current I of about 0.8 A to induce a magnetic field B of about 0.322 Gauss on the sample, with a mini-current I of about 1.0 A to induce a magnetic field B of about 0.402 Gauss on the sample, or with a mini-current I and a magnetic field B within the ranges defined by those approximate values. In still other preferred embodiments, the device 350 is operated with a mini-current I of about 1.2 A to induce a magnetic field B of about 0.48 Gauss on the sample or with a mini-current I of about 1.5 A to induce a magnetic field B of about 0.61 Gauss on the sample. And in still other preferred embodiments, the device 350 is operated with a mini-current I within the range of about 1.0 A to about 1.2 A, about 1.2 A to about 1.5 A, or about 1.0 A to about 1.5 A, to induce a magnetic field B on the sample within the range of about 0.402 Gauss to about 0.48 Gauss, about 0.48 Gauss to about 0.61 Gauss, or about 0.402 Gauss to about 0.61 Gauss, respectively.

It will be understood that the device 350 can be operated to induce a magnetic field B on the sample of higher or lower strengths to produce the intended results as described herein. In some embodiments, for example, the magnetic-field-inducing conductor 368 is spaced a different distance d (than the 7.0 mm spacing of the depicted embodiment) from the centerline of the tube 310 carrying the sample, and/or a current I of a different strength is passed through the conductor 368 (by using a different voltage and/or resistance), so that a magnetic field B of different strength is induced by the conductor and applied to the sample. Typically, for a decreased conductor-to-sample distance d and/or a stronger current I, a stronger magnetic field B is induced, and for an increased conductor-to-sample spacing and/or a weaker current, a weaker magnetic field is induced, to produce the desired amplification.

In other embodiments, a core magnetic field of a different strength is induced to apply the same-effect magnetic field B to the samples. For example, in some embodiments the magnetic-field-inducing conductor 368 is spaced a different distance d (than the 7.0 mm spacing of the depicted embodiment) from the tube 310 holding the samples, so a current I of a different strength is passed through the conductor 368 (by using a different voltage and/or resistance) in order to induce a core magnetic field of a different strength such that, given the different conductor-to-sample spacing, the magnetic field B at and applied to the sample is still in the same range of about 0.322 Gauss to about 0.402 Gauss. And in other embodiments, a current I of a different strength is passed through the conductor 68, so a core magnetic field of a different strength is induced, and in order for the magnetic field B at and applied to the samples to be still in the same preferred range of about 0.322 Gauss to about 0.402 Gauss, a different conductor-to-sample distance spacing d is used.

In order to determine the conductor-to-sample distance spacing d and the current I to provide a magnetic field B at and applied to the samples in for example the preferred range of about 0.322 Gauss to about 0.402 Gauss, the same Biot and Savat equation (described above with respect to Tables 1 and 2) is used in the same fashion.

Furthermore, the housing 358 of these embodiments can include an array of ventilation openings 357 that form a part of a cooling system 356, which can additionally include at least one fan and controls for the fan. Also, the housing 358 can include two separately movable access panels 359 that cover and partially define the processing compartment 361 and a pump compartment 389. The access panels 359 can be in the form of hinged lids, as depicted, that move between a closed position (covering the processing and pump compartments during operation of the amplification device 350) and an open position (for accessing the tube working portion 378 and the pump 388). It should be noted that the dimensional and operating information in these drawings is representative of a typical commercial embodiment and is thus included for illustration purposes only and is not limiting of the invention.

In another embodiment, the device includes at least one magnetic-field-inducing circuit and at least one heating element in a combination design, with the heating elements being of a conventional type known in the art. In yet another embodiment, the device includes a magnetic-field-inducing circuit (with or without any heating elements) and is operated at higher currents (higher than the mini-current described above) to generate sufficient heat sufficiently close to the sample to materially impact the ligation and/or transformation processes. In these embodiments, the device ligates the nucleic acid by the application of the magnetic field and heat in a combination of a magnetic-field process and a thermal process, or transforms the cells with exogenous nucleic acids by the application of the magnetic field and heat in a combination of a magnetic-field process and a thermal process. As such, these combination devices are not operable to produce a thermal-free ligation or transformation process. For example, testing was done by placing one of the electromagnetic devices inside a closed chamber that is able to maintain a constant temperature, then setting the chamber temperature above and below ambient temperature (25° C.), such as at 10° C., 15° C., 20° C., 30° C., 35° C., 40° C., 45° C., 50° C., and 55° C. This testing showed that the device can work with generally good results when small amounts of heat are applied to the sample being amplified. So designs combining both heat and an electromagnetic field are contemplated by and included within the present invention.

II. Methods for Ligating Nucleic Acids

Described herein are methods for ligating nucleic acid fragments together into one longer nucleic acid molecule. The methods generally involve exposing the nucleic acid fragments to an electromagnetic field, for example a mini-current magnetic field, while performing the steps of ligation. In one aspect, the method involves exposing the nucleic acid fragments to a mini-current magnetic field for a sufficient time to ligate the fragments. In certain aspects, a ligase enzyme can be used during the method; however, this component is optional. Thus, in one aspect, the methods described herein do not use a ligase enzyme.

The process is carried out using a device that uses an electromagnetic field to perform the ligation process. For example, the ligation and/or transformation devices described herein can be used to carry out the ligation process. When using a batch-processing device, the nucleic acid fragments to be ligated are placed in one or more vials. The vials can be of the type described above. Thus, the volume of the sample tubes can be 0.2 mL, 0.6 mL, 1.0 mL, 1.5 mL, or 2.0 mL. The thickness of the tube wall can be 0.5 mm to 1.5 mm, preferably 1.15 mm to 1.20 mm, or more preferably 1.17 mm. The wall thickness of the sample tube can be varied in order to maximize magnetic field distribution. When using a continuous-processing device, a tank of the nucleic acid fragments to be ligated is connected to the device and the nucleic acid fragments are flowed through the tubing in the device. The nucleic acid fragments can be any molecules where it is possible and desirable to ligate (i.e., stitched together to form a longer specific nucleic acid sequence). In one aspect, the nucleic acid fragments can be oligonucleotides, deoxyribonucleic acid (DNA), ribonucleic acid (RNA), or peptide nucleic acid (PNA). The nucleic acids of interest introduced by the present method can be a from any source, such as a nucleic acids obtained from cells in which they occur in nature, recombinantly-produced nucleic acids, or chemically-synthesized nucleic acid. For example, the nucleic acid fragments can be cDNA, genomic DNA, or DNA synthesized to have the nucleotide sequence corresponding to that of naturally-occurring DNA. The nucleic acid can also be a mutated or altered form of nucleic acid (e.g., DNA that differs from a naturally occurring DNA by an alteration, deletion, substitution, or addition of at least one nucleotide residue), or can be a nucleic acid that does not occur in nature. In one aspect, the DNA can be genomic DNA. In other aspects, the DNA can be double-stranded DNA including, but not limited to, a plasmid (linear or coiled, etc.), cosmid, phage, virus, yeast artificial chromosome, bacterial artificial chromosome, other artificial chromosomes, or the like. Alternatively, the DNA can be single stranded.

In one aspect, the nucleic acid fragments can be ligated to form a functional nucleic acid. Functional nucleic acids are nucleic acid molecules that have a specific function, such as binding a target molecule or catalyzing a specific reaction. Functional nucleic acid molecules can be divided into the following categories, which are not meant to be limiting. For example, functional nucleic acids include antisense molecules, aptamers, ribozymes, triplex forming molecules, siRNA, miRNA, shRNA, and external guide sequences. The functional nucleic acid molecules can act as affectors, inhibitors, modulators, and stimulators of a specific activity possessed by a target molecule, or the functional nucleic acid molecules can possess a de novo activity independent of any other molecules.

Functional nucleic acids can be small gene fragments that encode dominant-acting synthetic genetic elements (SGEs), e.g., molecules that interfere with the function of genes from which they are derived (antagonists) or that are dominant constitutively active fragments (agonists) of such genes. SGEs can include, but are not limited to, polypeptides, inhibitory antisense RNA molecules, ribozymes, nucleic acid decoys, and small peptides. The small gene fragments and SGE libraries disclosed in U.S. Patent Publication No. 2003/0228601, which is incorporated by reference, can be used herein.

In general, the methods described herein involve the application of an electromagnetic field to a sample containing the nucleic acid and, optionally, a ligase in the absence of applied heat in order to ligate nucleic acid fragments to form a longer nucleic acid sequence of interest. Typically, the methods typically involve the application of a mini-current magnetic field to the sample in the absence of applied heat. Thus, the reaction is typically performed at a constant temperature of less than or equal to about 30° C., preferably less than or equal to about 25° C. The magnitude and duration of the magnetic field applied to the nucleic acid can vary. For example, the magnitude of the magnetic field applied in steps (a) and (b) above can be the same or different. Similarly, the duration of exposure to the magnetic field can be the same or different in steps (a) and (b). Different voltages can be used including different mini-currents to induce the magnetic field B by the magnetic-field inducing circuit. In one aspect, the voltage/mini-current is 50 mV/25 mA, 100 mV/50 mA, 150 mV/80 mA, 200 mV/100 mA, 250 mV/100 mA, 300 mV/150 mA, 500 mV/250 mA, 800 mV/400 mA, 1000 mV/500 mA, 1500 mV/800 mA, or 2000 mV/1000 mA. In another aspect, the voltage and mini-current in steps (a) and (b) are from 50 mV to 2,000 mV and from 25 mA to 1,000 mA. In another aspect, the voltage and mini-current in steps (a) and (b) are from 800 mV to 1,000 mV and from 400 mA to 500 mA. In a further aspect, the duration of exposure of the sample to the magnetic field B in steps (a) and (b) can range from 5 minutes to 60 minutes, from 5 minutes to 50 minutes, from 5 minutes to 40 minutes, from 5 minutes to 30 minutes, or from 5 minutes to 20 minutes. When using a batch-processing device, the vials containing the sample are held in place on the vial support for the duration of exposure of the sample to the magnetic field B in steps (a) and (b). When using a continuous-processing device, the nucleic acid is flowed through the tubing in the device at a rate selected to achieve a residence time for the duration of exposure of the sample to the magnetic field B in steps (a) and (b). In addition, the proportions of the reagents used in the reaction are the same whether using the batch-processing device or the continuous-processing device, however, the volumes of the final reaction mix typically can be in the range of about 10 µL to about 1000 liters when using the continuous-processing device. In yet another aspect, the magnetic field B induced by the mini-current is about 0.35 or about 0.36 Gauss. In a typical use of the method, the voltage is about 12V and the mini-current is about 900 mA, and the induced magnetic field B is about 0.35 Gauss. Devices for generating the mini-current magnetic field and exposing the sample of nucleic acid to the magnetic field are described in detail above.

The sample of nucleic acid fragments can be prepared using techniques known in the art for preparing samples used in conventional ligation techniques. For example, the nucleic acid fragments can be dissolved in water and buffer, where the buffered solution contains a divalent cation such as $Ca^{2+}$ or $Mg^{2+}$. In one aspect, the nucleic acid fragments (gene parts) to be ligated are purified by gel electrophoresis prior to electromagnetic ligation. In another aspect, the ratio of inserts to expression vector is 5:3, 1:2, 1:1, or 2:1. In some aspects, electromagnetic ligation is conducted in the presence of a ligase enzyme. In other aspects, electromagnetic ligation is conducted in the absence of a ligase enzyme. In one aspect, the electromagnetic ligation is carried out at from about 5 min to about 60 min at room temperature. In a further aspect, electromagnetic ligation is complete in about 15 min. In one aspect, the effectiveness of ligation can be assessed by gel electrophoresis, wherein the ligated construct is measured against a marker of known molecular weight.

The methods described herein can be used in any application where conventional ligation is used. For example, the methods described herein permit the ligation of DNA fragments to form cassettes containing several genes, which can then be themselves ligated into a larger plasmid or other vector for later transformation into cells.

In one aspect, ligated DNA can be sequenced using any method known in the art such as, for example, dideoxy or Sanger sequencing, fluorescent labeling, or capillary electrophoresis. The sequence of the amplified DNA thus determined can be queried against a database or aligned to a known sequence to assess the accuracy of the electromagnetic ligation technique.

III. Methods for Transforming Cells

Described herein are methods for transforming cells with exogenous nucleic acids. The methods generally involve exposing the cells and exogenous nucleic acids to an electromagnetic field, for example a mini-current magnetic field, while performing the steps of transformation. In one aspect, the method involves exposing the cells and exogenous nucleic acids to a mini-current magnetic field for a sufficient time to transform the cells.

The process is carried out using a device that uses an electromagnetic field to perform the transformation process. For example, the ligation and/or transformation devices described herein can be used to carry out the transformation process. When using a batch-processing device, the exogenous nucleic acids and the cells to be transformed are placed in one or more vials. The vials can be of the type described above. Thus, the volume of the sample tubes can be 0.2 mL, 0.6 mL, 1.0 mL, 1.5 mL, or 2.0 mL. The thickness of the tube wall can be 0.5 mm to 1.5 mm, preferably 1.15 mm to 1.20 mm, or more preferably 1.17 mm. The wall thickness of the sample tube can be varied in order to maximize magnetic field distribution. When using a continuous-processing device, a tank of the exogenous nucleic acids and the cells to be transformed is connected to the device and the exogenous nucleic acids and cells to be transformed are flowed through the tubing in the device.

The exogenous nucleic acids can be any nucleic acids where it is possible and desirable to express them inside cells. In one aspect, the nucleic acid fragments can be plasmids (linear or coiled, etc.), cosmids, phages, viruses, yeast artificial chromosomes, bacterial artificial chromosomes, other artificial chromosomes, and the like). The exogenous nucleic acids of interest introduced by the present method can be from any source, such as a nucleic acids obtained from cells in which they occur in nature, recombinantly-produced nucleic acids, or chemically-synthesized nucleic acids. For example, the nucleic acids can contain genes having nucleotide sequences corresponding to sequences in living organisms. The nucleic acids can also contain a mutated or altered form of a gene (e.g., a gene that differs from a naturally occurring gene by an alteration, deletion, substitution, or addition of at least one nucleotide residue), or can contain genes that do not occur in nature. In one aspect, the nucleic acid can be DNA and the DNA can be single stranded or double stranded.

In one aspect, the exogenous nucleic acid can contain genes that are desirable to express in a cell. In this aspect, the genes can code for proteins whose expression it is desired to increase.

In general, the methods described herein involve the application of an electromagnetic field to a sample containing the exogenous nucleic acid and a cell to be transformed in the absence of applied heat in order to transform the cell with the exogenous nucleic acid. Typically, the methods typically involve the application of a mini-current magnetic field to the sample in the absence of applied heat. Thus, the reaction is typically performed at a constant temperature of less than or equal to about 30° C., preferably less than or equal to about 25° C. The magnitude and duration of the magnetic field applied to the nucleic acid can vary. For example, the magnitude of the magnetic field applied in steps (a) and (b) above can be the same or different. Similarly, the duration of exposure to the magnetic field can be the same or different in steps (a) and (b). Different voltages can be used including different mini-currents to induce the magnetic field B by the magnetic-field inducing circuit. In one aspect, the voltage/mini-current is 50 mV/25 mA, 100 mV/50 mA, 150 mV/80 mA, 200 mV/100 mA, 250 mV/100 mA, 300 mV/150 mA, 500 mV/250 mA, 800 mV/400 mA, 1000 mV/500 mA, 1500 mV/800 mA, or 2000 mV/1000 mA. In another aspect, the voltage and mini-current in steps (a) and (b) are from 50 mV to 2,000 mV and from 25 mA to 1,000 mA. In another aspect, the voltage and mini-current in steps (a) and (b) are from 800 mV to 1,000 mV and from 400 mA to 500 mA. In a further aspect, the duration of exposure of the sample to the magnetic field B in steps (a) and (b) can range from 5 minutes to 60 minutes, from 5 minutes to 50 minutes, from 5 minutes to 40 minutes, from 5 minutes to 30 minutes, or from 5 minutes to 20 minutes. When using a batch-processing device, the vials containing the sample are held in place on the vial support for the duration of exposure of the sample to the magnetic field B in steps (a) and (b). When using a continuous-processing device, the exogenous nucleic acid and cells are flowed through the tubing in the device at a rate selected to achieve a residence time for the duration of exposure of the sample to the magnetic field B in steps (a) and (b). In addition, the proportions of the reagents used in the reaction are the same whether using the batch-processing device or the continuous-processing device, however, the volumes of the final reaction mix typically can be in the range of about 10 µL to about 1000 liters when using the continuous-processing device. In yet another aspect, the magnetic field B induced by the mini-current is about 0.35 or about 0.36 Gauss. In a typical use of the method, the voltage is about 12V and the mini-current is about 900 mA, and the induced magnetic field B is about 0.35 Gauss. Devices for generating the mini-current magnetic field and exposing the sample of nucleic acid to the magnetic field are described in detail above.

In a further aspect, the cells and exogenous DNA are exposed to an electromagnetic field of 0.36 Gauss, a current of 900 mA, and a voltage of 12V. In another aspect, the cells and exogenous DNA are exposed to an electromagnetic field for 15 min. In a further aspect, the electromagnetic field is applied externally to the vial or tube containing the exogenous DNA and the cells to be transformed. In a still further aspect, neither the tubes or vials, nor the mixtures of cells and exogenous DNA within them, need to be in direct physical contact with any electrodes for the transformation to be accomplished.

The sample of cells and exogenous nucleic acid can be prepared using techniques known in the art for preparing samples used in conventional transformation techniques. For example, the cells and the nucleic acid can be dissolved in water and buffer, where the buffered solution contains a divalent cation such as $Ca^{2+}$ or $Mg^{2+}$ (for bacteria) or an alkali cation such as $Cs^+$ or $Li^+$ (for yeasts). In one aspect, the cells to be transformed are competent without any modifications or treatments. In another aspect, the cells are made competent through one of many procedures known in the art. In a further aspect, exposure to an external magnetic field, such as by putting the cells in the devices disclosed herein, renders the cells competent. In one aspect, the process for making cells competent involves incubation on ice and/or heat shock steps. In another aspect, the heat shock steps are carried out for from 30 to 90 seconds at 40° C. or greater. In one aspect, cells are heat shocked at 42° C. for 45-50 seconds. In a further aspect, the cells can optionally be diluted prior to plating. In a still further aspect, plated cells can be incubated for from 16 to 48 hours before performing a cell count. Methods for assessing the effectiveness of transformation, for plating cells, and the like, are discussed in the following section.

The methods described herein can be used in any application where conventional transformation is used. For example, the methods described herein permit the uptake of plasmids containing DNA cassettes that incorporate several genes.

IV. Biological Devices

In one aspect, a "biological device" is formed when a cell is transfected or transformed with the DNA construct described herein. In one aspect, a DNA construct comprising an expression vector and one or more nucleic acid fragments that have been ligated into the expression vector using the methods described herein is carried by the expression vector into the cell and is separate from the host cell's genome. In another aspect, the DNA construct is incorporated into the host cell's genome.

The host cells as referred to herein include their progeny, which are any and all subsequent generations formed by cell division. It is understood that not all progeny may be identical due to deliberate or inadvertent mutations. A host cell may be "transfected" or "transformed," which refers to a process by which exogenous nucleic acid is transferred or introduced into the host cell. A transformed cell includes the primary subject cell and its progeny. The host cells can be naturally-occurring cells or "recombinant" cells. Recombinant cells are distinguishable from naturally-occurring cells in that naturally-occurring cells do not contain heterologous nucleic acid sequences introduced using molecular biology techniques. In one aspect, the host cell is a prokaryotic cell, such as, for example, *E. coli*. In other aspects, the host cell is yeast such as, for example, *Saccharomyces cerevisiae*. Host cells transformed with the DNA construct described herein are referred to as biological devices.

Biological devices such as those described herein can be used for many different purposes. In one aspect, the biological device can increase the production of a desired metabolite produced by a plant. The term "metabolite" as defined herein is any chemical compound produced by the plant, where it is desirable to produce increased quantities of the compound. Examples of metabolites include compounds having nutritional or medicinal value as well as any other commercial value. In another aspect, the biological device can increase the production of a protein that is useful in the food, pharmaceutical, petroleum, fuel, or other industries.

It is understood that one way to define the variants and derivatives of the genetic components and DNA constructs described herein is through defining the variants and derivatives in terms of homology/identity to specific known sequences. Those of skill in the art readily understand how to determine the homology of two nucleic acids. For example, the homology can be calculated after aligning the two sequences so that the homology is at its highest level. Another way of calculating homology can be performed by published algorithms (see Zuker, M. Science 244:48-52, 1989, Jaeger et al. Proc. Natl. Acad. Sci. USA 86:7706-7710, 1989, Jaeger et al. Methods Enzymol. 183:281-306, 1989, which are herein incorporated by reference for at least material related to nucleic acid alignment).

As used herein, "conservative" mutations are mutations that result in an amino acid change in the protein produced from a sequence of DNA. When a conservative mutation occurs, the new amino acid has similar properties as the wild type amino acid and generally does not drastically change the function or folding of the protein (e.g., switching isoleucine for valine is a conservative mutation since both are small, branched, hydrophobic amino acids). "Silent mutations," meanwhile, change the nucleic acid sequence of a gene encoding a protein but do not change the amino acid sequence of the protein.

It is understood that the description of conservative mutations and homology can be combined together in any combination, such as embodiments that have at least 70%, 75%, 80%, 85%, 90%, 95%, or 99% homology to a particular sequence wherein the variants are conservative mutations. It is understood that any of the sequences described herein can be a variant or derivative having the homology values listed above.

In one aspect, a database such as, for example, GenBank, can be used to determine the sequences of genes and/or regulatory regions of interest, the species from which these elements originate, and related homologous sequences.

In another aspect, the DNA construct further includes (a) a promoter, (b) a terminator or stop sequence, (c) a gene that confers resistance to an antibiotic (a "selective marker"), (d) a reporter protein, or a combination thereof.

In one aspect, a regulatory sequence is already incorporated into a vector such as, for example, a plasmid, prior to genetic manipulation of the vector. In another aspect, the regulatory sequence can be incorporated into the vector through the use of restriction enzymes or any other technique known in the art.

In one aspect, the regulatory sequence is a promoter. The term "promoter" refers to a DNA sequence capable of controlling the expression of a coding sequence. In one aspect, the coding sequence to be controlled is located 3' to the promoter. In another aspect, the promoter is derived from a native gene. In an alternative aspect, the promoter is composed of multiple elements derived from different genes and/or promoters. A promoter can be assembled from elements found in nature, from artificial and/or synthetic elements, or from a combination thereof. It is understood by those skilled in the art that different promoters can direct the expression of a gene in different tissues or cell types, at different stages of development, in response to different environmental or physiological conditions, and/or in different species. In one aspect, the promoter functions as a switch to activate the expression of a gene.

In one aspect, the promoter is "constitutive." A constitutive promoter is a promoter that causes a gene to be expressed in most cell types at most times. In another aspect, the promoter is "regulated." A regulated promoter is a promoter that becomes active in response to a specific stimulus. A promoter may be regulated chemically, such as, for example, in response to the presence or absence of a particular metabolite (e.g., lactose or tryptophan), a metal ion, a molecule secreted by a pathogen, or the like. A promoter may also be regulated physically, such as, for example, in response to heat, cold, water stress, salt stress, oxygen concentration, illumination, wounding, or the like.

Promoters that are useful to drive expression of the nucleotide sequences described herein are numerous and familiar to those skilled in the art. Suitable promoters include, but are not limited to, the following: T3 promoter, T7 promoter, Fe promoter, and GAL1 promoter. Variants of these promoters are also contemplated. The skilled artisan will be able to use site-directed mutagenesis and/or other mutagenesis techniques to modify the promoters to promote more efficient function. The promoter may be positioned, for example, from 10-100 nucleotides away from a ribosomal binding site.

In another aspect, the regulatory sequence is a terminator or stop sequence. As used herein, a terminator is a sequence of DNA that marks the end of a gene or operon to be transcribed. In a further aspect, the terminator is an intrinsic terminator or a Rho-dependent transcription terminator. As used herein, an "intrinsic terminator" is a sequence wherein a hairpin structure can form in the nascent transcript and wherein the hairpin disrupts the mRNA/DNA/RNA polymerase complex. As used herein, a "Rho-dependent" transcription terminator requires a Rho factor protein complex to disrupt the mRNA/DNA/RNA polymerase complex.

In a further aspect, the regulatory sequence includes both a promoter and a terminator or stop sequence. In a still further aspect, the regulatory sequence can include multiple promoters or terminators. Other regulatory elements, such as enhancers, are also contemplated. Enhancers may be located from about 1 to about 2000 nucleotides in the 5' direction from the start codon of the DNA to be transcribed, or may be located 3' to the DNA to be transcribed. Enhancers may be "cis-acting," that is, located on the same molecule of DNA as the gene whose expression they affect. In a still further aspect, the regulatory sequence includes a ribosomal binding site, a riboswitch, or a combination thereof.

In certain aspects, the DNA construct can include a gene that expresses a reporter protein. The selection of the reporter protein can vary. For example, the reporter protein can be a yellow fluorescent protein, red fluorescent protein, a green fluorescent protein, or a cyan fluorescent protein. The amount of fluorescence that is produced by the biological device can be correlated to the amount of DNA incorporated into the plant cells. The fluorescence produced by the device can be detected and quantified using techniques known in the art. For example, spectrofluorometers are typically used to measure fluorescence. The Examples provide exemplary procedures for measuring the amount of fluorescence as a result of the expression of DNA.

The DNA construct described herein can be part of a vector. In one aspect, the vector is a plasmid, a phagemid, a cosmid, a yeast artificial chromosome, a bacterial artificial chromosome, a virus, a phage, or a transposon.

In general, plasmid vectors containing replicon and control sequences that are derived from species compatible with the host cell are used in connection with these hosts. Vectors capable of high levels of expression of recombinant genes and proteins are well known in the art. The vector ordinarily carries a replication origin as well as marking sequences that are capable of providing phenotypic selection in transformed cells. Plasmid vectors useful for the transformation of a variety of host cells are well known and are commercially available. Such vectors include, but are not limited to, pWLNEO, pSV2CAT, pOG44, PXT1, pSG (Stratagene), pSVK3, pBSK, pBR322, pYES, pYES2, pBSKII, and pUC vectors.

Plasmids are double-stranded, autonomously-replicating, genetic elements that are not integrated into host cell chromosomes. Further, these genetic elements are usually not part of the host cell's central metabolism. In bacteria, plasmids may range from 1 kilobase (kb) to over 200 kb. Plasmids can be engineered to encode a number of useful traits including the production of secondary metabolites, antibiotic resistance, the production of useful proteins, degradation of complex molecules and/or environmental toxins, and others. Plasmids have been the subject of much research in the field of genetic engineering, as plasmids are convenient expression vectors for foreign DNA in, for example, microorganisms. Plasmids generally contain regulatory elements such as promoters and terminators and also usually have independent replication origins. Ideally, plasmids will be present in multiple copies per host cell and will contain selectable markers (such as genes for antibiotic resistance) to allow the ordinarily skilled artisan to select host cells that have been successfully transfected with the plasmids (for example, by culturing the host cells in a medium containing the antibiotic).

In one aspect, the vector encodes a selection marker. In a further aspect, the selection marker is a gene that confers resistance to an antibiotic. In certain aspects, during fermentation of host cells transformed with the vector, the cells are contacted with the antibiotic. For example, the antibiotic may be included in the culture medium. Cells that have not been successfully transformed cannot survive in the presence of the antibiotic; only cells containing the vector that confers antibiotic resistance can survive. Optionally, only cells containing the vector to be expressed will be cultured, as this will result in the highest production efficiency of the desired gene products. Cells that do not contain the vector would otherwise compete with transformed cells for resources. In one aspect, the antibiotic is tetracycline, neomycin, kanamycin, ampicillin, hygromycin, chloramphenicol, amphotericin B, bacitracin, carbapenam, cephalosporin, ethambutol, fluoroquinolones, isonizid, methicillin, oxacillin, vancomycin, streptomycin, quinolines, rifampin, rifampicin, sulfonamides, cephalothin, erythromycin, streptomycin, gentamycin, penicillin, other commonly-used antibiotics, or a combination thereof.

In an alternative aspect, if the host cells are yeasts, selection can accomplished by the use of auxotrophic markers. In one aspect, the yeasts lack the ability to synthesize or use a particular nutrient such as, for example, a nucleotide, an amino acid, or a sugar. In this aspect, the expression vector comprises a gene or genes that compensates for the missing function. The medium for growing the host cells is selected such that only transformed cells will grow (e.g., phenylalanine auxotrophs are grown on media lacking phenylalanine).

In one aspect, when the vector is a plasmid, the plasmid can also contain a multiple cloning site or polylinker. In a further aspect, the polylinker contains recognition sites for multiple restriction enzymes. The polylinker can contain up to 2, 3, 4, 5, 6, 7, 8, 9, 10, 11, 12, 13, 14, 15, 16, 17, 18, 19, 20, or more than 20 recognition sites for restriction enzymes. Further, restriction sites may be added, disabled, or removed as required, using techniques known in the art. In one aspect, the plasmid contains restriction sites for any known restriction enzyme such as, for example, HindIII, KpnI, SacI, BamHI, BstXI, EcoRI, BsaBI, NotI, XhoI, SphI, SbaI, ApaI, SalI, ClaI, EcoRV, PstI, SmaI, XmaI, SpeI, EagI, SacII, or any combination thereof. In a further aspect, the plasmid contains more than one recognition site for the same restriction enzyme.

In one aspect, the restriction enzyme can cleave DNA at a palindromic or an asymmetrical restriction site. In a further aspect, the restriction enzyme cleaves DNA to leave blunt ends; in an alternative aspect, the restriction enzyme cleaves DNA to leave "sticky" or overhanging ends. In another aspect, the enzyme can cleave DNA a distance of from 20 bases to over 1000 bases away from the restriction site. A variety of restriction enzymes are commercially available and their recognition sequences, as well as instructions for use (e.g. amount of DNA needed, precise volumes of reagents, purification techniques, as well as information about salt concentration, pH, optimum temperature, incubation time, and the like) are made available by commercial enzyme suppliers.

In one aspect, a plasmid with a polylinker containing one or more restriction sites can be digested with one restriction enzyme and a nucleotide sequence of interest can be ligated into the plasmid using a commercially-available DNA ligase enzyme. Several such enzymes are available, often as kits containing all reagents and instructions required for use. In another aspect, a plasmid with a polylinker containing two or more restriction sites can be simultaneously digested with two restriction enzymes and a nucleotide sequence of interest can be ligated into the plasmid. Using two restriction enzymes provides an asymmetric cut in the DNA, allowing for insertion of a nucleotide sequence of interest in a particular direction and/or on a particular strand of the double-stranded plasmid. Since RNA synthesis from a DNA template proceeds from 5' to 3', often starting just after a promoter, the order and direction of elements inserted into a plasmid is especially important. If a plasmid is to be simultaneously digested with multiple restriction enzymes, these enzymes must be compatible in terms of buffer, salt concentration, and other incubation parameters.

In some aspects, prior to ligation, a plasmid that has been digested with a restriction enzyme is treated with an alkaline phosphatase enzyme to remove 5' terminal phosphate groups. This prevents self-ligation of the plasmid and thus facilitates ligation of heterologous or exogenous nucleic acid fragments into the plasmid.

In one aspect, the exogenous nucleic acids used in the DNA constructs described herein can be amplified using the polymerase chain reaction (PCR) prior to being ligated into a plasmid or other vector. Typically, PCR-amplification techniques make use of primers or short, chemically-synthesized oligonucleotides that are complementary to regions on each respective strand flanking the DNA or nucleotide sequence to be amplified. A person having ordinary skill in the art will be able to design or choose primers based on the desired experimental conditions. In general, primers should be designed to provide for efficient and faithful replication of the target nucleic acids. Two primers are required for the amplification of each gene, one for the sense strand (that is, the strand containing the gene of interest) and one for the antisense strand (that is, the strand complementary to the gene of interest). Pairs of primers should have similar melting temperatures that are close to the PCR reaction's annealing temperature. In order to facilitate the PCR reaction, the following features should be avoided in primers: mononucleotide repeats, complementarity with other primers in the mixture, self-complementarity, and internal hairpins and/or loops. Methods of primer design are known in the art; additionally, computer programs exist that can assist the ordinarily skilled practitioner with primer design. Primers can optionally incorporate restriction enzyme recognition sites at their 5' ends to assist in later ligation into plasmids or other vectors.

PCR can be carried out using purified DNA, unpurified DNA that has been integrated into a vector, or unpurified genomic DNA. The process for amplifying target DNA using PCR consists of introducing an excess of two primers having the characteristics described above to a mixture containing the sequence to be amplified, followed by a series of thermal cycles in the presence of a heat-tolerant or thermophilic DNA polymerase, such as, for example, any of Taq, Pfu, Pwo, Tfl, rTth, Tli, or Tma polymerases. A PCR "cycle" involves denaturation of the DNA through heating, followed by annealing of the primers to the target DNA, followed by extension of the primers using the thermophilic DNA polymerase and a supply of deoxynucleotide triphosphates (i.e., dCTP, dATP, dGTP, and TTP), along with buffers, salts, and other reagents as needed. In one aspect, the DNA segments created by primer extension during the PCR process can serve as templates for additional PCR cycles. Many PCR cycles can be performed to generate a large concentration of target DNA or gene. PCR can optionally be performed in a device or machine with programmable temperature cycles for denaturation, annealing, and extension steps. Further, PCR can be performed on multiple genes simultaneously in the same reaction vessel or microcentrifuge tube since the primers chosen will be specific to selected genes. PCR products can be purified by techniques known in the art such as, for example, gel electrophoresis followed by extraction from the gel using commercial kits and reagents.

In another aspect, an electromagnetic PCR process can be performed to amplify the desired nucleic acid fragments, with or without the presence of polymerases and primers. In a further aspect, the electromagnetic PCR process can be carried out in the ligation and/or transformation device described herein.

In a further aspect, the vector can include an origin of replication, allowing it to use the host cell's replication machinery to create copies of itself.

As used herein, "operably linked" refers to the association of nucleic acid sequences on a single nucleic acid fragment so that the function of one affects the function of another. For example, if sequences for multiple genes are inserted into a single plasmid, their expression may be operably linked. Alternatively, a promoter is said to be operably linked with a coding sequence when it is capable of affecting the expression of the coding sequence.

As used herein, "expression" refers to transcription and/or accumulation of an mRNA derived from a gene or DNA fragment. Expression may also be used to refer to translation of mRNA into a peptide, polypeptide, or protein.

Exemplary methods for producing the DNA constructs described herein are provided in the Examples. Restriction enzymes and purification techniques known in the art can be used to prepare the DNA constructs. After the vector incorporating the DNA construct has been produced, it can be incorporated into host cells using the methods described below.

Once the DNA construct has been incorporated into the host cell, the cells are cultured such that the cells multiply. A satisfactory microbiological culture contains available sources of hydrogen donors and acceptors, carbon, nitrogen, sulfur, phosphorus, inorganic salts, and, in certain cases, vitamins or other growth promoting substances. The addition of peptone provides a readily available source of nitrogen and carbon. A variety of other carbon sources are contemplated, including, but not limited to: monosaccharides such as glucose and fructose, disaccharides such as lactose and sucrose, oligosaccharides, polysaccharides such as starch, and mixtures thereof. Unpurified mixtures extracted from feedstocks are also contemplated and can include molasses, barley malt, and related compounds and compositions. Other glycolytic and tricarboxylic acid cycle intermediates are also contemplated as carbon sources, as are one-carbon substrates such as carbon dioxide and/or methanol in the cases of compatible organisms. The carbon source utilized is limited only by the particular organism being cultured.

Furthermore, the use of different media results in different growth rates and different stationary phase densities. Secondary metabolite production is highest when cells are in stationary phase. A rich media results in a short doubling time and higher cell density at stationary phase. Minimal media results in slow growth and low final cell densities. Efficient agitation and aeration increase final cell densities. A skilled artisan will be able to determine which type of media is best suited to culture a particular species and/or strain of host cell.

Culturing or fermenting of host cells may be accomplished by any technique known in the art. In one aspect, batch fermentation can be conducted. In batch fermentation, the composition of the culture medium is set at the beginning of culturing and the system is closed to future artificial alterations. In some aspects, a limited form of batch fermentation can be carried out, wherein factors such as oxygen concentration and pH are manipulated, but additional carbon is not added. Continuous fermentation methods are also contemplated. In continuous fermentation, equal amounts of a defined medium are continuously added to and removed from a bioreactor. In other aspects, microbial host cells are immobilized on a substrate. Fermentation can be carried out on any scale and may include methods in which literal "fermentation" is carried out as well as other culture methods that are non-fermentative.

EXAMPLES

The following examples are put forth so as to provide those of ordinary skill in the art with a complete disclosure and description of how the compounds, compositions, and methods described and claimed herein are made and evaluated, and are intended to be purely exemplary and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions. The device used to prepare these examples was the amplification device 50 described above and shown in FIGS. 1-9.

Materials and Methods

Sample Treatment

All DNA sequences used during analysis were provided and synthesized by CloneTex Systems Inc. (Austin, Tex. 78756, USA). Thin-walled PCR tubes were used during all experiments and inside the system to ensure that potential energy had an effect on the sample. All DNA concentrations were measured with a standard NanoVue spectrophotometer (GE Healthcare Biosciences, P.O. Box 643065 Pittsburgh, Pa. 15264-3065), and also with a standard UV/visible spectrophotometer using a ratio of absorbances at 260 nm and 280 nm (GE Healthcare Biosciences P.O. Box 643065 Pittsburgh, Pa. 15264-3065).

Ligation

Example 1

The following protocol was used to perform DNA ligations in the devices disclosed herein. The desired DNA sequences of parts to be ligated were incorporated into plasmids obtained from CloneTex Systems, Inc. Each part to be ligated was cut from the plasmid using one or more restriction enzymes including HindIII, KpnI, XhoI, EcoRI, and BamHI. Gene parts were then purified by gel electrophoresis. Stock solutions containing identical concentrations of the parts to be ligated were prepared and mixed in equal proportions, usually 5 μL of each. Restriction sites at the ends of each part to be ligated allowed matching of the parts and the construction of an insert containing the parts in the desired order from 5' to 3'.

Ratio of vector to insert was optimized by running parallel experiments with 3:5, 2:1, and 1:1 proportions of these components, respectively. After ratio optimization, for ligation experiments, two sets of identical samples were prepared. Plasmid vector (pBSK) was mixed with insert in a 1:2 ratio (by mass) in a thin-walled PCR tube for a total solution volume of 9 μL. 8 μL of T4 DNA ligase (Promega, 1 Weiss unit/μL) and 12 μL of 10× ligase buffer were added, following a protocol provided by the manufacturer (Promega LigaFast Rapid DNA Ligation System). Samples were then incubated either (1) at room temperature for 15 minutes or (2) in the electromagnetic device with a 12V mini-current of about 900 mA, which induced magnetic field of about 0.35 Gauss.

Figure 33:
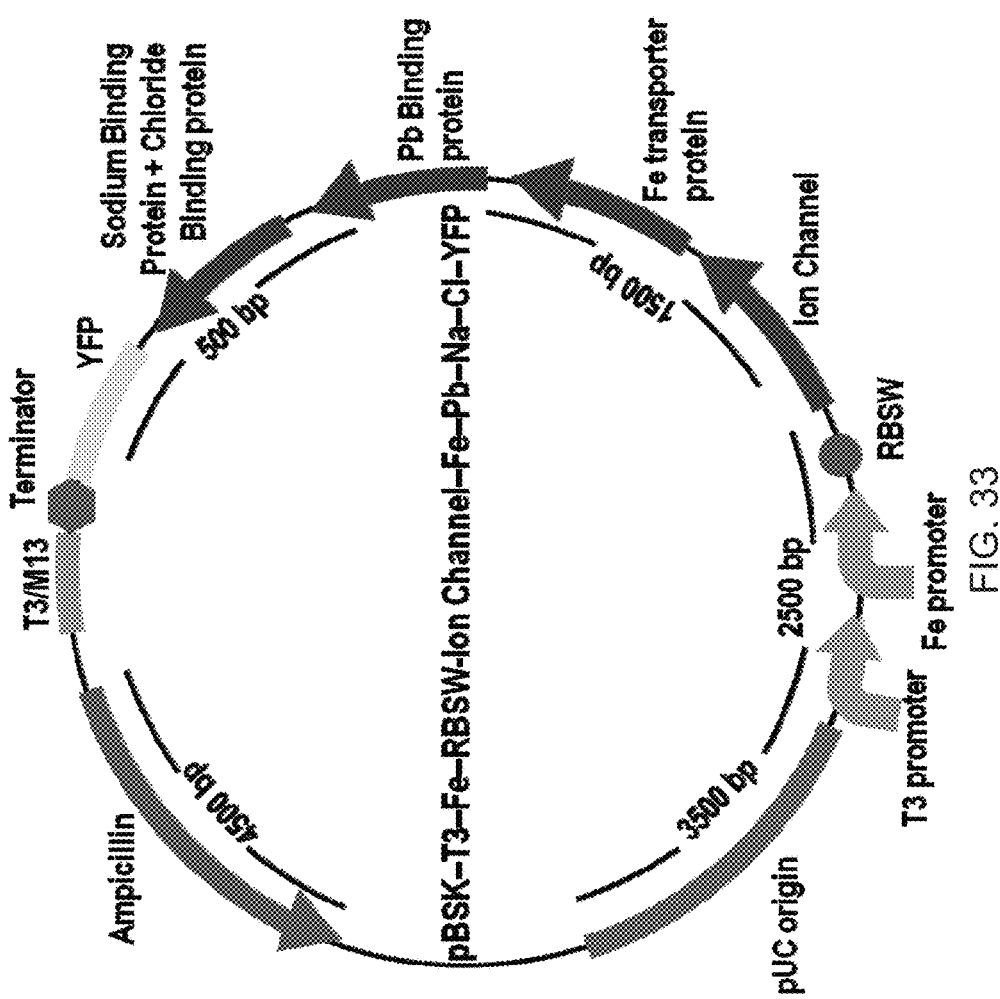
FIG. 33 is a map of a plasmid into which a synthetic insert has been ligated using the devices and methods disclosed herein. From 5' to 3', an iron (Fe) promoter, a ribosomal binding site (RBS), an ion channel, an iron (Fe) transporter protein, a lead (Pb) binding protein, a chloride (Cl) binding protein, and a yellow fluorescent reporter protein (YFP) have been added to a pBSK plasmid that already contained a pUC origin, a T3 promoter, and an ampicillin resistance gene.

Successful ligation was verified using gel electrophoresis. A novel plasmid construct containing, from 5' to 3', an iron promoter, a ribosomal binding site, an ion channel, an iron transporter protein, a lead binding protein, a chloride binding protein, and a yellow fluorescent reporter protein was successfully ligated using the methods disclosed herein. A schematic of this plasmid is shown in FIG. 33. The DNA device was constructed by assembling a plasmid (pBSK) having the genetic components in the following order: (1) a gene that expresses an iron promoter protein (SEQ ID NO. 5; (2) a riboswitch (SEQ ID NO. 2); a gene that expresses an ion channel protein (SEQ ID NO. 10); a gene that expresses an iron transporter protein (SEQ ID NO. 6); a gene that expresses a lead binding protein (SEQ ID NO. 7); a gene that expresses a chloride binding protein (SEQ ID NO. 8); a gene that expresses a sodium binding protein (SEQ ID NO. 9); a gene that expresses yellow fluorescence protein (SEQ ID NO. 4).

Figure 34:
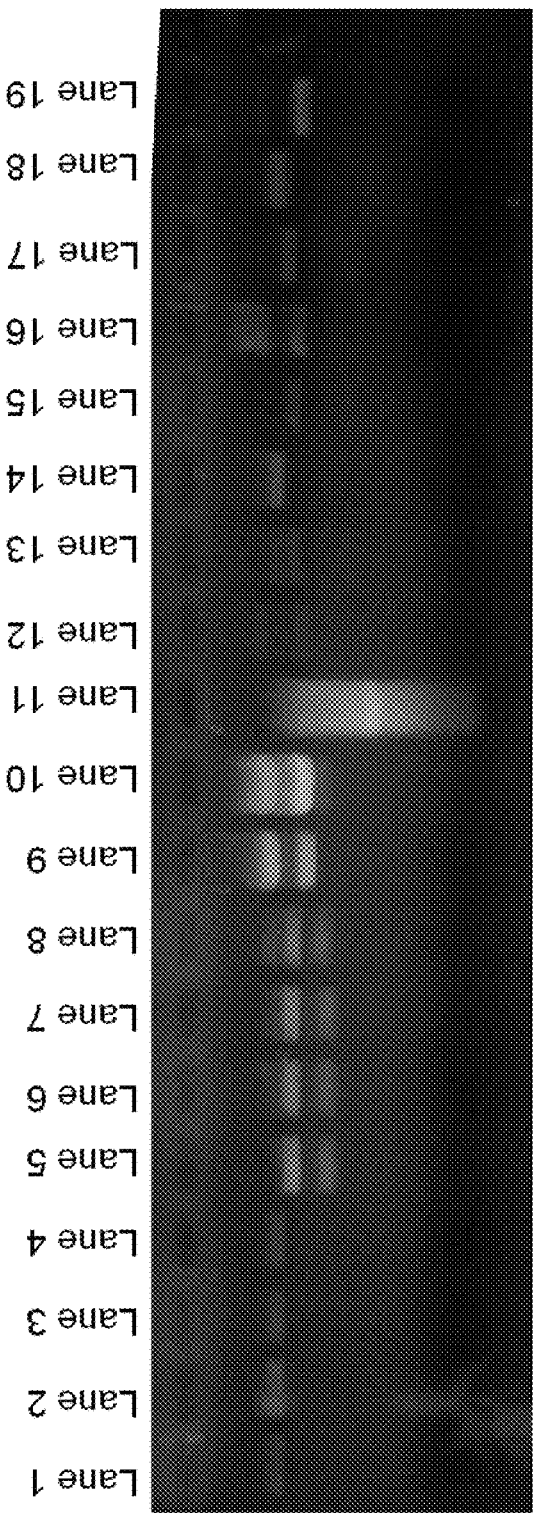
FIG. 34 is an image of a gel of the different gene parts ligated to form one of the inserts disclosed herein. Lanes 1-4 are the iron promoter digested with XbaI and XhoI restriction enzymes. Lanes 5-7 are the RpoS riboswitch digested with XbaI and XhoI. Lane 8 is the ion channel digested with BamHI and XbaI. Lanes 9-10 are the iron transporter protein digested with BamHI and XbaI. Lane 11 contains a 1 kb molecular marker. Lane 12 is the lead binding protein digested with XbaI and XhoI. Lane 13 is the lead binding protein digested with BamHI. Lane 14 is the chloride binding protein digested with BamHI and XhoI. Lane 15 is the chloride binding protein digested with HindIII. Lane 16 is the chloride binding protein digested with BamHI. Lane 17 is the chloride binding protein digested with BamHI and XbaI. Lane 18 is the sodium binding protein digested with BamHI and HindIII. Lane 19 is the yellow fluorescent protein digested with XbaI and XhoI.

FIG. 34 shows a restriction enzyme digestion and electrophoretic gel separation of the plasmid from FIG. 33.

Figure 35:
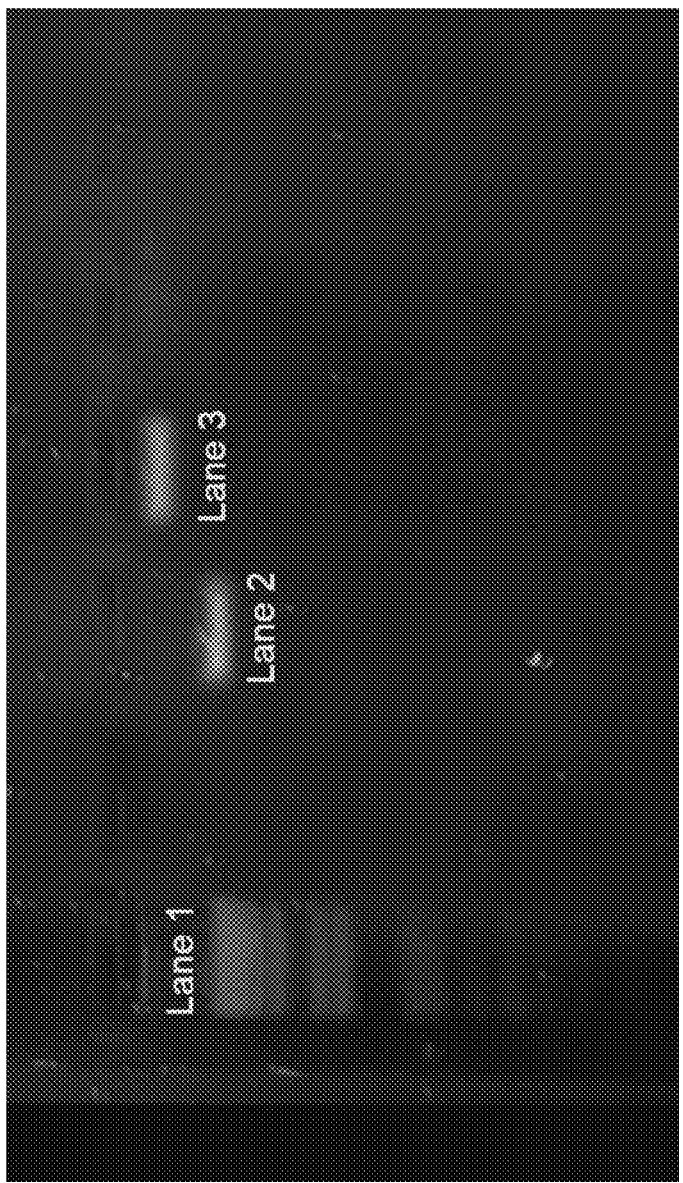
FIG. 35 is an image of a gel comparing different ligation methods. Lane 1 is a 1 kb molecular weight ladder. Lane 2 is gene parts ligated into a plasmid using a T4 DNA ligase but no mini-current. Lane 3 represents the same gene parts ligated into a plasmid using a mini-current but no DNA ligase.

FIG. 35 is an image of a gel comparing different ligation methods. Lane 1 is a 1 kb molecular weight ladder. Lane 2 is gene parts ligated into a plasmid using a T4 DNA ligase but no mini-current. Lane 3 represents the same gene parts ligated into a plasmid using a mini-current but no DNA ligase.

Example 2

Figure 38:
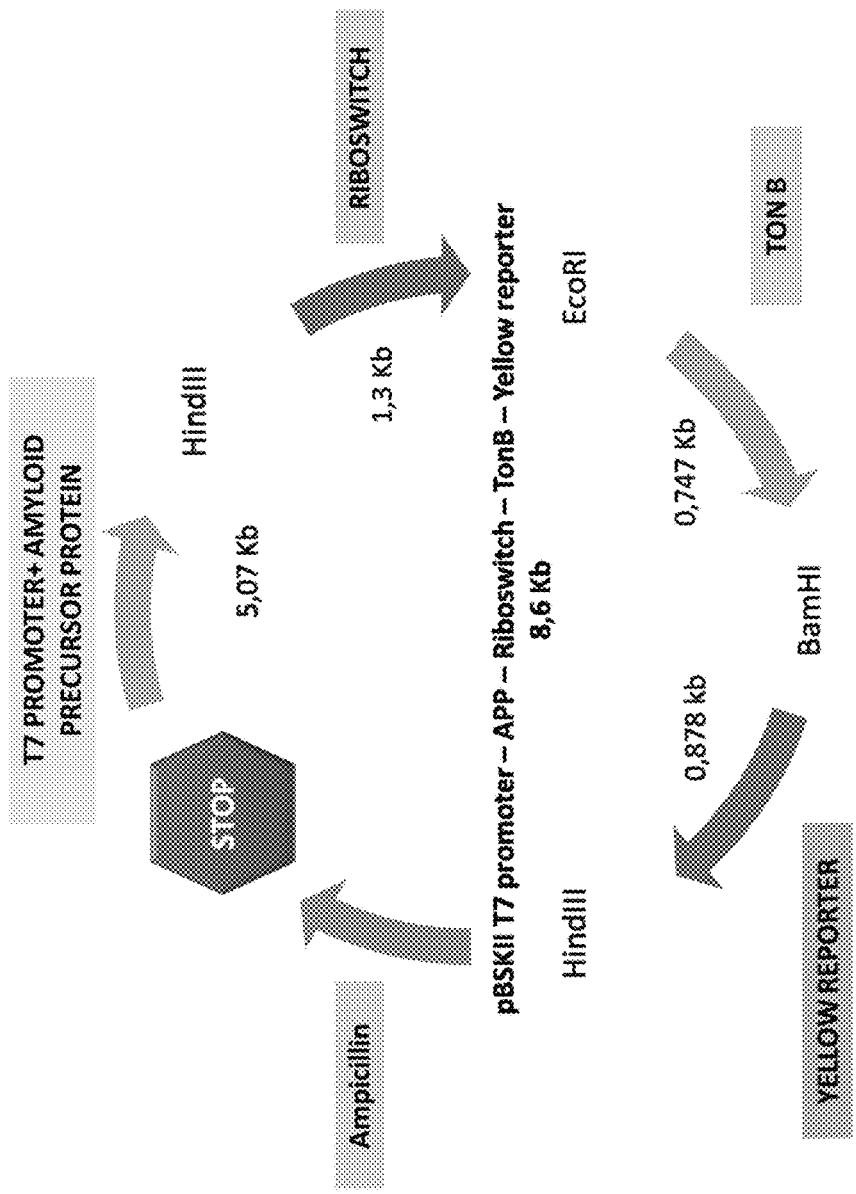
FIG. 38 shows an amyloid DNA construct described herein.

The DNA construct as depicted in FIG. 38 composed of genetic components described herein was assembled in plasmid vectors (e.g., pBSKII). Sequences of genes and/or proteins with desired properties were identified in GenBank; these included an amyloid precursor protein gene and a TonB gene. These sequences were synthesized by CloneTex Systems, Inc. (Austin, Tex.). Other genetic parts were also obtained for inclusion in the DNA constructs including, for example, promoter genes (e.g. T7 promoter), reporter genes (e.g. yellow fluorescent reporter protein), terminator sequences, and regulatory sequences (e.g. riboswitch). These genetic parts included restriction sites for ease of insertion into plasmid vectors.

Figure 39:
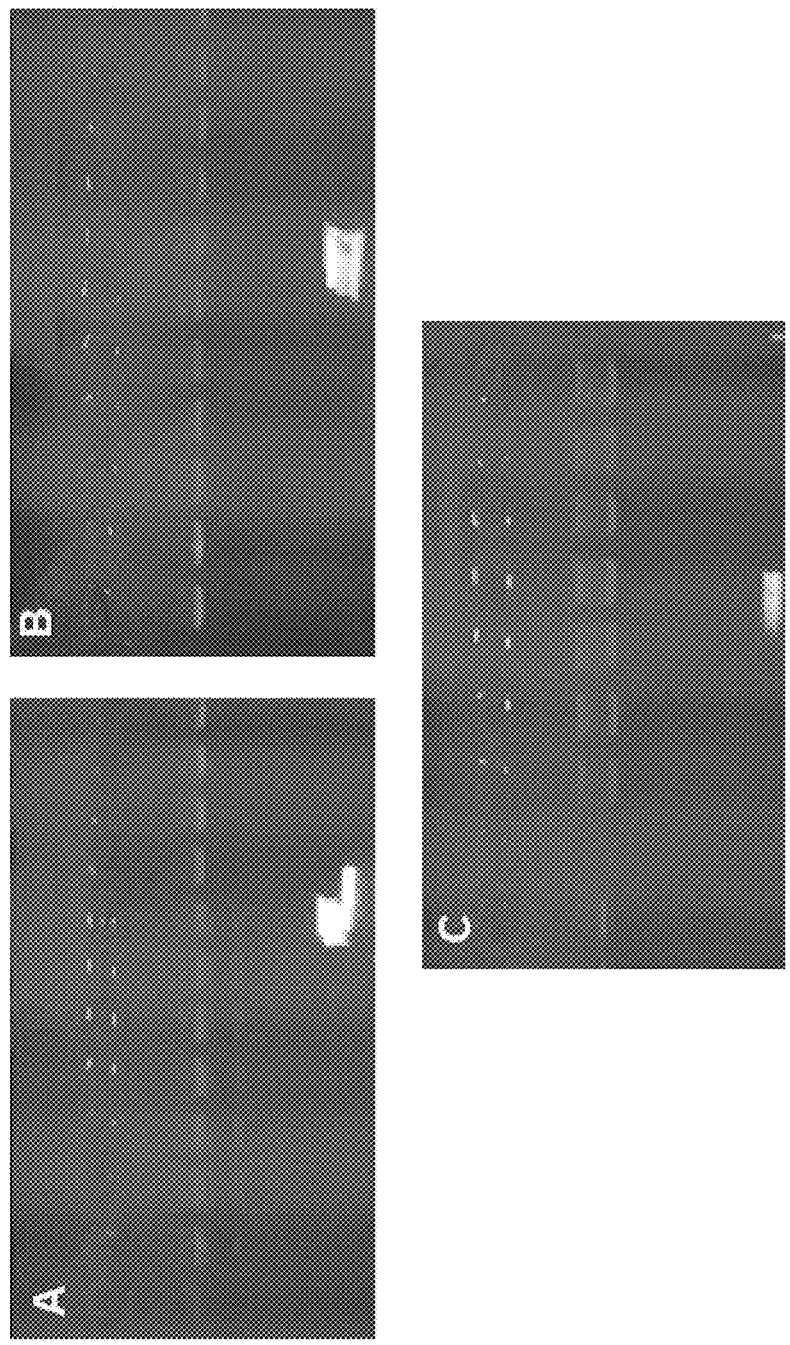
FIG. 39 shows images of electrophoresis gels of individual genetic parts used to synthesize the DNA construct described herein. (A) TonB gene; (B) riboswitch, (C) yellow fluorescent reporter gene.

The cloning of the DNA construct into the biological devices was performed as follows. Sequences of individual genes were amplified by polymerase chain reaction using primers that incorporated restriction sites at their 5' ends to facilitate construction of the full sequence to be inserted into the plasmid. Genes were excised from the plasmids in which they were provided using restriction enzymes. The excised fragments were purified by agarose gel electrophoresis (see FIG. 39) prior to ligation. Equal proportions of the riboswitch gene, the TonB gene, and the yellow fluorescent reporter gene were mixed.

A pBSKII plasmid already containing a gene for the amyloid precursor protein was then digested with HindIII restriction enzyme according to directions and using reagents provided by the enzyme's supplier (Promega). The complete insert, containing HindIII restriction sites on each end, was then ligated into the plasmid. A ratio of 3 parts backbone vector to 4 parts insert mixture was used for ligation. T4 DNA ligase, ligase buffer (supplied by Promega), and nuclease-free water were added to the mixture of vector and insert. The reaction mixture was placed into an electromagnetic chamber and subjected to a minicurrent (900 mA) magnetic field with a strength of 0.35 Gauss. Successful construction of the insert and ligation of the insert into the plasmid were confirmed by gel electrophoresis.

A schematic of the DNA construct is depicted in FIG. 38. From 5' to 3', the construct includes T7 promoter, a gene expressing amyloid precursor protein, a riboswitch, a gene expressing TonB protein, a yellow fluorescent reporter protein, a terminator or stop sequence, and a selective marker for ampicillin resistance. The DNA construct was incorporated into a pBSKII plasmid.

PCR was used to enhance DNA concentration using a Mastercycler Personal 5332 ThermoCycler (Eppendorf North America) with specific sequence primers and the standard method for amplification (Sambrook, J., E. F. Fritsch, and T. Maniatis. 1989. Molecular cloning: A Laboratory Manual, 2nd ed., vol. 1. Cold Spring Harbor Laboratory Press, Cold Spring Harbor, N.Y.). Digestion and ligation were used to ensure assembly of DNA synthesized parts using restriction enzymes and reagents (PCR master mix, restriction enzymes: EcoRI, BamHI and HindIII, alkaline phosphatase and quick ligation kit, all from Promega). DNA was quantified using a NanoVue spectrophotometer (GE Life Sciences) and a standard UV/visible spectrophotometer using the ratio of absorbances at 260 nm versus 280 nm. In order to verify final ligations, DNA was visualized and purified via electrophoresis using a Thermo EC-150 power supply.

The DNA construct was made with gene parts having sequence sizes ranging from 747 to 1300 bp, including gene parts fundamental for expression of such as, for example, a riboswitch, a promoter, a reporter gene, and transcriptional terminators or stops. Backbone plasmids and synthetic inserts can be mixed together for ligation purposes at different ratios. In one aspect, the ratio of backbone plasmid to synthetic insert is 3:4. After the vector comprising the DNA construct has been produced, the resulting vector can be incorporated into the host cells using the methods described below.

Figure 40:
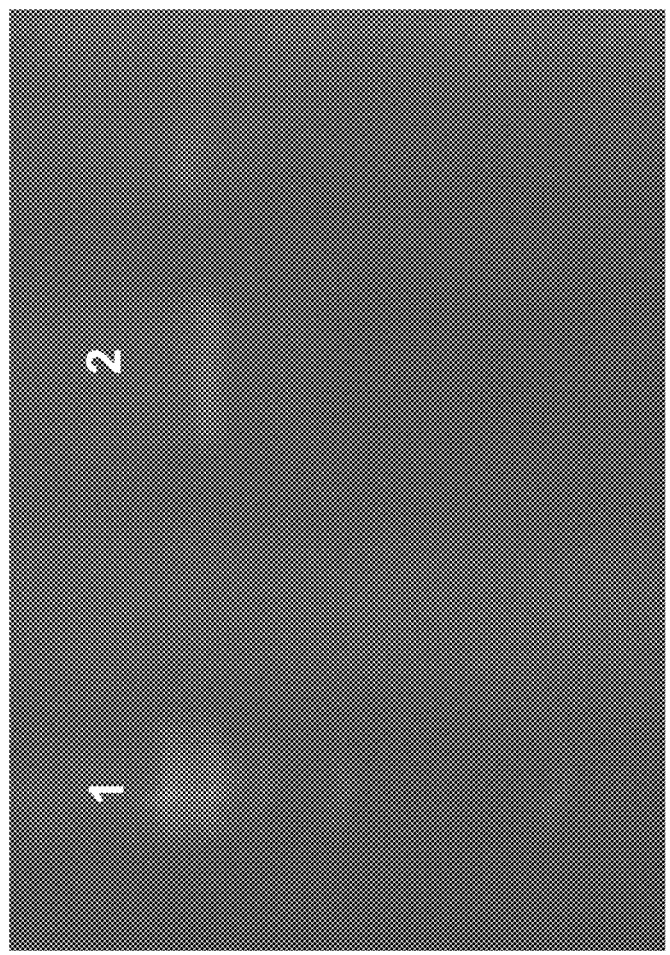
FIG. 40 shows an image of an electrophoresis gel of the complete DNA construct described herein. Lane 1: 1 kb molecular weight marker. Lane 2: DNA construct.

The DNA device was constructed by assembling a plasmid (pBSKII) having the genetic components in the following order: (1) a gene that expresses amyloid precursor protein (SEQ ID NO. 1; T7 promoter and amyloid precursor protein together are 5070 bp), (2) a riboswitch (SEQ ID NO. 2, 1300 bp), and (3) a gene that expresses TonB protein (SEQ ID NO. 3, 747 bp). In certain embodiments, the reporter protein (SEQ ID NO. 4, 878 bp) that produces fluorescence can be incorporated into the plasmid prior to the terminator from the 5' to 3' direction. The amount of fluorescence correlates to protein production in media. The DNA construct was transformed into cells, as described below, to produce the biological devices. A plasmid containing the DNA construct is shown in FIG. 38. A gel of the successfully-ligated DNA construct is shown in FIG. 40.

Results of ligation experiments using standard ligation techniques using T4 DNA ligase but no mini-current, are presented in Table 7.

TABLE 7

Comparison of Standard and Electromagnetic Ligations

| Type of Ligation | Reaction Time (min.) | Successful Ligation | Concentration of Ligated DNA (ng/µL) |
|---|---|---|---|
| Standard | 40 | NO | NA |
| Electromagnetic | 40 | YES | 35.5 |

Transformation

Example 3

The first transformation protocol was as follows. Frozen competent cells were thawed on ice. Cells were transferred to a chilled tube and amplified DNA was added. The tube was placed on ice for 10 minutes. Cells were then heat shocked for 45-50 seconds in a water bath at 42° C. without shaking. Heat-shocked cells were then placed on ice for two minutes. 500 µL of cold SOC medium (2% w/v tryptone, 0.5% w/v yeast extract, 8.56 mM NaCl, 2.5 mM KCl, 10 mM $MgCl_2$, 10 mM $MgSO_4$, 20 mM glucose) was added, followed by thorough mixing. 250 µL of each mix was transferred to thin-wall PCR tubes and placed into the electromagnetic PCR chamber with an electromagnetic field of 0.36 Gauss, a current of 900 mA, and a voltage of 12 V, for 15 minutes.

A bacterial culture with an optical density (OD) of 0.04 was used for transformations. 100 µL of transformed cells were used for plate inoculation (streaking/loop method) on LB agar medium with ampicillin antibiotic. No dilution of cells was made prior to plate inoculation.

The transformation results are provided in Table 8, where the results are an average of three plates. Referring to Table 8, when E. coli was transformed with PT amplified by conventional thermocycler PCR, the number of colony forming units was 3.3 to 4.0 over 16 to 48 hours. When E. coli was transformed with PT amplified by thermal-free electromagnetic PCR, the number of colony forming units was 23 to 26 over 16 to 48 hours. In summary, a significantly higher number E. coli colonies transformed with plasmid amplified by thermal-free electromagnetic PCR as compared to the lower number of colonies transformed with plasmid amplified by conventional thermocycler PCR.

TABLE 8

| DNA | Colony forming units at 16 hours | Colony forming units at 24 hours | Colony forming units at 32 hours | Colony forming units at 48 hours |
|---|---|---|---|---|
| DNA from Thermoylcler PCR of Tocopherol PT | Mean: 3.3 +/−SD: 1.2 | Mean: 4.0 +/−SD: 2.1 | Mean: 4.0 +/−SD: 2.1 | Mean: 4.0 +/−SD: 2.1 |
| DNA from electromagnetic PCR (15 minutes) of Tocopherol PT | Mean: 23.0 +/−SD: 2.1 | Mean: 24.3 +/−SD: 2.0 | Mean: 26.0 +/−SD: 2.9 | Mean: 26.0 +/−SD: 2.9 |
| Control DNA without amplification from Tocopherol PT in plasmid PYES | Mean: 7.3 +/−SD: 6.9 | Mean: 8.0 +/−SD: 7.8 | Mean: 11.6 +/−SD: 13.0 | Mean: 11.6 +/−SD: 13.0 |

Figure 36:
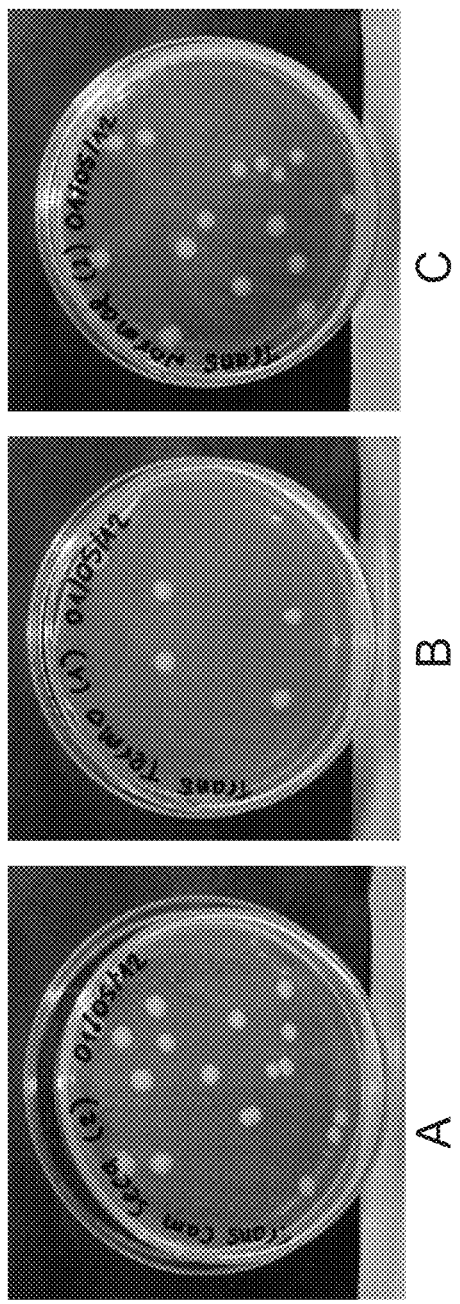
FIG. 36 shows plated transformed *E. coli* cells.

FIG. 36 shows representative examples of plated transformed cells. 36A shows E. coli transformed with tocopherol PT DNA amplified by an electromagnetic PCR method. FIG. 36B shows E. coli transformed with tocopherol PT DNA amplified by a traditional thermocycled PCR method. FIG. 36C shows *E. coli* transformed with tocopherol PT DNA that was not amplified prior to transformation. The presence of a colony indicates a successful transformation; cells were plated on ampicillin-containing medium since the exogenous tocopherol PT plasmids contained a selective marker for ampicillin resistance.

Example 4

A second transformation experiment was performed using the DNA construct produced in Example 1. FIG. 37 shows *E. coli* cells transformed with exogenous plasmid DNA containing ligation device as depicted in FIG. 33. FIG. 37A is a control reaction performed as above but omitting ligase. FIG. 37B shows cells transformed with electromagnetically ligated DNA according to the methods and devices described herein. FIG. 37C shows cells transformed with DNA ligated using T4 ligase and room temperature ligation. The presence of a colony indicates successful transformation; visualization is by reporter protein fluorescence. The greater number of colonies in FIG. 37B demonstrates that ligation is more complete and successful using the electromagnetic devices and methods disclosed herein than using conventional molecular biology techniques. A comparison of transformations performed with conventionally-ligated and electromagnetically-ligated DNA is presented in Table 9.

DNA expression and effectiveness of transformation were determined by fluorescence of the transformed cells expressed in fluorescence units (FSUs), according a protocol provided by the manufacturer, using a 20/20 Luminometer (Promega). The blue fluorescence module (with a 450 nm excitation wavelength and a 600 nm emission wavelength) was used to evaluate the effectiveness of transformation. When no fluorescent reporter protein was assembled, no fluorescence was observed. Plasmid DNA extraction purification, PCR, and gel electrophoresis were also used to confirm transformation.

Figure 41:
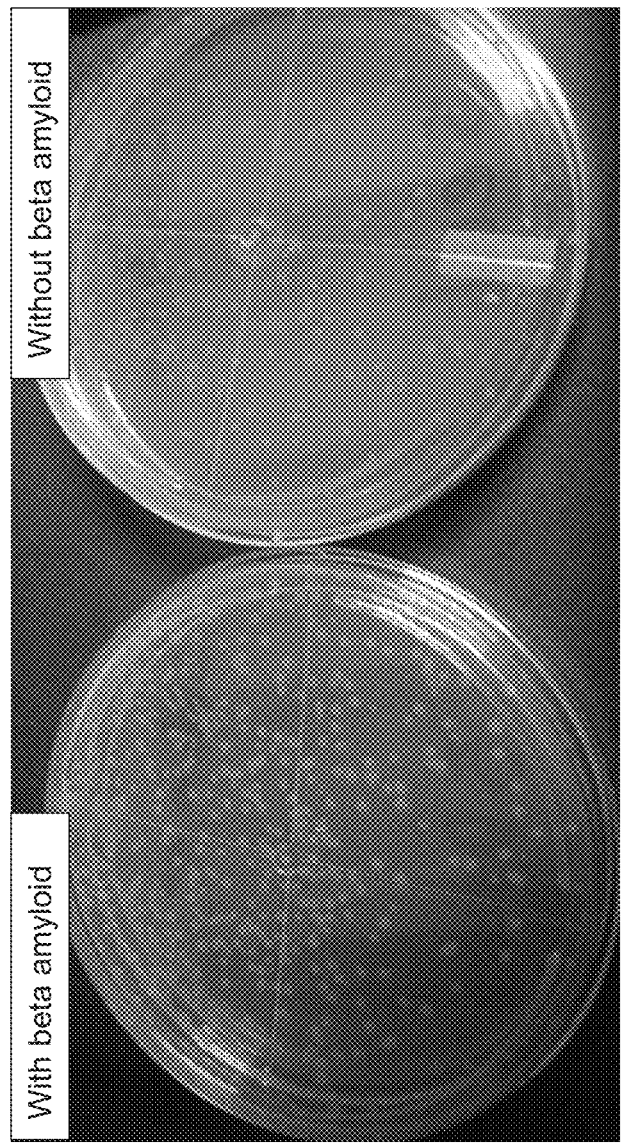
FIG. 41 shows growth of cells on media containing metals. Left: cells transformed with the DNA construct described herein. Right: untransformed cells.

The development of 6-amyloid in the presence of metals was assessed. Transformed cells containing the DNA construct described herein were plated on 250 µL of agar with suitable media containing either 1 mM or 2 mM of iron metal, iron sulfate, copper chloride, or copper sulfate (i.e., 8 separate experiments). A positive control consisting of transformed cells that did not include a gene for the amyloid precursor protein was also assessed. Bacterial populations were assessed by counting colony forming units (CFUs). Results are presented in Table 10 and FIG. 41.

TABLE 9

Comparison of Transformation Effectiveness Using Conventionally- and Electromagnetically-Ligated DNA

| Ligation Type | CFU[a] (×10$^6$) | DNA (ng/µL) ± SD | RNA (ng/µL) ± SD | ATP (RLU[b]) ± SD | Fluorescence (FSU[c]) ± SD |
|---|---|---|---|---|---|
| Electromagnetic | 309 | 50.7 ± 2.5 | 104.8 ± 1.2 | 415 ± 28.5 | 16731 ± 437 |
| Conventional (T4 Ligase) | 126 | 16.2 ± 2.5 | 8.9 ± 1.4 | 82 ± 12.4 | 1992 ± 124 |

[a]Colony forming units
[b]Relative luminescence units
[c]Fluorescence units

Example 5

A third transformation experiment was performed using the DNA construct produced in Example 2. Top10 Chemically Competent *E. coli* cells from Life Technologies were transformed with the DNA construct described herein using a modified version of a protocol provided by the supplier. 25 µL of cells were mixed with 5 µL of the DNA construct. Cells were placed on ice for 20 min. Cells were then subjected to heat shock for 50 seconds at 42° C. After heat shock, cells were once again incubated on ice for 2 min. 250 µL of SOC medium (2% w/v tryptone, 0.5% w/v yeast extract, 8.56 mM NaCl, 2.5 mM KCl, 10 mM MgCl$_2$, 10 mM MgSO$_4$, 20 mM glucose) were added to the mixture of cells and inserts. The samples were placed in an electromagnetic chamber and subjected to a minicurrent (900 mA) that created a magnetic field of 0.35 Gauss for 15 minutes. After electromagnetic exposure, 100 µL aliquots were plated in petri dishes with SOB agar (same as SOC but without the glucose), ampicillin, isopropyl β-D-1-thiogalactopyranoside (IPTG), and 5-bromo-4-chloro-3-indolyl-β-D-galactopyranoside (X-gal). Petri dishes were then incubated for 18 hours.

TABLE 10

CFU Count for Cells with and without DNA Construct Grown in Metal-Containing Media

| Metal (1 mM) | With DNA Construct | Without DNA Construct |
|---|---|---|
| Iron | 55 × 10$^6$ | 50 × 10$^6$ |
| Iron Sulfate | 79 × 10$^6$ | 70 × 10$^6$ |
| Copper Sulfate | 59 × 10$^6$ | 35 × 10$^6$ |
| Copper Chloride | 84 × 10$^6$ | 47 × 10$^6$ |
| None | 29 × 10$^6$ | 23 × 10$^6$ |

Thus, cells transformed with the DNA construct described herein are better able to survive in media containing metal ions.

Throughout this application, various publications are referenced. The disclosures of these publications in their entireties are hereby incorporated by reference into this application in order to more fully describe the compounds, compositions and methods described herein.

Various modifications and variations can be made to the compounds, compositions and methods described herein. Other aspects of the compounds, compositions and methods described herein will be apparent from consideration of the specification and practice of the compounds, compositions and methods disclosed herein. It is intended that the specification and examples be considered as exemplary.

What is claimed is:

1. A method for ligating nucleic acid fragments, the method comprising exposing a sample consisting of (1) water or a buffered solution, (2) the nucleic acid fragments, and (3) optionally a ligase to an electromagnetic field, wherein the nucleic acid fragments are ligated after exposure to the electromagnetic field.

2. The method of claim 1, wherein the sample includes a ligase.

3. The method of claim 1, wherein the sample does not include a ligase.

4. The method of claim 1, wherein the electromagnetic field is applied externally to a container holding the sample.

5. The method of claim 1, wherein the electromagnetic field is from about 0.001 gauss to about 0.61 gauss as applied to the sample at a centerline of a container holding the sample, and wherein the electromagnetic field is induced by operating an electromagnetic-field-inducing circuit at a current of about 0.005 A to about 1.5 A.

6. The method of claim 1, wherein the electromagnetic field is from about 0.322 gauss to about 0.61 gauss as applied to the sample at a centerline of a container holding the sample, and wherein the electromagnetic field is induced by operating an electromagnetic-field-inducing circuit at a current of about 0.8 A to about 1.5 A.

7. The method of claim 1, wherein the electromagnetic field is from about 0.322 gauss to about 0.402 gauss as applied to the sample at a centerline of a container holding the sample, and wherein the electromagnetic field is induced by operating an electromagnetic-field-inducing circuit at a current of about 0.8 A to about 1.0 A.

8. The method of claim 1, wherein the method is thermal-free.

9. The method of claim 1, wherein the sample comprising the nucleic acid fragments is exposed to an electromagnetic field for from about 5 minutes to about 60 minutes.

10. The method of claim 1, wherein the sample comprising the nucleic acid fragments is exposed to an electromagnetic field for about 15 minutes.

11. The method of claim 1, wherein the sample is placed in a device comprising:
a circuit including at least one conductor through which a mini-current is passed to induce a electromagnetic field;
at least one tube having a working portion through which the nucleic acid sample flows for continuous processing of the sample;
a tube support adapted to support the tube working portion, and the nucleic acid sample carried therein, within the electromagnetic field; and
a control unit adapted to control the mini-current and the induced electromagnetic field, wherein the nucleic acid sample is amplified in response to being subjected to the electromagnetic field,
wherein the conductor of the electromagnetic-field-inducing circuit and the tube working portion are positioned to provide a uniform exposure of the nucleic acid sample in the tube working portion to the electromagnetic field.

12. The method of claim 11, wherein the electromagnetic-field-inducing circuit is adapted so that the nucleic-acid amplification is thermal-free.

13. The method of claim 11, wherein the control unit is adapted to operate the electromagnetic-field-inducing circuit at a mini-current of about 0.8 A to about 1.5 A to induce an electromagnetic field of about 0.322 Gauss to about 0.61 Gauss as applied to the sample at a centerline of the container of the sample.

14. The method of claim 11, wherein the control unit is adapted to operate the electromagnetic-field-inducing circuit at a mini-current of about 0.005 A to about 1.0 A to induce an electromagnetic field of about 0.001 Gauss to about 0.402 Gauss.

15. The method of claim 11, wherein the conductor of the electromagnetic-field-inducing circuit and the tube working portion are positioned equidistantly from each other along entire lengths thereof to provide a uniform exposure of the nucleic acid sample in the tube working portion to the electromagnetic field.

16. The method of claim 15, wherein the conductor of the electromagnetic-field-inducing circuit is positioned below the tube support and the tube working portion is positioned above the tube support, with the conductor and tube working portion vertically aligned in conforming arrangements.

17. The method of claim 15, wherein the tube working portion is arranged in serpentine configuration and the conductor is arranged in a conforming serpentine configuration so that they are vertically aligned and equidistantly separated along their entire lengths.

18. The method of claim 11, wherein the control unit include a pumps for flowing the nucleic acid sample through the tube working portion.

19. The method of claim 11, wherein the tube includes an inlet and an outlet at opposite ends of the tube working portion, the inlet includes a removable closure and is connectable to a sample tank, the outlet includes a removable closure and is connectable to a post-amplification device, and the tube has a diameter and a length selected to provide a predetermined residence time of the sample in the electromagnetic field for a given sample flow rate; wherein the control unit includes at least one input, at least one output, and at least one programmed processor; further comprising a housing for at least the electromagnetic-field-inducing circuit, the tube working portion, and the tube support; and further comprising a cooling system including a fan operable by the control unit.

20. The method of claim 1, wherein the nucleic acid fragment is an oligonucleotide, deoxyribonucleic acid, ribonucleic acid, or peptide nucleic acid.

21. The method of claim 1, wherein the nucleic acid fragment is cDNA, genomic DNA, or synthesized DNA.

22. The method of claim 1, wherein the nucleic acid fragment is a vector and DNA to be inserted in the vector.

23. The method of claim 22, wherein the vector is a plasmid selected from the group consisting of pWLNEO, pSV2CAT, pOG44, PXT1, pSG, pSVK3, pBSK, pBR322, pYES, pYES2, pBSKII, and pUC.

* * * * *